US007932364B2

(12) United States Patent
DeFrees et al.

(10) Patent No.: US 7,932,364 B2
(45) **Date of Patent: *Apr. 26, 2011**

(54) COMPOSITIONS AND METHODS FOR THE PREPARATION OF HUMAN GROWTH HORMONE GLYCOSYLATION MUTANTS

(75) Inventors: Shawn DeFrees, North Wales, PA (US); Henrik Clausen, Holte (DK)

(73) Assignee: Novo Nordisk A/S, Bagsvaerd (DE)

( * ) Notice: Subject to any disclaimer, the term of this patent is extended or adjusted under 35 U.S.C. 154(b) by 630 days.

This patent is subject to a terminal disclaimer.

(21) Appl. No.: 10/556,094

(22) PCT Filed: May 7, 2004

(86) PCT No.: PCT/US2004/014254

§ 371 (c)(1), (2), (4) Date: Apr. 16, 2007

(87) PCT Pub. No.: WO2004/103275

PCT Pub. Date: Dec. 2, 2004

(65) Prior Publication Data

US 2008/0102083 A1 May 1, 2008

Related U.S. Application Data

(60) Provisional application No. 60/469,114, filed on May 9, 2003, provisional application No. 60/494,751, filed on Aug. 13, 2003, provisional application No. 60/495,076, filed on Aug. 14, 2003, provisional application No. 60/535,290, filed on Jan. 8, 2004.

(51) Int. Cl.
*C07K 1/00* (2006.01)
*C07K 14/00* (2006.01)

(52) U.S. Cl. ......................... 530/397; 530/399; 530/350

(58) Field of Classification Search ........................ None
See application file for complete search history.

(56) References Cited

U.S. PATENT DOCUMENTS

| | | | |
|---|---|---|---|
| 4,055,635 | A | 10/1977 | Green et al. |
| 4,088,538 | A | 5/1978 | Schneider |
| 4,179,337 | A | 12/1979 | Davis et al. |
| 4,385,260 | A | 5/1983 | Watts et al. |
| 4,412,989 | A | 11/1983 | Iwashita et al. |
| 4,414,147 | A | 11/1983 | Klibanov |
| 4,438,253 | A | 3/1984 | Casey et al. |
| 4,496,689 | A | 1/1985 | Mitra |
| 4,565,653 | A | 1/1986 | Ives et al. |
| 4,806,595 | A | 2/1989 | Noishiki et al. |
| 4,826,945 | A | 5/1989 | Cohn et al. |
| 4,847,325 | A | 7/1989 | Shadle et al. |
| 4,879,236 | A | 11/1989 | Smith et al. |
| 4,925,796 | A | 5/1990 | Bergh et al. |
| 5,032,519 | A | 7/1991 | Paulson et al. |
| 5,104,651 | A | 4/1992 | Boone et al. |
| 5,122,614 | A | 6/1992 | Zalipsky |
| 5,147,788 | A | 9/1992 | Page et al. |
| 5,153,265 | A | 10/1992 | Shadle et al. |
| 5,154,924 | A | 10/1992 | Friden |
| 5,169,933 | A | 12/1992 | Anderson et al. |
| 5,182,107 | A | 1/1993 | Friden |
| 5,194,376 | A | 3/1993 | Kang |
| 5,202,413 | A | 4/1993 | Spinu |
| 5,219,564 | A | 6/1993 | Zalipsky et al. |
| 5,281,698 | A | 1/1994 | Nitecki |
| 5,324,663 | A | 6/1994 | Lowe |
| 5,324,844 | A | 6/1994 | Zalipsky |
| 5,342,940 | A | 8/1994 | Ono et al. |
| 5,346,696 | A | 9/1994 | Kim et al. |
| 5,352,670 | A | 10/1994 | Venot |
| 5,369,017 | A | 11/1994 | Wong et al. |
| 5,374,541 | A | 12/1994 | Wong |
| 5,374,655 | A | 12/1994 | Kashem et al. |
| 5,405,753 | A | 4/1995 | Brossmer |
| 5,410,016 | A | 4/1995 | Hubbell et al. |
| 5,432,059 | A | 7/1995 | Bean |
| 5,446,090 | A | 8/1995 | Harris |
| 5,492,841 | A | 2/1996 | Craig |
| 5,527,527 | A | 6/1996 | Friden |
| 5,529,914 | A | 6/1996 | Hubbell et al. |
| 5,545,553 | A | 8/1996 | Gotschlich |
| 5,583,042 | A | 12/1996 | Roth |
| 5,605,793 | A | 2/1997 | Stemmer |
| 5,614,184 | A | 3/1997 | Sytkowski et al. |
| 5,621,039 | A | 4/1997 | Hallahan et al. |

(Continued)

FOREIGN PATENT DOCUMENTS

| | | | |
|---|---|---|---|
| EP | 0474313 | A | 3/1992 |

(Continued)

OTHER PUBLICATIONS

Hansen et al. (1995) Biochem. J. 308:801-813.*
Abeijon et al., 1986, J. Biol. Chem. 261(24):11374-11377.
Abuchowski et al., 1977, J. Biol. Chem. 252:3578-3581.
Abuchowski et al., 1977, J. Biol. Chem. 252:3582-3586.
Abuchowski et al., 1984, Cancer Biochem. Biophys. 7:175-186.
Ailor et al., 2000, Glycobiology 10:837-847.
Alam et al., 1998. Journal of Biotechnology. 65: 183-190.
Allegre et al., 2006, J. Membrane Science 269:109-117.
Altmann et al., 1999, Glycoconjugate J. 16:109-123.

(Continued)

*Primary Examiner* — Michael Pak
(74) *Attorney, Agent, or Firm* — Leydig, Voit & Mayer, Ltd.

(57) ABSTRACT

The present invention relates to mutants of human growth hormone, which contain newly introduced N-linked or O-linked glycosylation site(s), such that these recombinantly produced polypeptides have glycosylation patterns distinctly different from that of the naturally occurring human growth hormone. The polynucleotide coding sequences for the mutants, expression cassettes comprising the coding sequences, cells expressing the mutants, and methods for producing the mutants are also disclosed. Further disclosed are pharmaceutical compositions comprising the mutants and method for using the mutants.

33 Claims, 10 Drawing Sheets

U.S. PATENT DOCUMENTS

| | | | |
|---|---|---|---|
| 5,629,384 A | 5/1997 | Veronese et al. | |
| 5,635,603 A | 6/1997 | Hansen et al. | |
| 5,643,575 A | 7/1997 | Martinez et al. | |
| 5,646,113 A | 7/1997 | Attie et al. | |
| 5,672,662 A | 9/1997 | Harris et al. | |
| 5,672,683 A | 9/1997 | Friden et al. | |
| 5,705,367 A | 1/1998 | Gotschlich | |
| 5,716,812 A | 2/1998 | Withers et al. | |
| 5,728,554 A | 3/1998 | Bayer et al. | |
| 5,770,420 A | 6/1998 | Lowe et al. | |
| 5,798,233 A | 8/1998 | Gotschlich | |
| 5,811,238 A | 9/1998 | Stemmer et al. | |
| 5,824,778 A | 10/1998 | Ishikawa et al. | |
| 5,824,864 A | 10/1998 | Fox et al. | |
| 5,830,721 A | 11/1998 | Stemmer et al. | |
| 5,833,988 A | 11/1998 | Friden | |
| 5,834,251 A | 11/1998 | Maras et al. | |
| 5,837,458 A | 11/1998 | Minshull et al. | |
| 5,849,535 A | 12/1998 | Cunningham et al. | |
| 5,858,751 A | 1/1999 | Paulson et al. | |
| 5,858,752 A | 1/1999 | Seed et al. | |
| 5,876,980 A | 3/1999 | DeFrees et al. | |
| 5,922,577 A | 7/1999 | Defrees et al. | |
| 5,932,462 A | 8/1999 | Harris et al. | |
| 5,945,314 A | 8/1999 | Prieto et al. | |
| 5,945,322 A | 8/1999 | Gotschlich | |
| 5,955,347 A | 9/1999 | Lowe | |
| 5,962,294 A | 10/1999 | Paulson et al. | |
| 5,969,040 A | 10/1999 | Hallahan et al. | |
| 5,977,307 A | 11/1999 | Friden | |
| 6,010,999 A | 1/2000 | Daley et al. | |
| 6,015,555 A | 1/2000 | Friden | |
| 6,030,815 A | 2/2000 | DeFrees et al. | |
| 6,037,452 A | 3/2000 | Minamino et al. | |
| 6,057,292 A | 5/2000 | Cunningham et al. | |
| 6,087,325 A | 7/2000 | Meers et al. | |
| 6,096,512 A | 8/2000 | Elhammer et al. | |
| 6,113,906 A | 9/2000 | Greenwald et al. | |
| 6,117,651 A | 9/2000 | Schultz et al. | |
| 6,166,183 A | 12/2000 | Ishikawa et al. | |
| 6,183,738 B1 | 2/2001 | Clark | |
| 6,261,805 B1 | 7/2001 | Wood | |
| 6,268,193 B1 | 7/2001 | Lowe | |
| 6,342,382 B1 | 1/2002 | Gotschlich | |
| 6,348,558 B1 | 2/2002 | Harris et al. | |
| 6,362,254 B2 | 3/2002 | Harris et al. | |
| 6,376,604 B2 | 4/2002 | Kozlowski | |
| 6,399,336 B1 | 6/2002 | Paulson et al. | |
| 6,399,337 B1 | 6/2002 | Taylor et al. | |
| 6,440,703 B1 | 8/2002 | DeFrees | |
| 6,465,220 B1 | 10/2002 | Hassan et al. | |
| 6,531,121 B2 | 3/2003 | Brines et al. | |
| 6,555,346 B1 | 4/2003 | Kretzdorn et al. | |
| 6,555,660 B2 | 4/2003 | Nissen et al. | |
| 6,586,398 B1 | 7/2003 | Kinstler et al. | |
| 6,692,931 B1 | 2/2004 | Reutter et al. | |
| 6,693,183 B2 | 2/2004 | Natsuka et al. | |
| 6,716,626 B1 | 4/2004 | Itoh et al. | |
| 6,743,896 B2 | 6/2004 | Filpula et al. | |
| 6,780,624 B2 | 8/2004 | Gotschlich | |
| 6,800,740 B1 * | 10/2004 | Cunningham et al. | 530/399 |
| 6,949,372 B2 | 9/2005 | Betenbaugh et al. | |
| 7,125,843 B2 | 10/2006 | DeFrees et al. | |
| 7,138,371 B2 | 11/2006 | DeFrees et al. | |
| 7,157,277 B2 | 1/2007 | DeFrees et al. | |
| 7,173,003 B2 | 2/2007 | DeFrees et al. | |
| 7,179,617 B2 | 2/2007 | DeFrees et al. | |
| 7,202,208 B2 | 4/2007 | Papadimitriou | |
| 7,214,660 B2 | 5/2007 | DeFrees et al. | |
| 7,226,903 B2 | 6/2007 | DeFrees et al. | |
| 7,229,962 B2 | 6/2007 | Chung et al. | |
| 7,235,638 B2 | 6/2007 | Persson | |
| 7,265,084 B2 | 9/2007 | DeFrees et al. | |
| 7,265,085 B2 | 9/2007 | DeFrees et al. | |
| 7,276,475 B2 | 10/2007 | DeFrees et al. | |
| 7,297,511 B2 | 11/2007 | DeFrees et al. | |
| 7,304,150 B1 | 12/2007 | Egrie et al. | |
| 7,338,933 B2 * | 3/2008 | DeFrees et al. | 514/8 |
| 7,368,108 B2 | 5/2008 | DeFrees et al. | |
| 7,399,613 B2 | 7/2008 | DeFrees et al. | |
| 7,405,198 B2 | 7/2008 | DeFrees et al. | |
| 7,416,858 B2 | 8/2008 | DeFrees et al. | |
| 7,439,043 B2 | 10/2008 | DeFrees et al. | |
| 7,473,680 B2 | 1/2009 | DeFrees et al. | |
| 7,524,813 B2 | 4/2009 | Zundel et al. | |
| 7,691,603 B2 | 4/2010 | DeFrees | |
| 7,696,163 B2 | 4/2010 | DeFrees et al. | |
| 7,795,210 B2 | 9/2010 | DeFrees et al. | |
| 7,803,777 B2 | 9/2010 | DeFrees | |
| 2002/0016003 A1 | 2/2002 | Saxon et al. | |
| 2002/0019342 A1 | 2/2002 | Bayer | |
| 2002/0037841 A1 | 3/2002 | Papadimitriou | |
| 2002/0115833 A1 | 8/2002 | Burg et al. | |
| 2002/0137134 A1 | 9/2002 | Gerngross et al. | |
| 2002/0142370 A1 | 10/2002 | Paulson et al. | |
| 2002/0150981 A1 | 10/2002 | Canfield | |
| 2002/0168323 A1 | 11/2002 | Gonda et al. | |
| 2002/0182586 A1 | 12/2002 | Morris et al. | |
| 2003/0027257 A1 | 2/2003 | Iatrou et al. | |
| 2003/0040037 A1 | 2/2003 | Bayer | |
| 2003/0124645 A1 | 7/2003 | Paulson et al. | |
| 2003/0166212 A1 | 9/2003 | Taylor et al. | |
| 2003/0166525 A1 | 9/2003 | Hoffmann et al. | |
| 2003/0180835 A1 | 9/2003 | Bayer | |
| 2003/0186850 A1 | 10/2003 | Clausen et al. | |
| 2003/0195338 A1 | 10/2003 | Chung et al. | |
| 2003/0207406 A1 | 11/2003 | Johnson et al. | |
| 2004/0043446 A1 | 3/2004 | DeFrees et al. | |
| 2004/0063911 A1 | 4/2004 | DeFrees et al. | |
| 2004/0077836 A1 | 4/2004 | DeFrees et al. | |
| 2004/0082026 A1 | 4/2004 | DeFrees et al. | |
| 2004/0102607 A1 * | 5/2004 | Danishefsky et al. | 530/322 |
| 2004/0115168 A1 | 6/2004 | DeFrees et al. | |
| 2004/0126838 A1 | 7/2004 | DeFrees et al. | |
| 2004/0132640 A1 | 7/2004 | DeFrees et al. | |
| 2004/0136955 A1 | 7/2004 | Barker | |
| 2004/0137557 A1 | 7/2004 | DeFrees et al. | |
| 2004/0197875 A1 | 10/2004 | Hauser et al. | |
| 2005/0026266 A1 | 2/2005 | Clausen et al. | |
| 2005/0031584 A1 | 2/2005 | DeFrees et al. | |
| 2005/0064540 A1 | 3/2005 | Defrees et al. | |
| 2005/0100982 A1 | 5/2005 | DeFrees et al. | |
| 2005/0106658 A1 | 5/2005 | DeFrees et al. | |
| 2005/0118672 A1 | 6/2005 | DeFrees et al. | |
| 2005/0143292 A1 | 6/2005 | DeFrees et al. | |
| 2005/0269265 A1 | 12/2005 | DeFrees | |
| 2005/0271690 A1 | 12/2005 | Gotschlich | |
| 2005/0288490 A1 | 12/2005 | Nakamoto et al. | |
| 2006/0024286 A1 | 2/2006 | Glidden | |
| 2006/0030521 A1 | 2/2006 | DeFrees et al. | |
| 2006/0035224 A1 | 2/2006 | Johansen | |
| 2006/0111279 A1 | 5/2006 | DeFrees et al. | |
| 2006/0177892 A1 | 8/2006 | De Frees | |
| 2006/0246544 A1 | 11/2006 | Kang et al. | |
| 2006/0276618 A1 | 12/2006 | DeFrees et al. | |
| 2006/0287224 A1 | 12/2006 | DeFrees et al. | |
| 2007/0014759 A1 | 1/2007 | DeFrees et al. | |
| 2007/0026485 A1 | 2/2007 | DeFrees et al. | |
| 2007/0027068 A1 | 2/2007 | DeFrees et al. | |
| 2007/0032405 A1 | 2/2007 | DeFrees et al. | |
| 2007/0059275 A1 | 3/2007 | DeFrees et al. | |
| 2007/0105755 A1 | 5/2007 | DeFrees et al. | |
| 2007/0154992 A1 | 7/2007 | DeFrees | |
| 2007/0254834 A1 | 11/2007 | DeFrees et al. | |
| 2007/0254836 A1 | 11/2007 | Defrees et al. | |
| 2008/0015142 A1 | 1/2008 | DeFrees et al. | |
| 2008/0050772 A1 | 2/2008 | DeFrees et al. | |
| 2008/0070275 A1 | 3/2008 | DeFrees et al. | |
| 2008/0102083 A1 | 5/2008 | DeFrees et al. | |
| 2008/0108557 A1 | 5/2008 | Behrens et al. | |
| 2008/0146494 A1 | 6/2008 | DeFrees et al. | |
| 2008/0146782 A1 | 6/2008 | DeFrees et al. | |
| 2008/0176790 A1 | 7/2008 | DeFrees | |
| 2008/0187955 A1 | 8/2008 | DeFrees et al. | |
| 2008/0200651 A1 | 8/2008 | Ostergaard et al. | |
| 2008/0206808 A1 | 8/2008 | DeFrees et al. | |
| 2008/0206810 A1 | 8/2008 | Johnson et al. | |

| | | | |
|---|---|---|---|
| 2008/0207487 | A1 | 8/2008 | DeFrees et al. |
| 2008/0242607 | A1 | 10/2008 | DeFrees |
| 2008/0242846 | A1 | 10/2008 | DeFrees et al. |
| 2008/0248959 | A1 | 10/2008 | DeFrees |
| 2008/0253992 | A1 | 10/2008 | DeFrees et al. |
| 2008/0255026 | A1 | 10/2008 | DeFrees et al. |
| 2008/0255040 | A1 | 10/2008 | DeFrees |
| 2008/0274958 | A1 | 11/2008 | DeFrees |
| 2008/0280818 | A1 | 11/2008 | DeFrees |
| 2008/0300173 | A1 | 12/2008 | DeFrees |
| 2008/0300175 | A1 | 12/2008 | DeFrees et al. |
| 2008/0305518 | A1 | 12/2008 | Klausen et al. |
| 2008/0305991 | A1 | 12/2008 | DeFrees et al. |
| 2008/0305992 | A1 | 12/2008 | DeFrees et al. |
| 2008/0318850 | A1 | 12/2008 | DeFrees et al. |
| 2008/0319183 | A1 | 12/2008 | DeFrees et al. |
| 2009/0028822 | A1 | 1/2009 | DeFrees et al. |
| 2009/0048440 | A1 | 2/2009 | Felo et al. |
| 2009/0053167 | A1 | 2/2009 | DeFrees |
| 2009/0054623 | A1 | 2/2009 | DeFrees |
| 2009/0055942 | A1 | 2/2009 | Ostergaard et al. |
| 2009/0008188 | A1 | 3/2009 | DeFrees et al. |
| 2009/0093399 | A1 | 4/2009 | DeFrees et al. |
| 2009/0124544 | A1 | 5/2009 | DeFrees |
| 2009/0137763 | A1 | 5/2009 | DeFrees et al. |
| 2009/0143292 | A1 | 6/2009 | Hinderer et al. |
| 2009/0169509 | A1 | 7/2009 | DeFrees et al. |
| 2009/0176967 | A1 | 7/2009 | Stennicke |
| 2009/0203579 | A1 | 8/2009 | DeFrees et al. |
| 2009/0227504 | A1 | 9/2009 | Klausen et al. |
| 2009/0240028 | A1 | 9/2009 | Behrens et al. |
| 2009/0252720 | A1 | 10/2009 | Ostergaard et al. |
| 2009/0253166 | A1 | 10/2009 | Zundel et al. |
| 2009/0264366 | A1 | 10/2009 | Johansen et al. |
| 2009/0292110 | A1 | 11/2009 | DeFrees |
| 2009/0305967 | A1 | 12/2009 | DeFrees et al. |
| 2010/0009902 | A1 | 1/2010 | DeFrees |
| 2010/0015684 | A1 | 1/2010 | DeFrees et al. |
| 2010/0028939 | A1 | 2/2010 | Behrens et al. |
| 2010/0029555 | A1 | 2/2010 | Tonon et al. |
| 2010/0035299 | A1 | 2/2010 | DeFrees et al. |
| 2010/0041872 | A1 | 2/2010 | DeFrees et al. |
| 2010/0048456 | A1 | 2/2010 | DeFrees et al. |
| 2010/0056428 | A1 | 3/2010 | Behrens |
| 2010/0075375 | A1 | 3/2010 | DeFrees et al. |
| 2010/0081791 | A1 | 4/2010 | DeFrees et al. |
| 2010/0113743 | A1 | 5/2010 | DeFrees et al. |
| 2010/0120666 | A1 | 5/2010 | Zopf et al. |
| 2010/0174059 | A1 | 7/2010 | DeFrees et al. |
| 2010/0210507 | A9 | 8/2010 | DeFrees et al. |

FOREIGN PATENT DOCUMENTS

| | | | |
|---|---|---|---|
| EP | 0585109 | A | 3/1994 |
| EP | 0605963 | A2 | 7/1994 |
| EP | 1428878 | A1 | 6/2004 |
| JP | H03-503759 | A | 8/1991 |
| WO | WO 87/00056 | | 1/1987 |
| WO | 89/06546 | A1 | 7/1989 |
| WO | WO 89/10134 | A1 | 11/1989 |
| WO | WO 90/07572 | | 7/1990 |
| WO | WO 90/08164 | A1 | 7/1990 |
| WO | WO 90/08823 | A1 | 8/1990 |
| WO | WO 90/13540 | A1 | 11/1990 |
| WO | WO 92/18135 | | 5/1993 |
| WO | WO 93/15189 | A1 | 8/1993 |
| WO | WO 94/04193 | A1 | 3/1994 |
| WO | WO 94/05332 | | 3/1994 |
| WO | WO 94/09027 | A1 | 4/1994 |
| WO | WO 94/15625 | A1 | 7/1994 |
| WO | WO 94/17039 | A1 | 8/1994 |
| WO | WO 94/18247 | A1 | 8/1994 |
| WO | WO 95/02421 | A1 | 1/1995 |
| WO | WO 96/40731 | | 6/1996 |
| WO | WO 96/21469 | A1 | 7/1996 |
| WO | WO 96/32491 | | 10/1996 |
| WO | 96/40881 | A1 | 12/1996 |
| WO | WO 97/05330 | | 2/1997 |
| WO | WO 98/05363 | | 2/1998 |
| WO | WO 87/05330 | A1 | 7/1998 |
| WO | WO 98/31826 | | 7/1998 |
| WO | 98/51784 | A1 | 11/1998 |
| WO | WO 98/58964 | | 12/1998 |
| WO | WO 99/00150 | A2 | 1/1999 |
| WO | WO 99/14259 | A1 | 3/1999 |
| WO | WO 99/22764 | A1 | 5/1999 |
| WO | WO 99/34833 | A1 | 7/1999 |
| WO | 99/48515 | A1 | 9/1999 |
| WO | WO 99/45964 | A1 | 9/1999 |
| WO | 99/55376 | A1 | 11/1999 |
| WO | WO 00/23114 | | 4/2000 |
| WO | WO 00/26354 | A1 | 5/2000 |
| WO | WO 00/65087 | | 11/2000 |
| WO | 01/02017 | A2 | 1/2001 |
| WO | WO 01/49830 | A2 | 7/2001 |
| WO | 01/58493 | A1 | 8/2001 |
| WO | WO 01/58935 | A2 | 8/2001 |
| WO | WO 01/60411 | A1 | 8/2001 |
| WO | 01/76640 | A2 | 10/2001 |
| WO | 01/88117 | A2 | 11/2001 |
| WO | WO 02/02597 | A2 | 1/2002 |
| WO | WO 02/13843 | A2 | 2/2002 |
| WO | WO 02/13873 | A1 | 2/2002 |
| WO | WO 02/053580 | A2 | 7/2002 |
| WO | WO 02/074806 | A2 | 9/2002 |
| WO | WO 02/002764 | A2 | 10/2002 |
| WO | WO 02/092619 | A2 | 11/2002 |
| WO | WO 03/017949 | A2 | 3/2003 |
| WO | WO 03/031464 | A2 | 4/2003 |
| WO | 03/045980 | A2 | 6/2003 |
| WO | 03/046150 | A2 | 6/2003 |
| WO | 03/093448 | A2 | 11/2003 |
| WO | 2004/009838 | A2 | 1/2004 |
| WO | WO 2004/010327 | A2 | 1/2004 |
| WO | 2004/022004 | A2 | 3/2004 |
| WO | WO 2004/033651 | A2 | 4/2004 |
| WO | 2004/046222 | A1 | 6/2004 |
| WO | 2004/083258 | A2 | 9/2004 |
| WO | 2004/083259 | A2 | 9/2004 |
| WO | 2004/091499 | A2 | 10/2004 |
| WO | WO 2004/096148 | A2 | 11/2004 |
| WO | WO 2004/099231 | A2 | 11/2004 |
| WO | WO 2004/103275 | A2 | 12/2004 |
| WO | 2005/012484 | A2 | 2/2005 |
| WO | 2005/025606 | A1 | 3/2005 |
| WO | WO 2005/025606 | A1 | 3/2005 |
| WO | 2005/051327 | A2 | 6/2005 |
| WO | 2005/055946 | A2 | 6/2005 |
| WO | 2005/056760 | A2 | 6/2005 |
| WO | 2005/067601 | A2 | 7/2005 |
| WO | WO 2005/067601 | A2 | 7/2005 |
| WO | 2005/070138 | A2 | 8/2005 |
| WO | 2005/072371 | A2 | 8/2005 |
| WO | WO 2005/070138 | A2 | 8/2005 |
| WO | 2005/091944 | A2 | 10/2005 |
| WO | 2005/121331 | A2 | 12/2005 |
| WO | WO 2005/121331 | A2 | 12/2005 |
| WO | 2006/010143 | A2 | 1/2006 |
| WO | 2006/014349 | A2 | 2/2006 |
| WO | 2006/014466 | A2 | 2/2006 |
| WO | 2006/020372 | A2 | 2/2006 |
| WO | WO 2006/014349 | A2 | 2/2006 |
| WO | WO 2006/014466 | A2 | 2/2006 |
| WO | 2006/031811 | A2 | 3/2006 |
| WO | WO 2006/031811 | A2 | 3/2006 |
| WO | 2006/050247 | A2 | 5/2006 |
| WO | 2006/074279 | A1 | 7/2006 |
| WO | 2006/074467 | A2 | 7/2006 |
| WO | 2006/078645 | A2 | 7/2006 |
| WO | WO 2006/074279 | A1 | 7/2006 |
| WO | WO 2006/078645 | A2 | 7/2006 |
| WO | 2006/105426 | A2 | 10/2006 |
| WO | 2006/121569 | A2 | 11/2006 |
| WO | 2006/127910 | A2 | 11/2006 |
| WO | 2007/022512 | A2 | 2/2007 |
| WO | 2007/056191 | A2 | 5/2007 |
| WO | 2008/011633 | A2 | 1/2008 |
| WO | WO 2008/011633 | A2 | 1/2008 |
| WO | 2008/057683 | A2 | 5/2008 |

WO 2008/060780 A2 5/2008
WO 2008/073620 A2 6/2008
WO 2008/124406 A2 10/2008
WO 2008/151258 A2 12/2008
WO 2008/154639 A2 12/2008
WO 2008/089396 A2 7/2009

OTHER PUBLICATIONS

Aplin et al., 1981, CRC Crit Rev. Biochem. 259-306.
Beauchamp et al., 1983, Anal Biochem.131:25-33.
Bedard et al., 1994, Cytotechnology 15:129-138.
Bennett et al., 1998, J. Biol. Chem. 273:30472-30481.
Bennett et al., 1999, FEBS Letters 460:226-230.
Berger et al., 1988, Blood 71:1641-1647.
Berg-Fussman et al. 1993, J. Biol. Chem. 268:14861-14866.
Bhadra et al., 2002, Pharmazie 57:5-29.
Bhatia et al., 1989, Anal. Biochem. 178:408-413.
Bickel et al., 2001, Adv. Drug Deliv. Rev. 46:247-279.
Bjoern, et al., 1992, J. Biol. Chem., 266(17):11051-11057.
Boccu et al., 1983, Z. Naturforsch 38C:94-99.
Boime et al., 1995, Endocrinology 136:2635-2640.
Boissel et al., 1993, J. Biol. Chem. 268:15983-15993.
Bork (2000) Genome Research 10:398-400.
Bork et al. (1996) Trends in Genetics 12(10): 425-427.
Bouizar et al., 1986, Eur. J. Biochem. 155:141-147.
Boyd et al., 1995, Mol. Immunol. 32:1311-1318.
Brenner (1999) Trends in Genetics 15(4) 132-133.
Browning et al., 1989, J. Immunol. 143:1859-1867.
Bickmann et al., 1981, Makromol. Chem.182:1379-1384.
Burns et al., 2002, Blood 99:4400-4405.
Busterbosch et al., 1996, Eur. J. Biochem. 237:344-349.
Butnev et al., 1998, Biology of Reproduction 58:458-469.
Byun et al., 1992, ASAIO Journal M649-M653.
Casares et al., 2001, Nature Biotech 19:142-147.
Chaffee et al., 1992, J. Clin. Invest 89:1643-1651.
Charter et al., 2000, Glycobiology 10:1049-1056.
Chern et al., 1991, Eur. J. Biochem. 202:225-229.
Chiba et al., 1995, Biochem J. 308:405-409.
Chrisey et al., 1996, Nucleic Acids Res. 24:3031-3039.
Clark, et al., 1996, J. Biol. Chem,271(36)21969-21977.
Cointe, et al., 2000, Glycobiology, 10(5):511-519.
Conradt et al., 1987, J. Biol. Chem. 262:14600-14605.
Cope et al., 1991, Molecular Microbiology 5(5):1113-1124.
Copeland, Robert A., 2000, Enzymes, Second Edition, 146-150.
Crout et al., 1998, Curr. Opin. Chem. Biol. 2:98-111.
DeFrees, 2006, Glycobiology 16:833-843.
Delgado et al., 1992, Critical Reviews in Therapeutic 9:249-304.
Delgaldo et al., 1990, Biotechnol. Appl. Biochem. 12:119-128.
Detty et al., 1982, J. Org. Chem. 47:5416-5418.
Doerks et al. (1998) Trends in Genetics 14(6): 248-250.
Douglas, et al., 1991, J. Am. Chem. Soc., 113:5095-5097.
Dunn et al., 1991, Eds. Polymeric Drugs and Drug Delivery Systems, ACS Symposium Series vol. 469, American Chemical Society, Washington D.C.
Durieux, et al., 2001, Tetrahedron Letters, 42:2297-2299.
Dwek et al., 1995, J. Anat. 187:279-292.
Eavarone et al., 2000, J. Biomed Mater. Res. 51:10-14.
Fan et al., 1997, J. Biol. Chem. 272(43):27058-27064.
Fibi et al., 1995, Cells Blood 85:1229-1236.
Fischer et al., 1998, Thrombosis Research 89:147-150.
Flynn et al., 2000, Curr. Opin. Oncol. 12:574-581.
Fritz et al., 2004, PNAS 101(43):15307-15312.
Fritz et al., 2006, J. Biol. Chem. 281(13):8613-8619.
Garnett et al., 2002, Advanced Drug Delivery Reviews 53:171-216.
Gatot, et al., 1998, J. Biol. Chem., 273(21):12870-12880.
Gilbert et al., 1996, Cytotechnology 22:211-216.
Gillis et al., 1988, Behring Inst. Mitt. Aug. 83:1-7.
Ginns, Dr. Edward, PEG Glucocerebrosidase, Internet page from www.gaucher.org.uk/peg2.prg, printed Jun. 21, 2002.
Gotschlich, Emil C., 1994, J. Exp. Med., Coden: Jemeav; ISSN: 0022-1007, 180(6):2181-90.
Grabenhorst, et al., 1993, Euro. J. Biochem., 215:189-197.
Grodberg et al., 1993, Eur. J. Biochem. 218:597-601.
Gross, H.J., 1992, Eur. J. Biochem. 203(1-2):269-275.
Hagen et al., 1999, J. Biol. Chem. 274:27867-27874.
Hagen et al., 1999, J. Biol. Chem. 274:6797-6803.
Hagen et al., 2001, J. Biol. Chem. 276:17395-17404.
Hall et al., 2001, Methods in Molecular Biology 166:139-154.
Haneda et al., 1996, Carbohydr. Res. 292:61-70.
Hang et al., 2001, J. Am. Chem. Soc. 123:1242-1243.
Harris et al., 2003, Nature Reviews Drug Discovery, 2:214-221.
Harris et al., Abstracts of Papers of the American Chemical Society, 1991, V 201, APR, p. 64-POLY, p. 154-155.
Harris, 1985, Macronol. Chem. Phys. C25: 325-373.
Hassan et al., 2000, J. Biol. Chem. 275:38197-38205.
Hayes et al., 1993, J. Biol. Chem. 268(22):16170-16178.
Hellstrom et al., 2001, Methods in Molecular Biology 166:3-16.
Hermanson et al., 1992, Immobilized Affinity Ligand Techniques, Academic Press.
Hermanson, 1996, Bioconjugate Techniques, Academic Press, San Diego.
Hermentin, et al., 1996, Glycobiology 6(2):217-230.
Hills et al., 2002, American Biotechnology Laboratory, 20(11):30.
Hink et al., 1991, Biotechnology Progress 7:9-14.
Hollister et al., 2001, Glycobiology 11:1-9.
Hounsell et al., 1996, Glycoconj. J. 13:19-26.
Ichikawa et al., 1992, J. Am. Chem. Soc. 114:9283-9298.
Ikonomou et al., 1991, In Vitro Cell. Dev. Biol.-Animal 37:549-559.
Inlow, et al., 1989, J. Tissue Culture Meth. 12:13-16.
Inoue et al., 1995, Biotechnology Annual Review 1:297-313.
Ito et al., 1993, Pure & Appl. Chem. 65(4):753-762.
Jackson et al., 1987, Anal. Biochem.165:114-127.
Jarvis et al., 1998, Curr. Opin. Biotechnol. 9:528-533.
Joppich et al., 1979, Makromol Chem. 180:1381-1384.
Joshi et al., 1990, J. Biol. Chem. 265:14518-14525.
Jung et al., 1983, Biochem. Biophys. Acta, 761:152-162.
Kalsner et al., 1995, Glycoconj. J. 12:360-370.
Kasina et al., 1998 Bioconjugate Chem., 9:108-117.
Katre et al., 1987, Proc. Natl. Acad. Sci. U.S.A. 84:1487-1491.
Keppler et al., 2001, Glycobiology 11:11R-18R.
Kitamura et al., 1990, Biochem. Biophys. Res. Commun. 28:1387-1394.
Kitamura et al., 1991, Cancer Res. 51:4310-4315.
Kodama et al., 1993, Tetrahedron Lett. 34:6419-6422.
Koeller et al., 2000, Nature Biotechnology 18: 835-841.
Koeller et al., 2001, Nature, 409:232-240.
Koide et al., 1983, Biochem Biophys. Res. Commun. 111:659-667.
Kreitmann 2001, Current Pharmaceutical Biotechnology 2:313-325.
Kuhn, et al., 1995, J. Biol. Chem. 270(49):29493-29497.
Lai et al, 1986, J. Biol. Chem. 261:3116-3121.
Lau et al. (1999) Journal of Biotechnology 75:105-115.
Lee et al., 1989, Biochemistry 28:1856-1861.
Lee-Huang et al., 1984, Proc. Natl. Acad. Sci. U.S.A. 81:2708-2712.
Leung, S., 1995, J. Immunology, 154:5919-5926.
Li et al., 2002, Trends in Pharmacological Sciences 23:206-209.
Li et al., 2002, Medicinal Research Reviews 22:225-250.
Licari P. et al., 1992, Biotechnology and Bioengineering 39(4):432-441.
Licari P. et al., 1992, Biotechnology and Bioengineering 39(9):932-944.
Liu et al., 2002, 1996, Chem. Eur. J. 2:1359-1362.
Long et al., 2006, Experimental Hematology 34:697-704.
Lord et al., 2001, Clin. Cancer Res. 7:2085-2090.
Lougheed et al., 1999, J. Biol. Chem. 274:37717-37722.
Luckow et al., 1993, Curr. Opin. Biotechnol 4:564-572.
Lund et al., 1995, FASEB J. 9:115-119.
Lund et al., 1996, J. Immunol. 157:4963-4969.
Mahal et al., 1997, Science 276:1125-1128.
Maranga et al., 2003, Biotechnology and Bioengineering 84(2):245-253.
Maras et al., 2000, Journal of Biotechnology 77:255-263.
Miller et al., 1993, Curr. Opin. Genet. Dev. 3:97-101.
Min et al., 1996, Endocr. J. 43:585-593.
Mistry et al., 1996, Lancet 348:1555-1559.
Morimoto et al., 1996, Glycoconjugate J. 13:1013-1020.
NCBI—Accession No. NCAA26095 (2 pgs.).

NCBI—Accession No. NP_058697 (3 pgs.).
NCBI—Accession No. NP_999299 (2 pgs.).
NCBI Database hits for erythropoietin protein sequences (3 pgs.).
Ngo et al. (1994) "The Protein Folding Problem and Tertiary Structure Prediction, Chapter 14: Computational Complexity Protein Structure Prediction, and the Levinthal Paradox" pp. 433-440 and 492-495.
Nilsson et al., 1984, Methods Enzymol. 104:56-69.
O'Connell et al., 1992, J. Biol. Chem. 267:25010-25018.
Oetke, et al., 2002, J. Biol. Chem 277(8):6688-6695.
Olson et al., 1999, J. Biol. Chem. 274:29889-29896.
Palacpac et al., 1999, PNAS USA 96:4692-4697.
Park et al., 1986, J. Biol Chem. 261:205-210.
Paulson et al., 1997, J. Biol. Chem. 252:8624-8628.
Plummer et al., 1995, J. Biol. Chem. 270(22):13192-13196.
PNGase-F Amidase Sequence from *F. meningosepticum* (Registry Nos. 128688-70-0).
PNGase-F Amidase Sequence from *F. meningosepticum* (Registry Nos. 128688-71-1).
Pyatak et al., 1980, Res. Commun. Chem. Pathol Pharmacol 29:113-127.
Rabouille et al., 1999, J. Cell. Biol. 112:3319-3330.
Reff et al., 2002, Cancer Control 9:152-166.
Reis et al., 1991, Biotechnology and Bioengineering 38:413-422.
Rosenthal, et al., 1994, Methods Enzymol. 235:253-285.
Sadler et al., 1982, Methods in Enzymology 83:458-514.
Sandberg et al., 2000, Seminars in Hematology 38(2):4-12.
Saneyoshi et al., 2001, Biology of Reproduction 65:1686-1690.
Saxon et al., 2000, Science 287:2007-2010.
Schlaeger, E., 1996, Cytotechnology 20:57-70.
Schwientek et al., 1994, Gene 145:299-303.
Schwientek et al., 2002, J. Biol. Chem. 277:22623-22638.
Scouten 1987, Methods in Enzymology 135:30-65.
Shah et al., 1996, J. Pharm. Sci. 85:1306-1311.
Shapiro et al., 2005, B. Biochemistry 105:518-525.
Singh et al., 1996, Chem. Commun. 1996:993-994.
Sinha et al., 1980, Infection and Immunity 29(3):914-925.
Skolnick et al. (2000) Trends in Biotech. 18(1): 34-39.
Smith et al. (1997) Nature Biotechnology 15:1222-1223.
Song et al., 2002, J. Pharmacol. Exp. Ther. 301:605-610.
Srinivasachar et al., 1989, Biochemistry 28:2501-2509.
Stephens et al., 1983, European J. of Biochem., 133(1):155-62.
Stephens et al., 1983, European J. of Biochem., 133(3):481-9.
Stephens et al., 1983, European J. of Biochem., 135(3):519-27.
Takane et al., 2000, J. Pharmacology and Experimental Therapeutics 294:746-752.
Takeda et al., 1995, Trends Biochem. Sci. 20:367-371.
Takeuchi, et al., 1990, The Journal of Biological Chemistry, 265(21): 12127-12130.
Tanner et al., 1987, Biochim. Biophys. Acta., 906:81-91.
Taylor et al., 1991, Protein Immobilization Fundamentals and Applications, Manual.
Tenno et al., 2002, J. Biol. Chem. 277(49):47088-96.
Thotakura et al., 1987, Meth Enzymol 138: 350-359.
Tsuboi et al., 2000 Archives of Biochemistry and Biophysics 374:100-106.
Tuddenham, E., 2002, Nature 419:23-24.
Udenfriend et al., 1995, Ann. Rev. Biochem. 64:563-591.
Ulloa-Aguirre et al., 1999, Role of Glycosylation in Function of Follicle-Stimulating Hormone, Endocrine 11:205-215.
Uludag et al., 2002, Biotechnol. Prog. 18:604-611.
Urdal et al, 1984, J. Chromatog, 296:171-179.
Van Berkel et al., 1996, Biochem J. 319:117-122.
Veronese et al., 1985, Appl. Biochem. Biotech. 11:141-152.
Vocadlo et al., 2000, in Carbohydrate Chemistry and Biology, vol. 2.
Vyas et al., 2001, Crit. Rev. Ther. Drug Carrier Syst. 18:1-76.
Wang et al., 1996, Tetrahedron Lett. 37:1975-1978.
Wang, M., 1998, Protein Engineering 11(12):1277-1283.
Wellhoner et al., 1991, J. Biol. Chem. 226:4309-4314.
Wells (1990) Biochemistry 29(37): 8509-8517.
Witte K. et al., 1997, J. Am. Chem. Soc. 119:2114-2118.
Woghiren et al., 1993, Bioconjugate Chem. 4:314-318.
Wong et al., 1992, Enzyme Microb.Technol. 14:866-874.
Wong et al., 1996, Biotechnology and Bioengineering 49:659-666.
Woods et al., 1989, Eur. J. Cell. Biol. 50:132-143.
Wright et al., 1998, J. Immunol. 160:3393-3402.
Wu et al., 2002, J. Drug targeting 10:239-245.
Xing et al., 1998, Biochem. J. 336:667-673.
Yamamoto et al., 1998, Carbohydr. Res. 305:415-422.
Yarema et al., 1998, J. Biol. Chem. 47:31168-31179.
Yoshida et al., 1999, Glycobiology 9:53-58.
Yoshitake et al., 1985, Biochemistry 24:3736-3750.
Zalipsky 1995, Bioconjugate Chem. 6:150-165.
Zalipsky et al., 1992, Poly (ethylene glycol) Chemistry: Biotechnical and Biomedical Applications 347-370.
Zheng et al., 1999, Biotechnology and Bioengineering 65(5):600-604.
Zhou, et al., 1994, Mol. Microbiol. 14(4):609-618.
Cohn et al., *J. Biomed. Mater. Res.*, 22: 993-1009 (1988).
Edge et al., *Anal. Biochem.*, 118: 131-137 (1981).
Harris, Poly(Ethylene Glycol) Chemistry: Biotechnical and Biomedical Applications, *Plenum Press, New York* (1992).
Harris et al., Poly(ethylene glycol): Chemistry and Biological Applications, *ACS Symposium Series No. 680, Amer. Chem. Soc.* (1997).
Hassan et al., "Control of Mucin-Type *O*-Glycosylation: *O*-Glycan Occupancy is Directed by Substrate Specificities of Polypeptide GalNAc-Transferases" in *Carbohydrates in Chem. and Biol.* (Ernst et al., eds.), Part II, vol. 3, pp. 273-292 (Wiley-VCH, 2000).
Herscovics et al., *FASEB J.*, 7: 540-550 (1993).
Keana et al., *J. Org. Chem.*, 55: 3640-3647 (1990).
Kornfeld et al., *Ann. Rev. Biochem.*, 54: 631-664 (1985).
Kukuruzinska et al., *Proc. Natl. Acad. Sci. USA*, 84: 2145-2149 (1987).
Langer, *Science*, 249: 1527-1533 (1990).
Müller et al., *J. Biol. Chem.*, 272(40): 24780-24793 (1997).
Müller, *J. Biol. Chem.*, 274(26): 18165-18172 (1999).
Pyatak et al., *Res. Commun. Chem. Pathol. Pharmacol.*, 29(1): 113-127 (1980).
Shen et al., *Biochem. Biophys. Res. Commun.*, 102(3): 1048-1054 (1981).
Sojar et al., *Arch. Biochem. Biophys.*, 259(1): 52-57 (1987).
Stemmer, *Nature*, 370: 389-391 (1994).
Stemmer, *Proc. Natl. Acad. Sci. USA*, 91: 10747-10751 (1994).
Yamada et al., *Biochem.*, 20: 4836-4842 (1981).
Younes et al., *J. Biomed. Mater. Res.*, 21: 1301-1316 (1987).
Zarling et al., *J. Immunol.*, 124(2): 913-920 (1980).
Abuchowski et al., *J. Biol. Chem.*, 252(11): 3582-3586 (1977).
Adelhorst et al., *J. Biol. Chem.*, 269(9): 6275-6278 (1994).
Amersham Pharmacia Biotech, "Hydrophobic Interaction Chromatography: Principles and Methods," 104 pp. (2000).
Barrios et al., *J. Mol. Recognit.*, 17(4):332-338 (2004).
Boime et al., *Recent Prog. Horm. Res.*, 54: 271-289 (1999).
Brockhausen et al., *Acta Anatomica*, 161: 36-78 (1998).
Brockhausen et al., *Glycoconj. J.*, 15: 595-603 (1998).
Broun et al., *Science*, 282(5392): 1315-1317 (1998).
Cantin et al., *Am. J. Respir. Cell Mol. Biol.*, 27(6): 659-665 (2002).
Copeland, "Enzymes: A Practical Introduction to Structure, Mechanism and Data Analysis" 2nd ed., Wiley-VCH, New York, pp. 146-150 (2000).
Costa et al., *J. Biol. Chem.*, 272(17): 11613-11621 (1997).
Culajay et al., *Biochem.*, 39: 7153-7158 (2000).
De Vries et al, *J. Biol. Chem.*, 270(15): 8712-8722 (1995).
Dinter et al., *Biotechnol. Lett.*, 22(1): 25-30 (2000).
Dubé et al., *J. Biol. Chem.*, 263(33): 17516-17521 (1988).
Dumas et al., *Bioorg. Med. Chem. Lett.*, 1(8): 425-428 (1991).
Fairhall et al., Endocrinology, 131(4): 1963-1969 (1992).
Feldman et al., *Proc. Natl. Acad. Sci.* USA, 102(8): 3016-3021 (2005).
Felix et al., *J. Peptide Res.*, 63: 85-90 (2004).
Francis et al., *Intl. J. Hematol.*, 68(1): 1-18 (1998).
GE et al., *J. Biol. Chem.*, 272(34): 21357-21363 (1997).
Gervais et al., *Glycobiology*, 13(3): 179-189 (2003).
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).

Grabenhorst et al., *J. Biol. Chem.*, 274(51): 36107-36116 (1999).
Gross et al., *Biochemistry*, 28(18): 7386-7392 (1989).
Hansen et al., *Biochem J.*, 308: 801-813 (1995).
Haro et al., *Biochem. Biophys. Res. Comm.*, 228(2): 549-556 (1996).
Höglund, *Med. Oncol.*, 15(4): 229-233 (1998).
Jezek et al., *J. Peptide Sci.*, 5: 46-55 (1999).
Kajihara et al., *Carbohydrate Research*, 315: 137-141 (1999).
Kaneko et al., *Cytogenet. Cell Genet.*, 86(3-4): 329-330 (1999).
Kaneko et al., *FEBS Lett.*, 452(3): 237-242 (1999).
Katre et al., *Proc. Natl. Acad. Sci.* USA, 84(6): 1487-1491 (1987).
Kawasaki et al., *Anal. Biochem.*, 285: 82-91 (2000).
Keene et al., *J. Biol. Chem.*, 264(9): 4769-4775 (1989).
Keppler et al., *Glycobiology*, 11(2): 11R-18R (2001).
Kimura et al., *Proc. Natl. Acad. Sci.* USA, 96(8): 4530-4535 (1999).
Kisselev, *Structure*, 10(1): 8-9 (2002).
Kobayashi et al., *Eur. J. Nucl Med.*, 27(9):1334-1339 (2000).
Kukowska-Latallo et al., *Genes Dev.*, 4(8): 1288-1303 (1990).
Legault et al., *J. Biol. Chem.*, 270(36): 20987-20996 (1995).
Leist et al., *Science*, 305: 239-242 (2004).
Leiter et al., *J. Biol. Chem.*, 274(31): 21830-21839 (1999).
Lewis et al., *Endocr. J.*, 47(Suppl.): S1-S8 (2000).
Lin et al., *Proc. Natl. Acad. Sci.* USA, 82: 7580-7584 (1985).
Lönnberg, *Curr. Org. Synth.*, 6(4): 400-425 (2009).
Malissard et al., *Biochem. Biophys. Res. Commun.*, 267(1): 169-173 (2000).
Meynial-Salles et al., *J. Biotechnol.*, 46(1): 1-14 (1996).
Min et al., *Endocr. J.*, 43(5): 585-593 (1996).
Mollicone et al., *Eur. J. Biochem.*, 191(1): 169-176 (1990).
Monaco et al., *Gene*, 180: 145-150 (1996).
Nagata et al., *EMBO J.*, 5(3): 575-581 (1986).
Nunez et al., *Can. J. Chem.*, 59(14): 2086-2095 (1981).
Oh-Eda et al., *J. Biol. Chem.*, 265: 11432-11435 (1990).
Palcic et al., *Carbohydr. Res.*, 190(1): 1-11 (1989).
Prati et al., *Biotech and Bioeng.*, 79(5): 580-585 (2002).
Prieels et al., *J. Biol. Chem.*, 256(20): 10456-10463 (1981).
Rasko et al., *J. Biol. Chem.*, 275(7): 4988-4994 (2000).
Rotondaro et al., *Mol. Biotech.*, 11: 117-128 (1999).
Rudikoff et al., *Proc. Natl. Acad. Sci.* USA, 79(6):1979-1983 (1982).
Sasaki et al., *J. Biol. Chem.*, 262(25): 12059-12076 (1987).
Sasaki et al., *J.Biol. Chem.*, 269: 14730-14737 (1994).
Seely et al., *J. Chromatog.*, 908: 235-241 (2001).
Seffernick et al., *J. Bacteriol.*, 183(8): 2405-2410 (2001).
Shinkai et al., *Prot. Exp. Purif.*, 10: 379-385 (1997).
Sinclair et al., *J. Pharm. Sci.*, 94: 1626-1635 (2005).
Snider et al., *J. Chromatogr.*, A 599(1-2): 141-155 (1992).
Srinivasachar et al., *Biochemistry*, 28(6): 2501-2509 (1989).
Staudacher, *Trends Glycosci. Glycotechnol.*, 8(44): 391-408 (1996).
Strausberg et al., *Proc Natl Acad Sci* USA, 99(26): 16899-16903 (2002).
Trottein et al., *Mol. Biochem. Parasitol.*, 107(2): 279-287 (2000).
Tsunoda et al., *J. Pharmacol Exp. Ther.*, 209(1): 368-372 (1999).
Urdal et al, *J. Chromatogr.*, 296: 171-179 (1984).
Van Tetering et al., *FEBS Lett.*, 461(3): 311-314 (1999).
Vitetta et al., *Science*, 313: 308-309 (2006).
Wang et al., *Glycobiology*, 6(8): 837-842 (1996).
Wang et al., *Microbiol.*, 145(Pt. 11): 3245-3253 (1999).
Weston et al., *J. Biol. Chem.*, 267(34): 24575-24584 (1992).
White et al., *J. Biol. Chem.*, 270(41): 24156-24165 (1995).
Wishart et al., *J. Biol. Chem.*, 270(45): 26782-26785 (1995).
Witkowski et al., *Biochemistry*, 38(36): 11643-11650 (1999).
Witte et al., *J. Am. Chem. Soc.*, 119(9): 2114-2118 (1997).
Witte et al., *Cancer and Metastasis Rev.*, 17: 155-161 (1998).
Wu et al., *J. Drug Target.*, 10(3): 239-245 (2002).

* cited by examiner

GH-N (O-Glycosylation)

ptt f pttp lsrlfdnam lrahrlhqla fdtyqefeea yipkeqkysf lqn ptts lcf sesi ptpttt
eetqqksnle llrisllliq swlepvqflr svfanslvyg asdsnvydll kdleegiqtl mgrledgs
pttt qifk ttts kfdtnshndd allknyglly cfrkdmdkve tflrivqcrs vegscgf

GH-N (pituitary)

fpti plsrlfdnam lrahrlhqla fdtyqefeea yipkeqkysf lqnpqtslcf sesiptpsnr
eetqqksnle llrisllliq swlepvqflr svfanslvyg asdsnvydll kdleegiqtl mgrledgspr
tgqifkqtys kfdtnshndd allknyglly cfrkdmdkve tflrivqcrs vegscgf

Fig. 6

```
                                  50
hGH O-linked 134   (1)   ---FPTIPLSRLFDNAMLRAHRLHQLAFDTYQEFEEAYIPKEQKYSFLQN
hGH O-linked 5'    (1)   PTTFPTIPLSRLFDNAMLRAHRLHQLAFDTYQEFEEAYIPKEQKYSFLQN
hGH-N1 mature      (1)   ---FPTIPLSRLFDNAMLRAHRLHQLAFDTYQEFEEAYIPKEQKYSFLQN
Consensus          (1)      FPTIPLSRLFDNAMLRAHRLHQLAFDTYQEFEEAYIP KEQKYSFLQN
                         51                                             100
hGH O-linked 134   (48)  PQTSLCFSESIPTPSNREETQQKSNLELLRISLLLIQSWLEPVQFLRSVF
hGH O-linked 5'    (51)  PQTSLCFSESIPTPSNREETQQKSNLELLRISLLLIQSWLEPVQFLRSVF
hGH-N1 mature      (48)  PQTSLCFSESIPTPSNREETQQKSNLELLRISLLLIQSWLEPVQFLRSVF
Consensus          (51)  PQTSLCFSESIPTPSNREETQQKSNLELLRISLLLIQSWL EPVQFLRSVF
                         101                                            150
hGH O-linked 134   (98)  ANSLVYGASDSNVYDLLKDLEEGIQTLMGRLEDGSPTTTQIFKQTYSKFD
hGH O-linked 5'    (101) ANSLVYGASDSNVYDLLKDLEEGIQTLMGRLEDGSPRTGQIFKQTYSKFD
hGH-N1 mature      (98)  ANSLVYGASDSNVYDLLKDLEEGIQTLMGRLEDGSPRTGQIFKQTYSKFD
Consensus          (101) ANSLVYGASDSNVYDLLKDLEEGIQTLMGRLEDGSPRTGQ IFKQTYSKFD
                         151                                      194
hGH O-linked 134   (148) TNSHNDDALLKNYGLLYCFRKDMDKVETFLRIVQCRSVEGSCGF
hGH O-linked 5'    (151) TNSHNDDALLKNYGLLYCFRKDMDKVETFLRIVQCRSVEGSCGF
hGH-N1 mature      (148) TNSHNDDALLKNYGLLYCFRKDMDKVETFLRIVQCRSVEGSCGF
Consensus          (151) TNSHNDDALLKNYGLLYCFRKDMDKVETFLRIVQCRSVEG SCGF
```

Fig. 7

```
                                  50
hGH O-linked 134    (1)   ---FPTIPLSRLFDNAMLRAHRLHQLAFDTYQEFEEAYIPKEQKYSFLQN
hGH O-linked 5'     (1)   -MVTPTIPLSRLFDNAMLRAHRLHQLAFDTYQEFEEAYIPKEQKYSFLQN
hGH-N1 mature       (1)   ---FPTIPLSRLFDNAMLRAHRLHQLAFDTYQEFEEAYIPKEQKYSFLQN
Consensus           (1)      FPTIPLSRLFDNAMLRAHRLHQLAFDTYQEFEEAYIP KEQKYSFLQN
                          51                                              100
hGH O-linked 134    (48)  PQTSLCFSESIPTPSNREETQQKSNLELLRISLLLIQSWLEPVQFLRSVF
hGH O-linked 5'     (51)  PQTSLCFSESIPTPSNREETQQKSNLELLRISLLLIQSWLEPVQFLRSVF
hGH-N1 mature       (48)  PQTSLCFSESIPTPSNREETQQKSNLELLRISLLLIQSWLEPVQFLRSVF
Consensus           (51)  PQTSLCFSESIPTPSNREETQQKSNLELLRISLLLIQSWL EPVQFLRSVF
                          101                                             150
hGH O-linked 134    (98)  ANSLVYGASDSNVYDLLKDLEEGIQTLMGRLEDGSPTTGQIFKQTYSKFD
hGH O-linked 5'     (101) ANSLVYGASDSNVYDLLKDLEEGIQTLMGRLEDGSPRTGQIFKQTYSKFD
hGH-N1 mature       (98)  ANSLVYGASDSNVYDLLKDLEEGIQTLMGRLEDGSPRTGQIFKQTYSKFD
Consensus           (101) ANSLVYGASDSNVYDLLKDLEEGIQTLMGRLEDGSPRTGQ IFKQTYSKFD
                          151                                     194
hGH O-linked 134    (148) TNSHNDDALLKNYGLLYCFRKDMDKVETFLRIVQCRSVEGSCGF
hGH O-linked 5'     (151) TNSHNDDALLKNYGLLYCFRKDMDKVETFLRIVQCRSVEGSCGF
hGH-N1 mature       (148) TNSHNDDALLKNYGLLYCFRKDMDKVETFLRIVQCRSVEGSCGF
Consensus           (151) TNSHNDDALLKNYGLLYCFRKDMDKVETFLRIVQCRSVEG SCGF
```

Fig. 8

FPTIPLSRLFDNAMLRAHRLHQLAFDTYQEFEEAYIPKEQKYSFLQNPQTSLCFSE
SIPTPSNREETQQKSNLELLRISLLLIQSWLEPVQFLRSVFANSLVYGASDSNVYDL
LKDLEEGIQTLMGRLEDGSPRTGQIFKQTYSKFDTNSHNDDALLKNYGLLYCFRK
DMDKVETFLRIVQCRSVEGSCGF

FIG. 9A

FPTIPLSRLFDNAMLRARRLYQLAYDTYQEFEEAYILKEQKYSFLQNPQTSLCFSE
SIPTPSNRVKTQQKSNLELLRISLLLIQSWLEPVQLLRSVFANSLVYGASDSNVYR
HLKDLEEGIQTLMWRLEDGSPRTGQIFNQSYSKFDTKSHNDDALLKNYGLLYCF
RKDMDKVETFLRIVQCRSVEGSCGF

FIG. 9B

FPTIPLSRLFDNAMLRAHRLHQLAFDTYQEFEEAYIPKEQKYSFLQNPQTSLCFSE
SIPTPSNREETQQKSNLELLRISLLLIQSWLEPVQFLRSVFANSLVYGASDSNVYDL
LKDLEEGIQTLMGRLEDGSPTTTQIFKQTYSKFDTNSHNDDALLKNYGLLYCFRK
DMDKVETFLRIVQCRSVEGSCGF

FIG. 9C

PTTFPTIPLSRLFDNAMLRAHRLHQLAFDTYQEFEEAYIPKEQKYSFLQNPQTSLC
FSESIPTPSNREETQQKSNLELLRISLLLIQSWLEPVQFLRSVFANSLVYGASDSNV
YDLLKDLEEGIQTLMGRLEDGSPRTGQIFKQTYSKFDTNSHNDDALLKNYGLLY
CFRKDMDKVETFLRIVQCRSVEGSCGF

FIG. 9D

FPTIPLSRLFDNAMLRAHRLHQLAFDTYQEFEEAYIPKEQKYSFLQNPQTSLCFSE
SIPTPSNREETQQKSNLELLRISLLLIQSWLEPVQFLRSVFANSLVYGASDSNVYDL
LKDLEEGIQTLMGRLEDGSPTTGQIFKQTYSKFDTNSHNDDALLKNYGLLYCFRK
DMDKVETFLRIVQCRSVEGSCGF

FIG. 9E

MVTPTIPLSRLFDNAMLRAHRLHQLAFDTYQEFEEAYIPKEQKYSFLQNPQTSLCF
SESIPTPSNREETQQKSNLELLRISLLLIQSWLEPVQFLRSVFANSLVYGASDSNVY
DLLKDLEEGIQTLMGRLEDGSPRTGQIFKQTYSKFDTNSHNDDALLKNYGLLYCF
RKDMDKVETFLRIVQCRSVEGSCGF

FIG. 9F

MVTPTIPLSRLFDNAMLRAHRLHQLAFDTYQEFEEAYIPKEQKYSFLQNPQTSLCF
SESIPTPSNREETQQKSNLELLRISLLLIQSWLEPVQFLRSVFANSLVYGASDSNVY
DLLKDLEEGIQTLMGRLEDGSPRTGQIFKQTYSKFDTNSHNDDALLKNYGLLYCF
RKDMDKVETFLRIVQCRSVEGSCGF

FIG. 9G

MFPTIPLSRLFDNAMLRAHRLHQLAFDTYQEFEEAYIPKEQKYSFLQNPQTSLCFS
ESIPTPSNREETQQKSNLELLRISLLLIQSWLEPVQFLRSVFANSLVYGASDSNVYD
LLKDLEEGIQTLMGRLEDGSPTVGQIFKQTYSKFDTNSHNDDALLKNYGLLYCFR
KDMDKVETFLRIVQCRSVEGSCGF

FIG. 9H

MFPTIPLSRLFDNAMLRAHRLHQLAFDTYQEFEEAYIPKEQKYSFLQNPQTSLCFS
ESIPTPSNREETQQKSNLELLRISLLLIQSWLEPVQFLRSVFANSLVYGASDSNVYD
LLKDLEEGIQTLMGRLEDGSPTTTQIFKQTYSKFDTNSHNDDALLKNYGLLYCFR
KDMDKVETFLRIVQCRSVEGSCGF

FIG. 9I

COMPOSITIONS AND METHODS FOR THE PREPARATION OF HUMAN GROWTH HORMONE GLYCOSYLATION MUTANTS

CROSS-REFERENCES TO RELATED APPLICATIONS

The present application is a U.S. national phase application of PCT Application No. PCT/US2004/014254, filed May 7, 2004, and claims priority to U.S. Provisional Patent Application No. 60/469,114, filed May 9, 2003, U.S. Provisional Patent Application No. 60/494,751, filed Aug. 13, 2003, U.S. Provisional Patent Application No. 60/495,076, filed Aug. 14, 2003, U.S. Provisional Patent Application No. 60/535,290, filed Jan. 8, 2003 each of which is incorporated herein by reference in its entirety for all purposes.

BACKGROUND OF THE INVENTION

Human growth Hormone (hGH) and agonist variants thereof are members of a family of recombinant proteins, described in U.S. Pat. No. 4,658,021 and U.S. Pat. No. 5,633,352. Their recombinant production and methods of use are detailed in U.S. Pat. Nos. 4,342,832, 4,601,980; U.S. Pat. No. 4,898,830; U.S. Pat. No. 5,424,199; and U.S. Pat. No. 5,795,745. Human growth hormone participates in various aspects of the regulation of normal human growth and development. Through interaction with its receptors, this 22 kDa pituitary hormone modulates a multitude of biological effects, such as linear growth (somatogenesis), lactation, activation of macrophages, and insulin-like and diabetogenic effects. Chawla, *Annu. Rev. Med.,* 34: 519 (1983); Edwards et al., *Science,* 239: 769 (1988); Isaksson et al., *Annu. Rev. Physiol.,* 47: 483 (1985); Thorner and Vance, *J. Clin. Invest.,* 82: 745 (1988); Hughes and Friesen, *Annu. Rev. Physiol.,* 47: 469 (1985).

The administration of glycosylated and non-glycosylated peptides for engendering a particular physiological response is well known in the medicinal arts. Both purified and recombinant hGH have been used for treating conditions and diseases due to hGH deficiency, e.g., dwarfism in children. A principal factor that has limited the use of therapeutic peptides is the immunogenic nature of most peptides. In a patient, an immunogenic response to an administered peptide can neutralize the peptide and/or lead to the development of an allergic response in the patient. Other deficiencies of therapeutic glycopeptides include suboptimal potency and rapid clearance rates. The problems inherent in peptide therapeutics are recognized in the art, and various methods of eliminating the problems have been investigated. For example, to provide soluble peptide therapeutics, synthetic polymers have been attached to the peptide backbone.

Poly(ethyleneglycol) ("PEG") is an exemplary polymer that has been conjugated to polypeptides. The use of to PEG to derivatize peptide therapeutics has been demonstrated to reduce the immunogenicity of the peptides. For example, U.S. Pat. No. 4,179,337 (Davis et al.) concerns non-immunogenic polypeptides, such as enzymes and peptide hormones coupled to polyethylene glycol (PEG) or polypropylene glycol. Between 10 and 100 moles of polymer are used per mole polypeptide and at least 15% of the physiological activity is maintained. In addition, the clearance time in circulation is prolonged due to the increased size of the PEG-conjugate of the polypeptides in question. The methods disclosed by Davis et al. are chemical PEG-ylation methods.

The chemical modification of peptides, frequently results in an undesirable loss of peptide activity, which is attributable to the non-selective nature of the chemistries utilized to modify the peptide. For example, when the modifying group is a water-soluble peptide, e.g., PEG, the principal mode of attachment of PEG, and its derivatives, to peptides is a non-specific bonding through a peptide amino acid residue. Studies of conjugates of water-soluble polymers and interleukin-2 (Fisher et al., *Br. J. Haematol.,* 82: 654 (1992)), granulocyte colony stimulating factor (Satake-Ishikawa et al., *Cell Struct. Funct.,* 17: 157 (1992)), tumor necrosis factor (Tsutsumi et al., *Br. J. Cancer,* 71: 963 (1996)) and human growth hormone (Clark, et al., *J. Biol. Chem.,* 271:21969 (1996)) have revealed that chemical PEGylation of these proteins decreases the in vivo receptor binding activity of the peptides.

In many chemical PEGylation methods, poly(ethyleneglycol) is added in an essentially random, non-specific manner to reactive residues on a peptide backbone. For the production of therapeutic peptides, it is clearly desirable to utilize a derivitization strategy that results in the formation of a specifically labeled, readily characterizable, essentially homogeneous product. A promising route to preparing specifically labeled peptides is through the use of enzymes, such as glycosyltransferases to append a modified sugar moiety onto a peptide.

Enzyme-based syntheses have the advantages of regioselectivity and stereoselectivity. Moreover, enzymatic syntheses are performed using unprotected substrates. Three principal classes of enzymes are used in the synthesis of carbohydrates, glycosyltransferases (e.g., sialyltransferases, oligosaccharyltransferases, N-acetylglucosaminyltransferases), and glycosidases. The glycosidases are further classified as exoglycosidases (e.g., β-mannosidase, β-glucosidase), and endoglycosidases (e.g., Endo-A, Endo-M). Each of these classes of enzymes has been successfully used synthetically to prepare carbohydrates. For a general review, see, Crout et al., *Curr. Opin. Chem. Biol.* 2: 98-111 (1998).

Glycosyltransferases modify the oligosaccharide structures on glycopeptides, producing specific products with good stereochemical and regiochemical control. Glycosyltransferases are used to prepare oligosaccharides and to modify terminal N- and O-linked carbohydrate structures, particularly on glycopeptides produced in mammalian cells. For example, the terminal oligosaccharides of glycopeptides have been completely sialylated and/or fucosylated to provide more consistent sugar structures, which improves glycopeptide pharmacodynamics and a variety of other biological properties. For example, β-1,4-galactosyltransferase was used to synthesize lactosamine, an illustration of the utility of glycosyltransferases in the synthesis of carbohydrates (see, e.g., Wong et al., *J. Org. Chem.* 47: 5416-5418 (1982)). Moreover, numerous synthetic procedures have made use of α-sialyltransferases to transfer sialic acid from cytidine-5'-monophospho-N-acetylneuraminic acid to the 3-OH or 6-OH of galactose (see, e.g., Kevin et al., *Chem. Eur. J.* 2: 1359-1362 (1996)). Fucosyltransferases are used in synthetic pathways to transfer a fucose unit from guanosine-5'-diphosphofucose to a specific hydroxyl of a saccharide acceptor. For example, Ichikawa prepared sialyl Lewis-X by a method that involves the fucosylation of sialylated lactosamine with a cloned fucosyltransferase (Ichikawa et al., *J. Am. Chem. Soc.* 114: 9283-9298 (1992)). For a discussion of recent advances in glycoconjugate synthesis for therapeutic use see, Koeller et al., *Nature Biotechnology* 18: 835-841 (2000). See also, U.S. Pat. Nos. 5,876,980; 6,030,815; 5,728,554; 5,922,577; and WO/9831826.

Glycosidases can also be used to prepare saccharides. Glycosidases normally catalyze the hydrolysis of a glycosidic bond. Under appropriate conditions, however, they can be used to form this linkage. Most glycosidases used for carbohydrate synthesis are exoglycosidases; the glycosyl transfer occurs at the non-reducing terminus of the substrate. The glycosidase takes up a glycosyl donor in a glycosyl-enzyme intermediate that is either intercepted by water to give the hydrolysis product, or by an acceptor, to give a new glycoside or oligosaccharide. An exemplary pathway using an exoglycosidase is the synthesis of the core trisaccharide of all N-linked glycopeptides, including the difficult β-mannoside linkage, which was formed by the action of β-mannosidase (Singh et al., *Chem. Commun.* 993-994 (1996)).

In another exemplary application of the use of a glycosidase to form a glycosidic linkage, a mutant glycosidase has been prepared in which the normal nucleophilic amino acid within the active site is changed to a non-nucleophilic amino acid. The mutant enzymes do not hydrolyze glycosidic linkages, but can still form them. The mutant glycosidases are used to prepare oligosaccharides using an α-glycosyl fluoride donor and a glycoside acceptor molecule (Withers et al., U.S. Pat. No. 5,716,812). Although the mutant glycosidases are useful for forming free oligosaccharides, it has yet to be demonstrated that such enzymes are capable of appending glycosyl donors onto glycosylated or non-glycosylated peptides, nor have these enzymes been used with unactivated glycosyl donors.

Although their use is less common than that of the exoglycosidases, endoglycosidases are also utilized to prepare carbohydrates. Methods based on the use of endoglycosidases have the advantage that an oligosaccharide, rather than a monosaccharide, is transferred. Oligosaccharide fragments have been added to substrates using endo-β-N-acetylglucosamines such as endo-F, endo-M (Wang et al., *Tetrahedron Lett.* 37: 1975-1978); and Haneda et al., *Carbohydr. Res.* 292: 61-70 (1996)).

In addition to their use in preparing carbohydrates, the enzymes discussed above are applied to the synthesis of glycopeptides as well. The synthesis of a homogenous glycoform of ribonuclease B has been published (Witte K. et al., *J. Am. Chem. Soc.* 119: 2114-2118 (1997)). The high mannose core of ribonuclease B was cleaved by treating the glycopeptide with endoglycosidase H. The cleavage occurred specifically between the two core GlcNAc residues. The tetrasaccharide sialyl Lewis X was then enzymatically rebuilt on the remaining GlcNAc anchor site on the now homogenous protein by the sequential use of β-1,4-galactosyltransferase, α-2,3-sialyltransferase and α-1,3-fucosyltransferase V. Each enzymatically catalyzed step proceeded in excellent yield.

Methods combining both chemical and enzymatic synthetic elements are also known. For example, Yamamoto and coworkers (*Carbohydr. Res.* 305: 415-422 (1998)) reported the chemoenzymatic synthesis of the glycopeptide, glycosylated Peptide T, using an endoglyosidase. The N-acetylglucosaminyl peptide was synthesized by purely chemical means. The peptide was subsequently enzymatically elaborated with the oligosaccharide of human transferrin glycopeptide. The saccharide portion was added to the peptide by treating it with an endo-β-N-acetylglucosaminidase. The resulting glycosylated peptide was highly stable and resistant to proteolysis when compared to the peptide T and N-acetylglucosaminyl peptide T.

The use of glycosyltransferases to modify peptide structure with reporter groups has been explored. For example, Brossmer et al. (U.S. Pat. No. 5,405,753) discloses the formation of a fluorescent-labeled cytidine monophosphate ("CMP") derivative of sialic acid and the use of the fluorescent glycoside in an assay for sialyl transferase activity and for the fluorescent-labeling of cell surfaces, glycoproteins and gangliosides. Gross et al. (*Analyt. Biochem.* 186: 127 (1990)) describe a similar assay. Bean et al. (U.S. Pat. No. 5,432,059) discloses an assay for glycosylation deficiency disorders utilizing reglycosylation of a deficiently glycosylated protein. The deficient protein is reglycosylated with a fluorescent-labeled CMP glycoside. Each of the fluorescent sialic acid derivatives is substituted with the fluorescent moiety at either the 9-position or at the amine that is normally acetylated in sialic acid. The methods using the fluorescent sialic acid derivatives are assays for the presence of glycosyltransferases or for non-glycosylated or improperly glycosylated glycoproteins. The assays are conducted on small amounts of enzyme or glycoprotein in a sample of biological origin. The enzymatic derivatization of a glycosylated or non-glycosylated peptide on a preparative or industrial scale using a modified sialic acid has not been disclosed or suggested.

Enzymatic methods have also been used to activate glycosyl residues on a glycopeptide towards subsequent chemical elaboration. The glycosyl residues are typically activated using galactose oxidase, which converts a terminal galactose residue to the corresponding aldehyde. The aldehyde is subsequently coupled to an amine-containing modifying group. For example, Casares et al. (*Nature Biotech.* 19: 142 (2001)) have attached doxorubicin to the oxidized galactose residues of a recombinant MHCII-peptide chimera.

Glycosyl residues have also been modified to bear ketone groups. For example, Mahal and co-workers (*Science* 276: 1125 (1997)) have prepared N-levulinoyl mannosamine ("ManLev"), which has a ketone functionality at the position normally occupied by the acetyl group in the natural substrate. Cells were treated with the ManLev, thereby incorporating a ketone group onto the cell surface. See, also Saxon et al., *Science* 287: 2007 (2000); Hang et al., *J. Am. Chem. Soc.* 123: 1242 (2001); Yarema et al., *J. Biol. Chem.* 273: 31168 (1998); and Charter et al., *Glycobiology* 10: 1049 (2000).

Carbohydrates are attached to glycopeptides in several ways of which N-linked to asparagine and mucin-type O-linked to serine and threonine are the most relevant for recombinant glycoprotein therapeuctics. A determining factor for initiation of glycosylation of a protein is the primary sequence context, although clearly other factors including protein region and conformation play roles. N-linked glycosylation occurs at the consensus sequence NXS/T, where X can be any amino acid but proline.

The methods discussed above do not provide access to industrially relevant quantities of modified peptides that substantially retain the pharmacological activity of their unmodified analogues. Moreover, the methods do not allow for the site-specific conjugation of a modified sugar to a peptide or glycopeptide. Nor do the methods provide a means to prepare modified peptides that are glycosylated or glycoconjugated at non-natural sites.

The present invention answers these needs by providing hGH mutants that contain newly introduced N-linked or O-linked glycosylation sites, providing flexibility in glycosylation and/or glycopegylation of these recombinant hGH mutants. Moreover, the invention provides an industrially practical method for the modification of N- or O-linked mutant hGH peptides with modifying groups such as water-soluble polymers, therapeutic moieties, biomolecules, and the like. Of particular interest are methods in which the modified mutant hGH has improved properties, which enhance its use as a therapeutic or diagnostic agent.

BRIEF SUMMARY OF THE INVENTION

In one aspect, the present invention provides an isolated nucleic acid comprising a polynucleotide sequence encoding a mutant human growth hormone. The mutant human growth hormone comprises an N-linked or O-linked glycosylation site that is not present in wild-type human growth hormone. In some embodiments, the wild-type human growth hormone has the amino acid sequence of SEQ ID NO:1 or SEQ ID NO:2. In some preferred embodiments, the mutant human growth hormone includes the amino acid sequence of SEQ ID NO:3, 4, 5, 6, 7, 8, or 9.

In another aspect, the present invention provides an expression cassette or a cell that comprises a nucleic acid, e.g., an isolated nucleic acid, including a polynucleotide sequence encoding a mutant human growth hormone. The mutant human growth hormone includes an N-linked or O-linked glycosylation site that is not present in the wild-type human growth hormone.

In another aspect, the present invention provides a mutant human growth hormone, that includes an N-linked or O-linked glycosylation site that is not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, or 9.

In another aspect, the present invention provides a method for making a mutant human growth hormone that includes an N-linked or O-linked glycosylation site that is not present in the wild-type human growth hormone. This method includes the steps of recombinantly producing the mutant human growth hormone, and glycosylating the mutant human growth hormone at the new glycosylation site. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, or 9.

In still a further aspect, the present invention provides a pharmaceutical composition having a therapeutically effective amount of a mutant human growth hormone that includes an N-linked or O-linked glycosylation site not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, or 9.

In another aspect, the present invention provides a method for treating human growth hormone deficiency in a subject. The method includes administering to the subject an amount of a mutant human growth hormone effective to treat or ameliorate the growth hormone deficiency. The mutant human growth hormone used in this method comprises an N-linked or O-linked glycosylation site that does not exist in the corresponding wild-type human growth hormone. In some embodiments, the corresponding wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, or 9.

In each of the aspects described above, the mutant human growth hormone is optionally conjugates to one or more modifying group, preferably via glycoconjugation giving rise to a glycosyl linking group between the glycosylation site and the modifying group. An exemplary modifying group is poly(ethylene glycol).

BRIEF DESCRIPTION OF THE DRAWINGS

FIG. 6 are the amino acid sequences of six (6) different O-linked glycosylation sites that may be introduced into pituitary derived hGH (GH-N). The wild-type amino acid sequence for GH-N is also shown for comparison. The arrows indicate the threonine residue of the GH-N glycan mutant on which O-linked glycosylation will occur.

FIG. 7 are the amino acid sequences of hGH O-linked GH-N mutant 134(rtg)→ttt and hGH O-linked 5' GH-N mutant in which amino acids-3 to -1 (ptt) are inserted at the amino terminus, resulting in a 194 amino acid hGH polypeptide.

FIG. 8 are the amino acid sequences of hGH O-linked GH-N mutant 134(rtg)→ttg and hGH O-linked 5' GH-N mutant in which amino acids-3 to -1 (mvt) are inserted at the amino terminus, resulting in a 194 amino acid hGH polypeptide.

FIG. 9A depicts the amino acid sequence of mature human growth hormone (GH-N) (SEQ ID NO:1). FIG. 9B depicts the amino acid sequence of mature human growth hormone (GH-V) (SEQ ID NO:2). FIG. 9C depicts the amino acid sequence of human growth hormone mutant 1 (SEQ ID NO:3). FIG. 9D depicts the amino acid sequence of human growth hormone mutant 2 (SEQ ID NO:4). FIG. 9E depicts the amino acid sequence of human growth hormone mutant 3 (SEQ ID NO:5). FIG. 9F depicts the amino acid sequence of human growth hormone mutant 4 (SEQ ID NO:6). FIG. 9G depicts the amino acid sequence of human growth hormone mutant 5 (SEQ ID NO:7). FIG. 9H depicts the amino acid sequence of human growth hormone mutant 6 (SEQ ID NO:8). FIG. 9I depicts the amino acid sequence of human growth hormone mutant 7 (SEQ ID NO:9).

DETAILED DESCRIPTION OF THE INVENTION

Definitions

Figure 1:
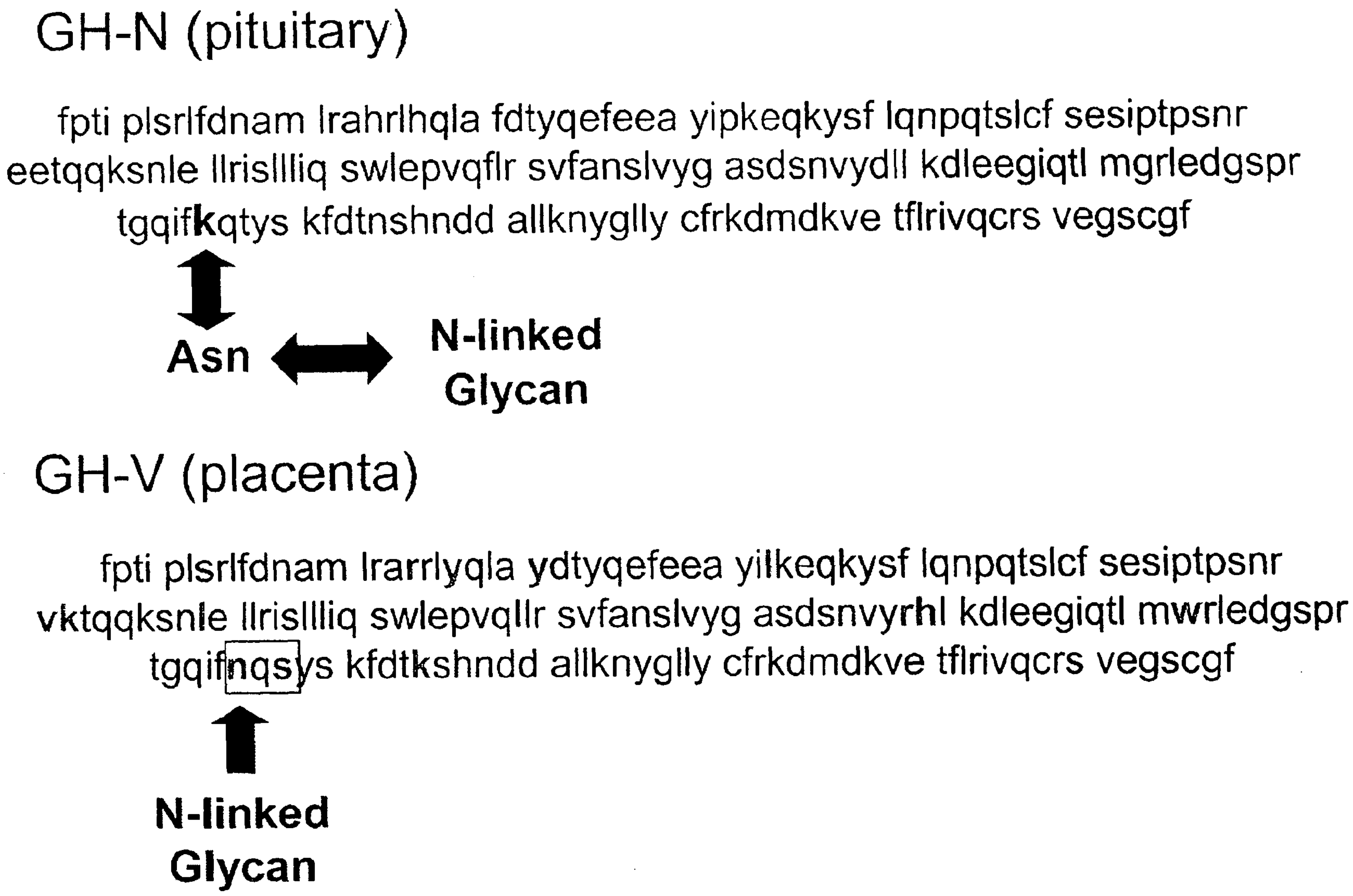
FIG. 1 is the amino acid sequences of GH-N (pituitary derived hGH) and GH-V (placental derived hGH). The arrows indicate the amino acid position for a mutational introduction of (GH-N) or a naturally existing (GH-V) N-linked glycosylation site.

The term “nucleic acid” or “polynucleotide” refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol.*

*Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

"Proximate a proline residue," as used herein refers to an amino acid that is less than about 10 amino acids removed from a proline residue, preferably, less than about 9, 8, 7, 6 or 5 amino acids removed from a proline residue, more preferably, less than about 4, 3, 2 or 1 residues removed from a proline residue. The amino acid "proximate a proline residue" may be on the C- or N-terminal side of the proline residue.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "mutating" or "mutation," as used in the context of introducing additional N- or O-linked glycosylation site(s) into a wild-type human growth hormone, refers to the deletion, insertion, or substitution of any nucleotide or amino acid residue, by chemical, enzymatic, or any other means, in a polynucleotide sequence encoding a wild-type human growth hormone or the amino acid sequence of a wild-type human growth hormone, respectively, such that the amino acid sequence of the resulting human growth hormone comprises at least one N- or O-linked glycosylation site that does not exist in the corresponding wild-type human growth hormone. In the case of amino acid substitution, both conservative and non-conservative substitutions may be used to create a hGH mutant that contains a new N- or O-linked glycosylation site.

The site for a mutation introducing a new N- or O-linked glycosylation site may be located anywhere in the polypeptide. Exemplary amino acid sequences for human growth hormone mutants are depicted in SEQ ID NOs:3-9. A "mutant human growth hormone" of this invention thus comprises at least one mutated amino acid residue. On the other hand, the wild-type human growth hormone whose coding sequence is modified to generate a mutant human growth hormone is referred to in this application as "the corresponding wild-type human growth hormone." For example, SEQ ID NO:1 is the amino acid sequence of the corresponding wild-type human growth hormone for mutant human growth hormones having the amino acid sequences of SEQ ID NOs:3-9.

The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of pharmaceutical Compounding* (1999); and Pickar, *Dosage Calculations* (1999)).

As used herein, the term "modified sugar," refers to a naturally- or non-naturally-occurring carbohydrate that is enzymatically added onto an amino acid or a glycosyl residue of a peptide in a process of the invention. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, water-soluble polymers, therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol), e.g., m-PEG. Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(—PEG—OH) .sub.m in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly($\alpha$-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The "area under the curve" or "AUC", as used herein in the context of administering a peptide drug to a patient, is defined as total area under the curve that describes the concentration of drug in systemic circulation in the patient as a function of time from zero to infinity.

The term "half-life" or "t½", as used herein in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. For some glycosylated peptides, rapid beta phase clearance may be mediated via receptors on macrophages, or endothelial cells that recognize terminal galactose, N-acetylgalactosamine, N-acetylglucosamine, mannose, or fucose. Slower beta phase clearance may occur via renal glomerular filtration for molecules with an effective radius $<2$ nm (approximately 68 kD) and/or specific or non-specific uptake and metabolism in tissues. GlycoPEGylation may cap terminal sugars (e.g., galactose or N-acetylgalactosamine) and thereby block rapid alpha phase clearance via receptors that recognize these sugars. It may also confer a larger effective radius and thereby decrease the volume of distribution and tissue uptake, thereby prolonging the late beta phase. Thus, the precise impact of glycoPEGylation on alpha phase and beta phase half-lives will vary depending upon the size, state of glycosylation, and other parameters, as is well known in the art. Further explanation of "half-life" is found in Pharmaceutical Biotechnology (1997, DFA Crommelin and RD Sindelar, eds., Harwood Publishers, Amsterdam, pp 101-120).

The term "glycoconjugation," as used herein, refers to the enzymatically mediated conjugation of a modified sugar species to an amino acid or glycosyl residue of a polypeptide, e.g., a mutant human growth hormone of the present invention. A subgenus of "glycoconjugation" is "glycol-PEGylation," in which the modifying group of the modified sugar is poly(ethylene glycol), and alkyl derivative (e.g., m-PEG) or reactive derivative (e.g., H2N-PEG, HOOC-PEG) thereof.

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g., multivalent agents. Therapeutic moiety also includes proteins and constructs that include proteins. Exemplary proteins include, but are not limited to, Erythropoietin (EPO), Granulocyte Colony Stimulating Factor (GCSF), Granulocyte Macrophage Colony Stimulating Factor (GMCSF), Interferon (e.g., Interferon-α, -β, -γ), Interleukin (e.g., Interleukin II), serum proteins (e.g., Factors VII, VIIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, interferons and radioactive agents. Also encompassed within the scope of the term "anti-tumor drug," are conjugates of peptides with anti-tumor activity, e.g. TNF-α. Conjugates include, but are not limited to those formed between a therapeutic protein and a glycoprotein of the invention. A representative conjugate is that formed between PSGL-1 and TNF-α.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetracaine, lidocaine, propranolol, and puromycin and analogs or homologs thereof. Other toxins include, for example, ricin, CC-1065 and analogues, the duocarmycins. Still other toxins include diptheria toxin, and snake venom (e.g., cobra venom).

As used herein, "a radioactive agent" includes any radioisotope that is effective in diagnosing or destroying a tumor. Examples include, but are not limited to, indium-111, cobalt-60. Additionally, naturally occurring radioactive elements such as uranium, radium, and thorium, which typically represent mixtures of radioisotopes, are suitable examples of a radioactive agent. The metal ions are typically chelated with an organic chelating moiety.

Many useful chelating groups, crown ethers, cryptands and the like are known in the art and can be incorporated into the compounds of the invention (e.g., EDTA, DTPA, DOTA, NTA, HDTA, etc. and their phosphonate analogs such as DTPP, EDTP, HDTP, NTP, etc). See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., *Bioconjugate Chem.*, 9: 108-117 (1998); Song et al., *Bioconjugate Chem.*, 8: 249-255 (1997).

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering," means oral administration, inhalation, administration as a suppository, topical contact, intravenous, intraperitoneal, intramuscular, intralesional, intranasal or subcutaneous administration, or the implantation of a slow-release device e.g., a mini-osmotic pump, to the subject. Adminsitration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "isolated" refers to a material that is substantially or essentially free from components, which are used to produce the material. For peptide conjugates of the invention, the term "isolated" refers to material that is substantially or essentially free from components, which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. It will be understood by one of skill in the art, that the starting material may contain glycosylated acceptor moieties (e.g., fucosylated Galβ-1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Other objects, aspects and advantages of the invention will be apparent from the detailed description that follows.

Abbreviations

PEG, poly(ethyleneglycol); m-PEG, methoxy-poly(ethylene glycol); PPG, poly(propyleneglycol); m-PPG, methoxy-poly(propylene glycol); Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Sia, sialic acid; and NeuAc, N-acetylneuraminyl.

Introduction

To improve the effectiveness of recombinant human growth hormone used for therapeutic purposes, the present invention provides genetically engineered mutants of human growth hormone that contain N-linked or O-linked glycosylation sites not present in naturally occurring human growth hormone. While these hGH mutants substantially retain the biological activity of the wild-type hormone, the newly introduced glycosylation sites allow the recombinantly produced hGH mutants to be glycosylated in a large variety of patterns. Moreover, the non-natural glycosylation sites provide loci for conjugating modifying groups to the peptide, e.g., by glycoconjugation. An exemplary modifying group is a water-soluble polymer, such as poly(ethylene glycol), e.g., methoxy-poly(ethylene glycol). Modification of the hGH mutants can improve the stability and retention time of the recombinant hGH in a patient's circulation, reduce their antigenicity, and enhance their ability to target a specific tissue in need of treatment.

The Mutants

The present invention provides mutants of hGH that include one or more O- or N-linked glycosylation sites that are not found in the wild type peptide. The mutants are substrates for enzymatic glycosylation at one or more sites that would not normally be glycosylated, or would be poorly glycosylated, in the wild type peptide. Thus, the mutants allow the position of a glycosyl residue or a glycosyl linking group to be engineered to obtain a peptide having selected desirable properties. In addition to the position and number of glycosyl residues or glycosyl linking groups, other properties that can be varied using the mutants and methods of the invention include pharmacokinetics, pharmacodynamics, resistance to proteolysis, immunogenicity, recognition by the reticuloendothelial system, tissue distribution and the like.

Accordingly, in one aspect, the present invention provides an isolated nucleic acid comprising a polynucleotide sequence encoding a mutant human growth hormone. The mutant human growth hormone comprises an N-linked or O-linked glycosylation site that does not exist in the corresponding wild-type human growth hormone. In some embodiments, the corresponding wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, or 9.

In another aspect, the present invention provides an expression cassette or a cell that comprises a nucleic acid, e.g., an isolated nucleic acid, including a polynucleotide sequence encoding a mutant human growth hormone. The mutant human growth hormone includes an N-linked or O-linked glycosylation site that does not exist in the corresponding wild-type human growth hormone.

In another aspect, the present invention provides a mutant human growth hormone, that includes an N-linked or O-linked glycosylation site that does not exist in the corresponding wild-type human growth hormone. In some embodiments, the corresponding wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, or 9.

In another aspect, the present invention provides a method for making a mutant human growth hormone that includes an N-linked or O-linked glycosylation site that does not exist in the corresponding wild-type human growth hormone. This method comprises the steps of recombinantly producing the mutant human growth hormone, and glycosylating the mutant human growth hormone at the new glycosylation site. In some embodiments, the corresponding wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, or 9.

Acquisition of hGH Coding Sequences

General Recombinant Technology

This invention relies on routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of the cloned wild-type human growth hormone genes, polynucleotide encoding mutant human growth hormones, and synthetic oligonucleotides can be verified after cloning using, e.g., the chain termination method for sequencing double-stranded templates of Wallace et al., *Gene* 16: 21-26 (1981).

Cloning and Subcloning of a Wild-Type hGH Coding Sequence

A number of polynucleotide sequences encoding a wild-type human growth hormone, e.g., GenBank Accession Nos. NM 000515, NM 002059, NM 022556, NM 022557, NM 022558, NM 022559, NM 022560, NM 022561, and NM 022562, have been determined and can be obtained from a commercial supplier.

The rapid progress in the studies of human genome has made possible a cloning approach where a human DNA sequence database can be searched for any gene segment that has a certain percentage of sequence homology to a known nucleotide sequence, such as one encoding a previously identified human growth hormone. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a human growth hormone can be isolated from a human cDNA or genomic DNA library using standard cloning techniques such as polymerase chain reaction (PCR), where homology-based primers can often be derived from a known nucleic acid sequence encoding a human growth hormone. Most commonly used techniques for this purpose are described in standard texts, e.g., Sambrook and Russell, supra.

cDNA libraries suitable for obtaining a coding sequence for a wild-type human growth hormone may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., supra). Upon obtaining an amplified segment of nucleotide sequence by PCR, the segment can be further used as a probe to isolate the full length polynucleotide sequence encoding the wild-type human growth hormone from the cDNA library. A general description of appropriate procedures can be found in Sambrook and Russell, supra.

A similar procedure can be followed to obtain a full length sequence encoding a wild-type human growth hormone, e.g., any one of the GenBank Accession Nos. mentioned above, from a human genomic library. Human genomic libraries are commercially available or can be constructed according to various art-recognized methods. In general, to construct a genomic library, the DNA is first extracted from an tissue where a human growth hormone is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science,* 196: 180-182 (1977). Colony hybridization is carried out as described by Grunstein et al., *Proc. Natl. Acad. Sci. USA,* 72: 3961-3965 (1975).

Based on sequence homology, degenerate oligonucleotides can be designed as primer sets and PCR can be performed under suitable conditions (see, e.g., White et al., *PCR Protocols: Current Methods and Applications,* 1993; Griffin and Griffin, *PCR Technology*, CRC Press Inc. 1994) to amplify a segment of nucleotide sequence from a cDNA or genomic library. Using the amplified segment as a probe, the full length nucleic acid encoding a wild-type human growth hormone is obtained.

Upon acquiring a nucleic acid sequence encoding a wild-type human growth hormone, the coding sequence can be subcloned into a vector, for instance, an expression vector, so that a recombinant wild-type human growth hormone can be produced from the resulting construct. Further modifications to the wild-type human growth hormone coding sequence, e.g., nucleotide substitutions, may be subsequently made to alter the characteristics of the molecule.

Introducing Mutations into an hGH Sequence

From an encoding polynucleotide sequence, the amino acid sequence of a wild-type human growth hormone, e.g., SEQ ID NO:1 or SEQ ID NO:2, can be determined. Subsequently, this amino acid sequence may be modified to alter the protein's glycosylation pattern, by introducing additional glycosylation site(s) at various locations in the amino acid sequence.

Several types of protein glycosylation sites are well known in the art. For instance, in eukaryotes, N-linked glycosylation occurs on the asparagine of the consensus sequence Asn-$X_{aa}$-Ser/Thr, in which $X_{aa}$ is any amino acid except proline (Kornfeld et al., *Ann Rev Biochem* 54:631-664 (1985); Kukuruzinska et al., *Proc. Natl. Acad. Sci. USA* 84:2145-2149 (1987); Herscovics et al., *FASEB J* 7:540-550 (1993); and Orlean, *Saccharomyces* Vol. 3 (1996)). O-linked glycosylation takes place at serine or threonine residues (Tanner et al., *Biochim. Biophys. Acta.* 906:81-91 (1987); and Hounsell et al., *Glycoconj. J.* 13:19-26 (1996)). Other glycosylation patterns are formed by linking glycosylphosphatidylinositol to the carboxyl-terminal carboxyl group of the protein (Takeda et al., *Trends Biochem. Sci.* 20:367-371 (1995); and Udenfriend et al., *Ann. Rev. Biochem.* 64:593-591 (1995). Based on this knowledge, suitable mutations can thus be introduced into a wild-type human growth hormone sequence to form new glycosylation sites.

Although direct modification of an amino acid residue within a human growth hormone polypeptide sequence may be suitable to introduce a new N-linked or O-linked glycosylation site, more frequently, introduction of a new glycosylation site is accomplished by mutating the polynucleotide sequence encoding a human growth hormone. This can be achieved by using any of known mutagenesis methods, some of which are discussed below. Exemplary modifications to human growth hormone include those illustrated in SEQ ID NO:3 or SEQ ID NO:4.

A variety of mutation-generating protocols are established and described in the art. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science,* 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8764 and 8765-8787 (1985)), and mutagenesis using gapped duplex DNA (Kramer et al., *Nucl. Acids Res.,* 12: 9441-9456 (1984)).

Other possible methods for generating mutations include point mismatch repair (Kramer et al., *Cell,* 38: 879-887 (1984)), mutagenesis using repair-deficient host strains (Carter et al., *Nucl. Acids Res.,* 13: 4431-4443 (1985)), deletion mutagenesis (Eghtedarzadeh and Henikoff, *Nucl. Acids Res.,* 14: 5115 (1986)), restriction-selection and restriction-purification (Wells et al., *Phil. Trans. R. Soc. Lond A,* 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques,* 1: 11-15 (1989)).

Modification of Nucleic Acids for Preferred Codon Usage in a Host Organism

The polynucleotide sequence encoding a mutant human growth hormone can be further altered to coincide with the preferred codon usage of a particular host. For example, the preferred codon usage of one strain of bacterial cells can be used to derive a polynucleotide that encodes a mutant human growth hormone of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell. U.S. Pat. No. 5,824,864, for example, provides the frequency of codon usage by highly expressed genes exhibited by dicotyledonous plants and monocotyledonous plants.

At the completion of modification, the mutant human growth hormone coding sequences are verified by sequencing and are then subcloned into an appropriate expression vector for recombinant production in the same manner as the wild-type human growth hormones.

Expression and Purification of the Mutant hGH

Following sequence verification, the mutant human growth hormone of the present invention can be produced using routine techniques in the field of recombinant genetics, relying on the polynucleotide sequences encoding the polypeptide disclosed herein.

Expression Systems

To obtain high level expression of a nucleic acid encoding a mutant human growth hormone of the present invention, one typically subclones a polynucleotide encoding the mutant human growth hormone into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the wild-type or mutant human growth hormone are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the mutant human growth hormone in host cells. A typical expression cassette thus contains a promoter operably linked to the nucleic acid sequence encoding the mutant human growth hormone and signals required for efficient polyadenylation of the transcript, ribosome binding sites, and translation termination. The nucleic acid sequence encoding the human growth hormone is typically linked to a cleavable signal peptide sequence to promote secretion of the human growth hormone by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/$A^+$, pMTO10/$A^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the mutant human growth hormone under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., a hGH mutant of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

As discussed above, a person skilled in the art will recognize that various conservative substitutions can be made to any wild-type or mutant human growth hormone or its coding sequence while still retaining the biological activity of the human growth hormone. Moreover, modifications of a polynucleotide coding sequence may also be made to accommodate preferred codon usage in a particular expression host without altering the resulting amino acid sequence.

Transfection Methods

Standard transfection methods are used to produce bacterial, mammalian, yeast, insect, or plant cell lines that express large quantities of the mutant human growth hormone, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the mutant human growth hormone.

Detection of Expression of Mutant hGH in Host Cells

After the expression vector is introduced into appropriate host cells, the transfected cells are cultured under conditions favoring expression of the mutant human growth hormone. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a mutant human growth hormone in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a mutant human growth hormone of the present invention, such as a polypeptide having the amino acid sequence of SEQ ID NO:3, 4, or 5, (e.g., Harlow and Lane, *Antibodies, A Laboratory Manual*, Chapter 14, Cold Spring Harbor, 1988; Kohler and Milstein, *Nature,* 256: 495-497 (1975)). Such techniques require antibody preparation by selecting antibodies with high specificity against the mutant human growth hormone or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.,* 6: 511-519 (1976). More detailed descriptions of preparing antibody against the mutant human growth hormone of the present invention and conducting immunological assays detecting the mutant human growth hormone are provided in a later section.

Purification of Recombinantly Produced Mutant hGH

Once the expression of a recombinant mutant human growth hormone in transfected host cells is confirmed, the host cells are then cultured in an appropriate scale for the purpose of purifying the recombinant polypeptide.

Purification of Recombinantly Produced Mutant hGH from Bacteria

When the mutant human growth hormones of the present invention are produced recombinantly by transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant human growth hormone from bacterial inclusion body, see, e.g., Patra et al., *Protein Expression and Purification* 18: 182-190 (2000).

Alternatively, it is possible to purify recombinant polypeptides, e.g., a mutant human growth hormone, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Standard Protein Separation Techniques for Purification

When a recombinant polypeptide, e.g., the mutant human growth hormone of the present invention, is expressed in host cells in a soluble form, its purification can follow the standard protein purification procedure described below.

Solubility Fractionation

Often as an initial step, and if the protein mixture is complex, an initial salt fractionation can separate many of the unwanted host cell proteins (or proteins derived from the cell culture media) from the recombinant protein of interest, e.g., a mutant human growth hormone of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a mutant human growth hormone. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The proteins of interest (such as the mutant human growth hormone of the present invention) can also be separated from other proteins on the basis of their size, net surface charge, hydrophobicity, or affinity for ligands. In addition, antibodies raised against human growth hormone can be conjugated to column matrices and the human growth hormone immunopurified. All of these methods are well known in the art.

It will be apparent to one of skill that chromatographic techniques can be performed at any scale and using equipment from many different manufacturers (e.g., Pharmacia Biotech).

Immunoassays for Detection of Mutant hGH Expression

To confirm the production of a recombinant mutant human growth hormone, immunological assays may be useful to detect in a sample the expression of the polypeptide. Immunological assays are also useful for quantifying the expression level of the recombinant hormone. Antibodies against a mutant human growth hormone are necessary for carrying out these immunological assays.

Production of Antibodies against Mutant hGH

Methods for producing polyclonal and monoclonal antibodies that react specifically with an immunogen of interest are known to those of skill in the art (see, e.g., Coligan, *Current Protocols in Immunology* Wiley/Greene, N.Y., 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., a mutant human growth hormone of the present invention) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

When desired, antibodies capable of specifically recognizing a mutant human growth hormone of the present invention can be tested for their cross-reactivity against the wild-type human growth hormone and thus distinguished from the antibodies against the wild-type protein. For instance, antisera obtained from an animal immunized with a mutant human growth hormone can be run through a column on which a wild-type human growth hormone is immobilized. The portion of the antisera that passes through the column recognizes only the mutant human growth hormone and not the wild-type human growth hormone. Similarly, monoclonal antibodies against a mutant human growth hormone can also be screened for their exclusivity in recognizing only the mutant but not the wild-type human growth hormone.

Polyclonal or monoclonal antibodies that specifically recognize only the mutant human growth hormone of the present invention but not the wild-type human growth hormone are useful for isolating the mutant protein from the wild-type protein, for example, by incubating a sample with a mutant human growth hormone-specific polyclonal or monoclonal antibody immobilized on a solid support.

Immunoassays for Detecting Mutant hGH Expression

Once antibodies specific for a mutant human growth hormone of the present invention are available, the amount of the polypeptide in a sample, e.g., a cell lysate, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

Labeling in Immunoassays

Immunoassays often utilize a labeling agent to specifically bind to and label the binding complex formed by the antibody and the target protein. The labeling agent may itself be one of the moieties comprising the antibody/target protein complex, or may be a third moiety, such as another antibody, that specifically binds to the antibody/target protein complex. A label may be detectable by spectroscopic, photochemical, biochemical, immunochemical, electrical, optical or chemical means. Examples include, but are not limited to, magnetic beads (e.g., Dynabeads™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase, and others commonly used in an ELISA), and calorimetric labels such as colloidal gold or colored glass or plastic (e.g., polystyrene, polypropylene, latex, etc.) beads.

In some cases, the labeling agent is a second antibody bearing a detectable label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.,* 111: 1401-1406 (1973); and Akerstrom, et al., *J. Immunol.,* 135: 2589-2542 (1985)).

Immunoassay Formats

Immunoassays for detecting a target protein of interest (e.g., a mutant human growth hormone) from samples may be either competitive or noncompetitive. Noncompetitive immunoassays are assays in which the amount of captured target protein is directly measured. In one preferred "sandwich" assay, for example, the antibody specific for the target protein can be bound directly to a solid substrate where the antibody is immobilized. It then captures the target protein in test samples. The antibody/target protein complex thus immobilized is then bound by a labeling agent, such as a second or third antibody bearing a label, as described above.

In competitive assays, the amount of target protein in a sample is measured indirectly by measuring the amount of an added (exogenous) target protein displaced (or competed away) from an antibody specific for the target protein by the target protein present in the sample. In a typical example of such an assay, the antibody is immobilized and the exogenous target protein is labeled. Since the amount of the exogenous target protein bound to the antibody is inversely proportional to the concentration of the target protein present in the sample, the target protein level in the sample can thus be determined based on the amount of exogenous target protein bound to the antibody and thus immobilized.

In some cases, western blot (immunoblot) analysis is used to detect and quantify the presence of a mutant human growth hormone in the samples. The technique generally comprises separating sample proteins by gel electrophoresis on the basis of molecular weight, transferring the separated proteins to a suitable solid support (such as a nitrocellulose filter, a nylon filter, or a derivatized nylon filter) and incubating the samples with the antibodies that specifically bind the target protein. These antibodies may be directly labeled or alternatively may be subsequently detected using labeled antibodies (e.g., labeled sheep anti-mouse antibodies) that specifically bind to the antibodies against a mutant human growth hormone.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod Rev.,* 5: 34-41 (1986)).

Glycosylation and Glycoconjugation of the Mutant hGH

Glycosylation and Glycoconjugation by Enzymatic Methods

Post-expression in vitro modification of peptides is an attractive strategy to remedy the deficiencies of methods that rely on controlling glycosylation by engineering expression systems; including both modification of glycan structures or introduction of glycans at novel sites. A comprehensive arsenal of enzymes that transfer saccharide donor moieties is becoming available, making in vitro enzymatic synthesis of glycoconjugates with custom designed glycosylation patterns and glycosyl structures possible. See, for example, U.S. Pat. Nos. 5,876,980; 6,030,815; 5,728,554; 5,922,577; and published patent applications WO 98/31826; WO 01/88117; WO 03/031464; WO 03/046150; WO 03/045980; WO 03/093448; WO 04/009838; US2002/142370; US2003/040037; US2003/180835; US2004/063911; US2003/207406; and US2003/124645.

The invention provides methods for preparing conjugates of glycosylated and unglycosylated mutant human growth hormones, which have new glycosylation sites that do not exist in the corresponding wild-type hGH. Such conjugation may take place directly on the appropriate sugar units of a glycosylated mutant hGH, or following the removal (i.e., "trimming back") of any undesired sugar units. The conjugates are formed between peptides and diverse species such as water-soluble polymers, therapeutic moieties, diagnostic moieties, targeting moieties and the like. Also provided are conjugates that include two or more peptides linked together through a linker arm, i.e., multifunctional conjugates. The multi-functional conjugates of the invention can include two or more copies of the same peptide or a collection of diverse peptides with different structures, and/or properties.

The conjugates of the invention are formed by the enzymatic attachment of a modified sugar to the glycosylated or unglycosylated peptide. The modified sugar, when interposed between the peptide and the modifying group on the sugar becomes what is referred to herein as "an intact glycosyl linking group." Using the exquisite selectivity of enzymes, such as glycosyltransferases, the present method provides peptides that bear a desired group at one or more specific locations. Thus, according to the present invention, a modified sugar is attached directly to a selected locus on the peptide chain or, alternatively, the modified sugar is appended onto a carbohydrate moiety of a glycopeptide. Peptides in which modified sugars are bound to both a glycopeptide carbohydrate and directly to an amino acid residue of the peptide backbone are also within the scope of the present invention.

In contrast to known chemical and enzymatic peptide elaboration strategies, the methods of the invention, make it possible to assemble peptides and glycopeptides that have a substantially homogeneous derivatization pattern; the enzymes used in the invention are generally selective for a particular amino acid residue or combination of amino acid residues of the peptide. The methods are also practical for large-scale production of modified peptides and glycopeptides. Thus, the methods of the invention provide a practical means for large-scale preparation of glycopeptides having preselected uniform derivatization patterns. The methods are particularly well suited for modification of therapeutic peptides, including but not limited to, glycopeptides that are incompletely glycosylated during production in cell culture cells (e.g., mammalian cells, insect cells, plant cells, fungal cells, yeast cells, or prokaryotic cells) or transgenic plants or animals.

The methods of the invention also provide conjugates of glycosylated and unglycosylated peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent.

The Conjugates

In a first aspect, the present invention provides a conjugate between a selected modifying group and an hGH mutant peptide having a glycosylation site not present in the wild type peptide. The modifying group may be attached at the mutant glycosylation site or at a site that is present in the wild type peptide.

The link between the peptide and the modifying includes a glycosyl linking group interposed between the peptide and the selected moiety. As discussed herein, the selected moiety is essentially any species that can be attached to a saccharide unit, resulting in a "modified sugar" that is recognized by an appropriate transferase enzyme, which appends the modified sugar onto the peptide. The saccharide component of the modified sugar, when interposed between the peptide and a selected moiety, becomes a "glycosyl linking group," e.g., an "intact glycosyl linking group." The glycosyl linking group is formed from any mono- or oligo-saccharide that, after modification with the modifying group, is a substrate for an enzyme that adds the modified sugar to an amino acid or glycosyl residue of a peptide.

The glycosyl linking group can be, or can include, a saccharide moiety that is degradatively modified during the addition of the modifying group. For example, the glycosyl linking group can be derived from a saccharide residue that is produced by oxidative degradation of an intact saccharide to the corresponding aldehyde, e.g., via the action of metaperiodate, and subsequently converted to a Schiff base with an appropriate amine, which is then reduced to the corresponding amine.

The conjugates of the invention will typically correspond to the general structure:

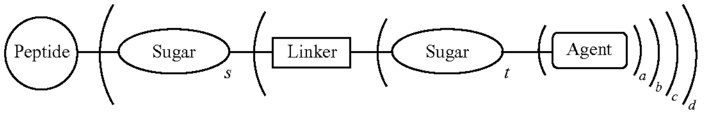

in which the symbols a, b, c, d and s represent a positive, non-zero integer; and t is either 0 or a positive integer. The "agent" is a therapeutic agent, a bioactive agent, a detectable label, water-soluble moiety (e.g., PEG, m-PEG, PPG, and m-PPG) or the like. The "agent" can be a peptide, e.g., enzyme, antibody, antigen, etc. The linker can be any of a wide array of linking groups, infra. Alternatively, the linker may be a single bond or a "zero order linker."

In an exemplary embodiment, the selected modifying group is a water-soluble polymer, e.g., m-PEG. The water-soluble polymer is covalently attached to the peptide via a glycosyl linking group. The glycosyl linking group is covalently attached to an amino acid residue or a glycosyl residue of the peptide. The invention also provides conjugates in which an amino acid residue and a glycosyl residue are modified with a glycosyl linking group.

An exemplary water-soluble polymer is poly(ethylene glycol), e.g., methoxy-poly(ethylene glycol). The poly(ethylene glycol) used in the present invention is not restricted to any particular form or molecular weight range. The poly(ethylene glycol) molecular weight is preferably between 500 and 100,000. A molecular weight of 500-60,000 is preferably used and preferably of from 1,000-40,000. More preferably, the molecular weight is from about 5,000 to about 40,000.

In another embodiment the poly(ethylene glycol) is a branched PEG having more than one PEG moiety attached. Examples of branched PEGs are described in U.S. Pat. No. 5,932,462; U.S. Pat. No. 5,342,940; U.S. Pat. No. 5,643,575; U.S. Pat. No. 5,919,455; U.S. Pat. No. 6,113,906; U.S. Pat. No. 5,183,660; WO 02/09766; Kodera Y., *Bioconjugate Chemistry* 5: 283-288 (1994); and Yamasaki et al., *Agric. Biol. Chem.*, 52: 2125-2127, 1998. In a preferred embodiment the molecular weight of each poly(ethylene glycol) of the branched PEG is 5,000-20,000.

In addition to providing conjugates that are formed through an enzymatically added glycosyl linking group, the present invention provides conjugates that are highly homogenous in their substitution patterns. Using the methods of the invention, it is possible to form peptide conjugates in which essentially all of the modified sugar moieties across a population of conjugates of the invention are attached to multiple copies of a structurally identical amino acid or glycosyl residue. Thus, in a second aspect, the invention provides a peptide conjugate having a population of water-soluble polymer moieties, which are covalently bound to the peptide through an intact glycosyl linking group. In a preferred conjugate of the invention, essentially each member of the population is bound via the glycosyl linking group to a glycosyl residue of the peptide, and each glycosyl residue of the peptide to which the glycosyl linking group is attached has the same structure.

Also provided is a peptide conjugate having a population of water-soluble polymer moieties covalently bound thereto through a glycosyl linking group. In a preferred embodiment, essentially every member of the population of water soluble polymer moieties is bound to an amino acid residue of the peptide via a glycosyl linking group, and each amino acid residue having a glycosyl linking group attached thereto has the same structure.

The present invention also provides conjugates analogous to those described above in which the peptide is conjugated to a therapeutic moiety, diagnostic moiety, targeting moiety, toxin moiety or the like via an intact glycosyl linking group. Each of the above-recited moieties can be a small molecule, natural polymer (e.g., polypeptide) or synthetic polymer.

In an exemplary embodiment, mutant human growth hormone is conjugated to transferrin via a bifunctional linker that includes an intact glycosyl linking group at each terminus of the PEG moiety (Scheme 1). For example, one terminus of the PEG linker is functionalized with an intact sialic acid linker that is attached to transferrin and the other is functionalized with an intact GalNAc linker that is attached to the mutant hGH.

The conjugates of the invention can include intact glycosyl linking groups that are mono- or multi-valent (e.g., antennary structures). Thus, conjugates of the invention include both species in which a selected moiety is attached to a peptide via a monovalent glycosyl linking group. Also included within the invention are conjugates in which more than one selected moiety is attached to a peptide via a multivalent linking group.

In a still further embodiment, the invention provides conjugates that localize selectively in a particular tissue due to the presence of a targeting agent as a component of the conjugate. In an exemplary embodiment, the targeting agent is a protein. Exemplary proteins include transferrin (brain, blood pool), HS-glycoprotein (bone, brain, blood pool), antibodies (brain, tissue with antibody-specific antigen, blood pool), coagulation factors V-XII (damaged tissue, clots, cancer, blood pool), serum proteins, e.g., α-acid glycoprotein, fetuin, α-fetal protein (brain, blood pool), β2-glycoprotein (liver, atherosclerosis plaques, brain, blood pool), G-CSF, GM-CSF, M-CSF, and EPO (immune stimulation, cancers, blood pool, red blood cell overproduction, neuroprotection), albumin (increase in half-life), and lipoprotein E.

The Methods

In addition to the conjugates discussed above, the present invention provides methods for preparing these and other conjugates. Thus, in a further aspect, the invention provides a method of forming a covalent conjugate between a selected moiety and a peptide. Additionally, the invention provides methods for targeting conjugates of the invention to a particular tissue or region of the body. Furthermore, the present invention provides a method for preventing, curing, or ameliorating a disease state by administering a conjugate of the invention to a subject at risk of developing the disease or a subject that has the disease.

In exemplary embodiments, the conjugate is formed between a water-soluble polymer, a therapeutic moiety, targeting moiety or a biomolecule, and a glycosylated or non-glycosylated peptide. The polymer, therapeutic moiety or biomolecule is conjugated to the peptide via an intact glycosyl linking group, which is interposed between, and covalently linked to both the peptide and the modifying group (e.g., water-soluble polymer). The method includes contacting the peptide with a mixture containing a modified sugar and a glycosyltransferase for which the modified sugar is a substrate. The reaction is conducted under conditions sufficient to form a covalent bond between the modified sugar and the peptide. The sugar moiety of the modified sugar is preferably selected from nucleotide sugars, activated sugars, and sugars that are neither nucleotides nor activated.

The acceptor peptide (glycosylated or non-glycosylated) is typically synthesized de novo, or recombinantly expressed in a prokaryotic cell (e.g., bacterial cell, such as *E. coli*) or in a eukaryotic cell such as a mammalian, yeast, insect, fungal or plant cell. The peptide can be either a full-length protein or a fragment. Moreover, the peptide can be a wild type or mutated peptide. In an exemplary embodiment, the peptide includes a mutation that adds one or more consensus glycosylation sites to the peptide sequence.

The method of the invention also provides for modification of incompletely glycosylated peptides that are produced recombinantly. Many recombinantly produced glycoproteins are incompletely glycosylated, exposing carbohydrate residues that may have undesirable properties, e.g., immunogenicity, recognition by the RES. Employing a modified sugar in a method of the invention, the peptide can be simultaneously further glycosylated and derivatized with, e.g., a water-soluble polymer, therapeutic agent, or the like. The sugar moiety of the modified sugar can be the residue that would properly be conjugated to the acceptor in a fully glycosylated peptide, or another sugar moiety with desirable properties.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-aceylgalactosamine, galactose, mannose, GlcNAc, glucose, fucose or xylose) to a the hydroxy side chain of a hydroxyamino acid, preferably serine or threonine, although 5-hydroxyproline or 5-hydroxylysine may also be used.

Addition of glycosylation sites to a peptide or other structure is conveniently accomplished by altering the amino acid sequence such that it contains one or more glycosylation sites. The addition may also be made by the incorporation of one or more species presenting an —OH group, preferably serine or threonine residues, within the sequence of the peptide (for O-linked glycosylation sites). The addition may be made by mutation or by full chemical synthesis of the peptide. The peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

The present invention also provides means of adding (or removing) one or more selected glycosyl residues to a peptide, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. Chemical deglycosylation is preferably brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N-linked glycosylation and O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC CRIT. REV. BIOCHEM., pp. 259-306 (1981).

In one embodiment, the invention provides a method for linking hGH and one or more peptide through a linking group. The linking group is of any useful structure and may be selected from straight-chain and branched chain structures. Preferably, each terminus of the linker, which is attached to a peptide, includes a modified sugar (i.e., a nascent intact glycosyl linking group).

In an exemplary method of the invention, two peptides are linked together via a linker moiety that includes a PEG linker. The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second peptides to the first and second glycosylunits, respectively. In practice, the (glycosyl)$^1$-PEG-(glycosyl)$^2$ linker is contacted with the first peptide and a first transferase for which the first glycosyl unit is a substrate, thereby forming (peptide)$^1$-(glycosyl)$^1$-PEG-(glycosyl)$^2$. Glycosyltransferase and/or unreacted peptide is then optionally removed from the reaction mixture. The second peptide and a second transferase for which the second glycosyl unit is a substrate are added to the (peptide)$^1$-(glycosyl)$^1$-PEG-(glycosyl)$^2$ conjugate, forming (peptide)$^1$-(glycosyl)$^1$-PEG-(glycosyl)$^2$-(peptide)$^2$. Those of skill in the art will appreciate that the method outlined above is also applicable to forming conjugates between more than two peptides by, for example, the use of a branched PEG, dendrimer, poly (amino acid), polsaccharide or the like.

In an exemplary embodiment, human growth hormone is conjugated to transferrin via a bifunctional linker that includes an intact glycosyl linking group at each terminus of the PEG moiety (Scheme 1). The hGH conjugate has an in vivo half-life that is increased over that of hGH alone by virtue of the greater molecular sized of the conjugate. Moreover, the conjugation of hGH to transferrin serves to selectively target the conjugate to the brain. For example, one terminus of the PEG linker is functionalized with a CMP sialic acid and the other is functionalized with an UDP Gal-NAc. The linker is combined with hGH in the presence of a GalNAc transferase, resulting in the attachment of the GalNAc of the linker arm to a serine and/or threonine residue on the hGH.

Scheme 1

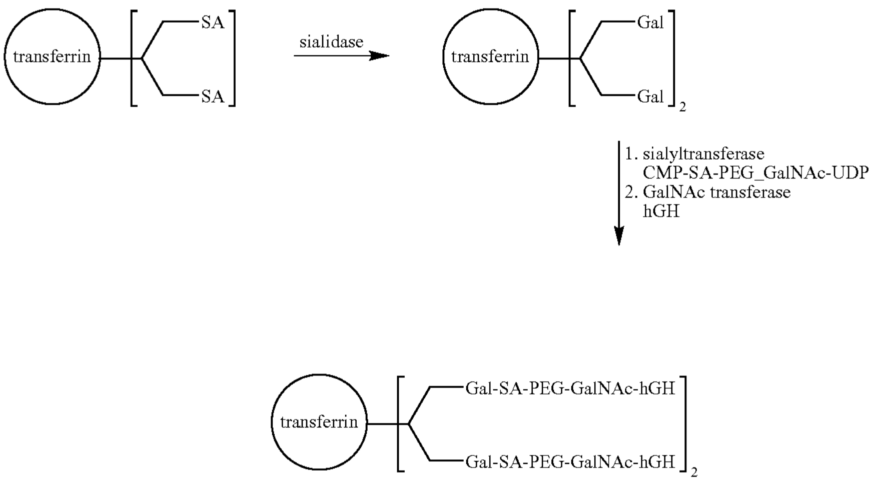

The processes described above can be carried through as many cycles as desired, and is not limited to forming a conjugate between two peptides with a single linker. Moreover, those of skill in the art will appreciate that the reactions functionalizing the intact glycosyl linking groups at the termini of the PEG (or other) linker with the peptide can occur simultaneously in the same reaction vessel, or they can be carried out in a step-wise fashion. When the reactions are carried out in a step-wise manner, the conjugate produced at each step is optionally purified from one or more reaction components (e.g., enzymes, peptides).

A still further exemplary embodiment is set forth in Scheme 2. Scheme 2 shows a method of preparing a conjugate that targets a selected protein, e.g., human growth hormone, to bone and increases the circulatory half-life of the selected protein.

Scheme 2

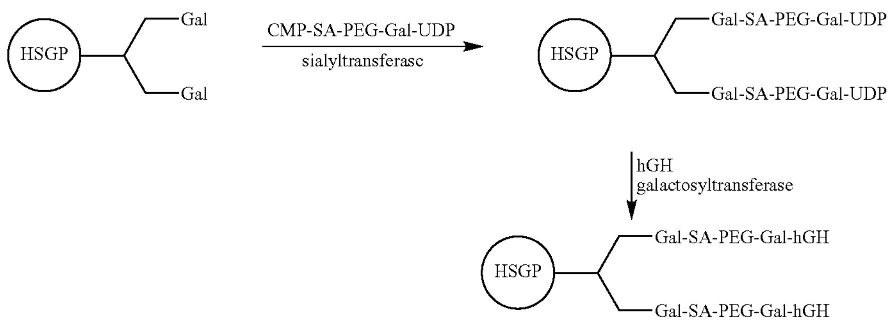

in which G is a glycosyl residue on an activated sugar moiety (e.g., sugar nucleotide), which is converted to an intact glycosyl linker group in the conjugate. When s is greater than 0, L is a saccharyl linking group such as GalNAc, or GalNAc-Gal.

The use of reactive derivatives of PEG (or other linkers) to attach one or more peptide moieties to the linker is within the scope of the present invention. The invention is not limited by the identity of the reactive PEG analogue. Many activated derivatives of poly(ethyleneglycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.,* 7: 175-186 (1984); Abuchowski et al., *J. Biol. Chem.,* 252: 3582-3586 (1977); Jackson et al., *Anal. Biochem.,* 165: 114-127 (1987); Koide et al., *Biochem Biophys. Res. Commun.,* 111: 659-667 (1983)), tresylate (Nilsson et al., *Methods Enzymol.,* 104: 56-69 (1984); Delgado et al., *Biotechnol. Appl. Biochem.,* 12: 119-128 (1990)); N-hydroxysuccinimide derived active esters (Buckmann et al., *Makromol. Chem.,* 182: 1379-1384 (1981); Joppich et al., *Makromol. Chem.,* 180: 1381-1384 (1979); Abuchowski et al., *Cancer Biochem. Biophys.,* 7: 175-186 (1984); Katre et al. *Proc. Natl. Acad. Sci. U.S.A.,* 84: 1487-1491 (1987); Kitamura et al., *Cancer Res.,* 51: 4310-4315 (1991); Boccu et al., *Z. Naturforsch.,* 38C: 94-99 (1983), carbonates (Zalipsky et al., Poly(ethylene glycol) Chemistry: Biotechnical and Biomedical Applications, Harris, Ed., Plenum Press, New York, 1992, pp. 347-370; Zalipsky et al., *Biotechnol. Appl. Biochem.,* 15: 100-114 (1992); Veronese et al., *Appl. Biochem. Biotech.,* 11: 141-152 (1985)), imidazolyl formates (Beauchamp et al., *Anal. Biochem.,* 131: 25-33 (1983); Berger et al., *Blood,* 71: 1641-1647 (1988)), 4-dithiopyridines (Woghiren et al., *Bioconjugate Chem.,* 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.,* 11: 141-152 (1985).

In another exemplary embodiment, the invention provides a method for extending the blood-circulation half-life of a selected peptide, in essence targeting the peptide to the blood pool, by conjugating the peptide to a synthetic or natural polymer of a size sufficient to retard the filtration of the protein by the glomerulus (e.g., albumin). See, Scheme 3. This embodiment of the invention is illustrated in Scheme 3 in which hGH is conjugated to albumin via a PEG linker using a combination of chemical and enzymatic modification.

Scheme 3

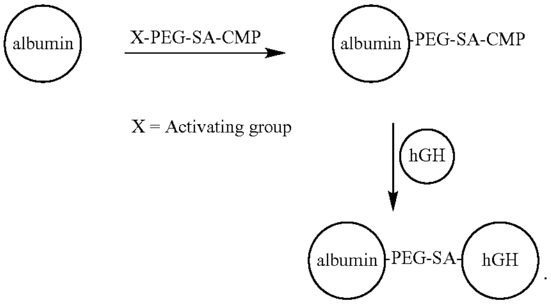

Thus, as shown in Scheme 3, a residue (e.g., amino acid side chain) of albumin is modified with a reactive PEG derivative, such as X-PEG-(CMP-sialic acid), in which X is an activating group (e.g., active ester, isothiocyanate, etc). The PEG derivative and hGH are combined and contacted with a transferase for which CMP-sialic acid is a substrate. In a further illustrative embodiment, an ε-amine of lysine is reacted with the N-hydroxysuccinimide ester of the PEG-linker to form the albumin conjugate. The CMP-silaic acid of the linker is enzymatically conjugated to an appropriate residue on hGH, e.g., Gal or GalNAc, thereby forming the conjugate. Those of skill will appreciate that the above-described method is not limited to the reaction partners set forth. Moreover, the method can be practiced to form conjugates that include more than two protein moieties by, for example, utilizing a branched linker having more than two termini.

Modified Sugars

Modified glycosyl donor species ("modified sugars") are preferably selected from modified sugar nucleotides, activated modified sugars and modified sugars that are simple saccharides that are neither nucleotides nor activated. Any desired carbohydrate structure can be added to a peptide using the methods of the invention. Typically, the structure will be a monosaccharide, but the present invention is not limited to the use of modified monosaccharide sugars; oligosaccharides and polysaccharides are useful as well.

The modifying group is attached to a sugar moiety by enzymatic means, chemical means or a combination thereof, thereby producing a modified sugar. The sugars are substituted at any position that allows for the attachment of the modifying moiety, yet which still allows the sugar to function as a substrate for the enzyme used to ligate the modified sugar to the peptide. In a preferred embodiment, when sialic acid is the sugar, the sialic acid is substituted with the modifying group at either the 9-position on the pyruvyl side chain or at the 5-position on the amine moiety that is normally acetylated in sialic acid.

In certain embodiments of the present invention, a modified sugar nucleotide is utilized to add the modified sugar to the peptide. Exemplary sugar nucleotides that are used in the present invention in their modified form include nucleotide mono-, di- or triphosphates or analogs thereof. In a preferred embodiment, the modified sugar nucleotide is selected from a UDP-glycoside, CMP-glycoside, or a GDP-glycoside. Even more preferably, the modified sugar nucleotide is selected from an UDP-galactose, UDP-galactosamine, UDP-glucose, UDP-glucosamine, GDP-mannose, GDP-fucose, CMP-sialic acid, or CMP-NeuAc. N-acetylamine derivatives of the sugar nucleotides are also of use in the method of the invention.

The invention also provides methods for synthesizing a modified peptide using a modified sugar, e.g., modified-galactose, -fucose, -GalNAc, and -sialic acid. When a modified sialic acid is used, either a sialyltransferase or a trans-sialidase (for α2,3-linked sialic acid only) can be used in these methods.

In other embodiments, the modified sugar is an activated sugar. Activated modified sugars, which are useful in the present invention are typically glycosides which have been synthetically altered to include an activated leaving group. As used herein, the term "activated leaving group" refers to those moieties, which are easily displaced in enzyme-regulated nucleophilic substitution reactions. Many activated sugars are known in the art. See, for example, Vocadlo et al., In Carbohydrate Chemistry and Biology, Vol. 2, Ernst et al. Ed., Wiley-VCH Verlag: Weinheim, Germany, 2000; Kodama et al., *Tetrahedron Lett.* 34: 6419 (1993); Lougheed, et al., *J. Biol. Chem.* 274: 37717 (1999)).

Examples of activating groups (leaving groups) include fluoro, chloro, bromo, tosylate ester, mesylate ester, triflate ester and the like. Preferred activated leaving groups, for use in the present invention, are those that do not significantly sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride are most preferred.

By way of illustration, glycosyl fluorides can be prepared from the free sugar by first acetylating the sugar and then treating it with HF/pyridine. This generates the thermodynamically most stable anomer of the protected (acetylated) glycosyl fluoride (i.e., the α-glycosyl fluoride). If the less stable anomer (i.e., the β-glycosyl fluoride) is desired, it can be prepared by converting the peracetylated sugar with HBr/HOAc or with HCl to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g. NaOMe/MeOH). In addition, many glycosyl fluorides are commercially available.

Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

In a further exemplary embodiment, the modified sugar is an oligosaccharide having an antennary structure. In a preferred embodiment, one or more of the termini of the antennae bear the modifying moiety. When more than one modifying moiety is attached to an oligosaccharide having an antennary structure, the oligosaccharide is useful to "amplify" the modifying moiety; each oligosaccharide unit conjugated to the peptide attaches multiple copies of the modifying group to the peptide. The general structure of a typical chelate of the invention as set forth in the drawing above, encompasses multivalent species resulting from preparing a conjugate of the invention utilizing an antennary structure. Many antennary saccharide structures are known in the art, and the present method can be practiced with them without limitation.

Exemplary modifying groups are discussed below. The modifying groups can be selected for their ability to impart to a polypeptide one or more desirable properties. Exemplary properties include, but are not limited to, enhaced pharmacokinetics, enhanced pharmacodynamics, improved biodistribution, providing a polyvalent species, improved water solubility, enhanced or diminished lipophilicity, and tissue targeting.

Water-Soluble Polymers

The hydrophilicity of a selected peptide is enhanced by conjugation with polar molecules such as amine-, ester-, hydroxyl- and polyhydroxyl-containing molecules. Representative examples include, but are not limited to, polylysine, polyethyleneimine, and polyethers, e.g., poly(ethylene glycol), m-poly(ethylene glycol), poly(propyleneglycol), m-poly(propylene glycol), and other O-alkyl poly(alkylene glycol) moieties. Preferred water-soluble polymers are essentially non-fluorescent, or emit such a minimal amount of fluorescence that they are inappropriate for use as a fluorescent marker in an assay. Moreover, it is generally preferred to use polymers that are not naturally occurring sugars. An exception to this preference is the use of an otherwise naturally occurring sugar that is modified by covalent attachment of another entity (e.g., poly(ethylene glycol), poly(propylene glycol), biomolecule, therapeutic moiety, diagnostic moiety, etc.). In another exemplary embodiment, a therapeutic sugar moiety is conjugated to a linker arm and the sugar-linker arm cassette is subsequently conjugated to a peptide via a method of the invention.

Methods and chemistry for activation of water-soluble polymers and saccharides as well as methods for conjugating saccharides and polymers to various species are described in the literature. Commonly used methods for activation of polymers include activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), Protein Immobilisation. Fundamentals and Applications, Marcel Dekker, N.Y.; S. S. Wong, (1992), Chemistry of Protein Conjugation and Crosslinking, CRC Press, Boca Raton; G. T. Hermanson et al., (1993), Immobilized Affinity Ligand Techniques, Academic Press, N.Y.; Dunn, R. L., et al., Eds. Polymeric Drugs And Drug Delivery Systems, ACS Symposium Series Vol. 469, American Chemical Society, Washington, D.C. 1991).

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly(amino acids);

nucleic acids; synthetic polymers (e.g., poly(acrylic acid), poly(ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), haemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Preferred water-soluble polymers are those in which a substantial proportion of the polymer molecules in a sample of the polymer are of approximately the same molecular weight; such polymers are said to be "homodisperse" or "monodisperse."

The present invention is further illustrated by reference to a poly(ethylene glycol) or monomethoxy-poly(ethylene glycol) (m-PEG) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie*, 57:5-29 (2002).

The poly(ethylene glycol) useful in forming the conjugate of the invention is either linear or branched.

The in vivo half-life or area under the curve (AUC) of therapeutic glycopeptides can also be enhanced with water-soluble polymers such as PEG, m-PEG, PPG, and m-PPG. For example, chemical modification of proteins with PEG (PEG-ylation) or m-PEG (m-PEG-ylation) increases their molecular size and decreases their surface- and functional group-accessibility, each of which are dependent on the size of the PEG attached to the protein. This results in an improvement of plasma half-lives or AUCs and in proteolytic-stability, and a decrease in immunogenicity and hepatic uptake (Chaffee et al. *J. Clin. Invest.* 89: 1643-1651 (1992); Pyatak et al. *Res. Commun. Chem. Pathol Pharmacol.* 29: 113-127 (1980)). PEGylation of interleukin-2 has been reported to increase its antitumor potency in vivo (Katre et al. *Proc. Natl. Acad. Sci. USA.* 84: 1487-1491 (1987)) and PEG-ylation of a F(ab')2 derived from the monoclonal antibody A7 has improved its tumor localization (Kitamura et al. *Biochem. Biophys. Res. Commun.* 28: 1387-1394 (1990)). Thus, in another preferred embodiment, the in vivo half-life of a peptide derivatized with a water-soluble polymer by a method of the invention is increased relevant to the in vivo half-life or AUC of the non-derivatized peptide.

The increase in peptide in vivo half-life or AUC is best expressed as a range of percent increase in this quantity. The lower end of the range of percent increase is about 40%, about 60%, about 80%, about 100%, about 150% or about 200%. The upper end of the range is about 60%, about 80%, about 100%, about 150%, or more than about 250%.

PEG moieties of any molecular weight, e.g., 5 kD, 10 kD, 20 kD, and 30 kD, are of use in the present invention.

Biomolecules

In another preferred embodiment, the modified sugar bears a biomolecule. In still further preferred embodiments, the biomolecule is a functional protein, enzyme, antigen, antibody, peptide, nucleic acid (e.g., single nucleotides or nucleosides, oligonucleotides, polynucleotides and single- and higher-stranded nucleic acids), lectin, receptor or a combination thereof.

Preferred biomolecules are essentially non-fluorescent, or emit such a minimal amount of fluorescence that they are inappropriate for use as a fluorescent marker in an assay. Moreover, it is generally preferred to use biomolecules that are not sugars. An exception to this preference is the use of an otherwise naturally occurring sugar that is modified by covalent attachment of another entity (e.g., PEG, biomolecule, therapeutic moiety, diagnostic moiety, etc.). In an exemplary embodiment, a sugar moiety, which is a biomolecule, is conjugated to a linker arm and the sugar-linker arm cassette is subsequently conjugated to a peptide via a method of the invention.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides useful in practicing the instant invention include, for example, enzymes, antigens, antibodies and receptors. Antibodies can be either polyclonal or monoclonal; either intact or fragments. The peptides are optionally the products of a program of directed evolution.

Both naturally derived and synthetic peptides and nucleic acids are of use in conjunction with the present invention; these molecules can be attached to a sugar residue component or a crosslinking agent by any available reactive group. For example, peptides can be attached through a reactive amine, carboxyl, sulfhydryl, or hydroxyl group. The reactive group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further preferred embodiment, the biomolecule is selected to direct the peptide modified by the methods of the invention to a specific tissue, thereby enhancing the delivery of the peptide to that tissue relative to the amount of underivatized peptide that is delivered to the tissue. In a still further preferred embodiment, the amount of derivatized peptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors.

In still a further exemplary embodiment, there is provided as conjugate with biotin. Thus, for example, a selectively biotinylated peptide is elaborated by the attachment of an avidin or streptavidin moiety bearing one or more modifying groups.

Therapeutic Moieties

In another preferred embodiment, the modified sugar includes a therapeutic moiety. Those of skill in the art will appreciate that there is overlap between the category of therapeutic moieties and biomolecules; many biomolecules have therapeutic properties or potential.

The therapeutic moieties can be agents already accepted for clinical use or they can be drugs whose use is experimental, or whose activity or mechanism of action is under investigation. The therapeutic moieties can have a proven action in a given disease state or can be only hypothesized to show desirable action in a given disease state. In a preferred embodiment, the therapeutic moieties are compounds, which are being screened for their ability to interact with a tissue of choice. Therapeutic moieties, which are useful in practicing the instant invention include drugs from a broad range of drug classes having a variety of pharmacological activities. Preferred therapeutic moieties are essentially non-fluorescent, or emit such a minimal amount of fluorescence that they are inappropriate for use as a fluorescent marker in an assay. Moreover, it is generally preferred to use therapeutic moieties that are not sugars. An exception to this preference is the use of a sugar that is modified by covalent attachment of another entity, such as a PEG, biomolecule, therapeutic moiety, diagnostic moiety and the like. In another exemplary embodiment, a therapeutic sugar moiety is conjugated to a linker arm and the sugar-linker arm cassette is subsequently conjugated to a peptide via a method of the invention.

Methods of conjugating therapeutic and diagnostic agents to various other species are well known to those of skill in the art. See, for example Hermanson, Bioconjugate Techniques, Academic Press, San Diego, 1996; and Dunn et al., Eds. Polymeric Drugs And Drug Delivery Systems, ACS Symposium Series Vol. 469, American Chemical Society, Washington, D.C. 1991.

In an exemplary embodiment, the therapeutic moiety is attached to the modified sugar via a linkage that is cleaved under selected conditions. Exemplary conditions include, but are not limited to, a selected pH (e.g., stomach, intestine, endocytotic vacuole), the presence of an active enzyme (e.g., esterase, reductase, oxidase), light, heat and the like. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989).

Classes of useful therapeutic moieties include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; antihistaminic drugs (e.g., chlorpheniramine, triprolidine); antitussive drugs (e.g., dextromethorphan, codeine, caramiphen and carbetapentane); antipruritic drugs (e.g., methdilazine and trimeprazine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermine, fenfluramine); central stimulant drugs (e.g., amphetamine, methamphetamine, dextroamphetamine and methylphenidate); antiarrhythmic drugs (e.g., propanolol, procainamide, disopyramide, quinidine, encamide); β-adrenergic blocker drugs (e.g., metoprolol, acebutolol, betaxolol, labetalol and timolol); cardiotonic drugs (e.g., milrinone, aminone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltiazem, amiodarone, isoxsuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chloroprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazepam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amantadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, β-2-interferon) anti-estrogens (e.g., tamoxifen), antimetabolites (e.g., fluorouracil, methotrexate, mercaptopurine, thioguanine). Also included within this class are radioisotope-based agents for both diagnosis and therapy, and conjugated toxins, such as ricin, geldanarnycin, mytansin, CC-1065, the duocarmycins, Chlicheamycin and related structures and analogues thereof.

The therapeutic moiety can also be a hormone (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, diphenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progestogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful modifying groups include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine H2 antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

Preparation of Modified Sugars

In general, the sugar moiety and the modifying group are linked together through the use of reactive groups, which are typically transformed by the linking process into a new organic functional group or species that is unreactive under physiologically relevant conditions. The sugar reactive functional group(s), is located at any position on the sugar moiety. Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

Useful reactive functional groups pendent from a sugar nucleus or modifying group include, but are not limited to:

(a) carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., Protective Groups in Organic Synthesis, John Wiley & Sons, New York, 1991.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., *Curr. Med. Chem.* 6: 93 (1999); and Schafer et al., *J. Org. Chem.* 65: 24 (2000)).

In an exemplary embodiment, the peptide that is modified by a method of the invention is a glycopeptide that is produced in prokaryotic cells (e.g., *E. coli*), eukaryotic cells including yeast and mammalian cells (e.g., CHO cells), or in a transgenic animal and thus, contains N- and/or O-linked oligosaccharide chains, which are incompletely sialylated. The oligosaccharide chains of the glycopeptide lacking a sialic acid and containing a terminal galactose residue can be PEG-ylated, PPG-ylated or otherwise modified with a modified sialic acid.

Exemplary PEG-sialic acid derivative include:

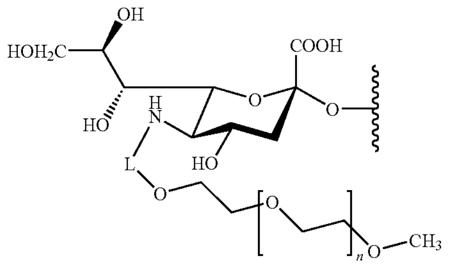

in which L is a substituted or unsubstituted alkyl or substituted or unsubstituted heteroalkyl linker moiety joining the sialic acid moiety and the PEG moiety, and "n" is 1 or greater; and

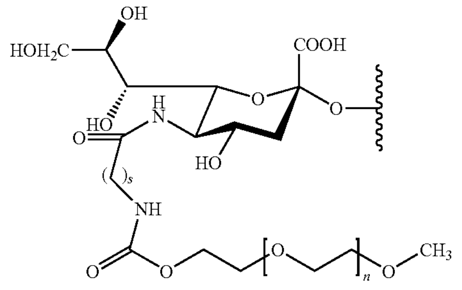

in which the index "s" represents an integer from 0 to 20, and "n" is 1 or greater.

In Scheme 4, the amino glycoside 1, is treated with the active ester of a protected amino acid (e.g., glycine) derivative, converting the sugar amine residue into the corresponding protected amino acid amide adduct. The adduct is treated with an aldolase to form α-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG attachment by reacting compound 3 with an activated PEG or PPG derivative (e.g., PEG-C(O)NHS, PEG-OC(O)O-p-nitrophenyl), producing species such as 4 or 5, respectively.

Scheme 4

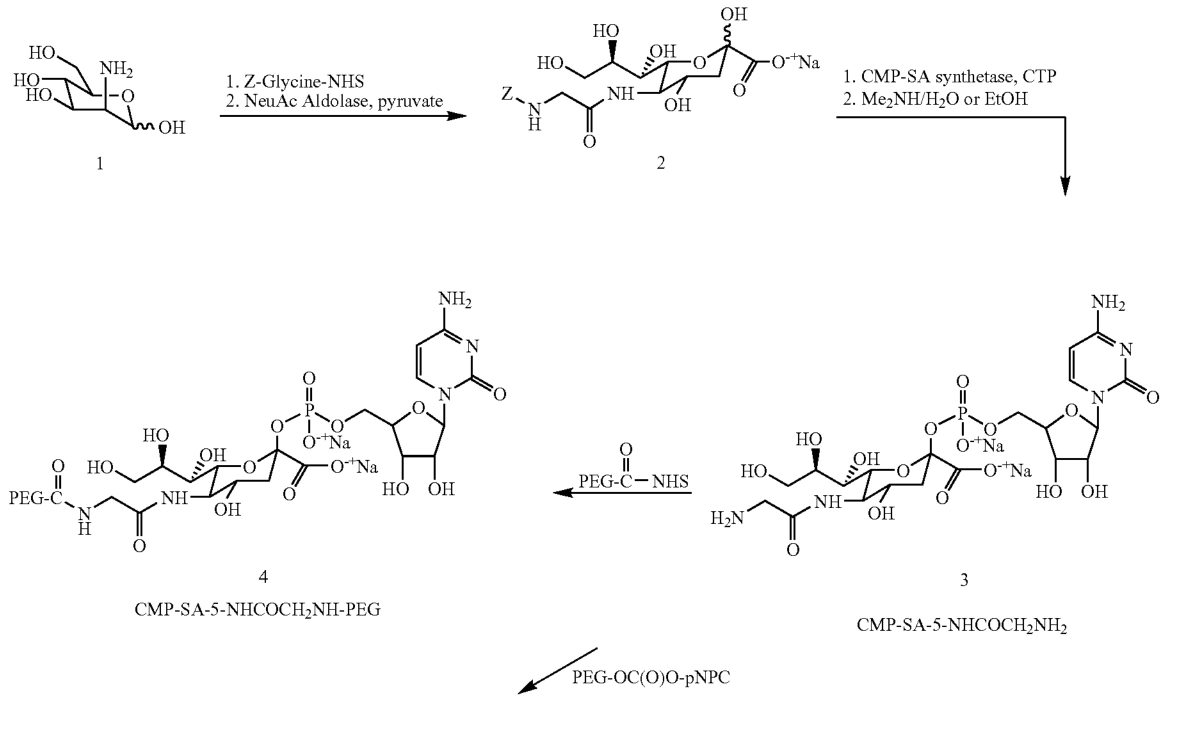

1, 2, 3, 4

4: CMP-SA-5-NHCOCH$_2$NH-PEG

3: CMP-SA-5-NHCOCH$_2$NH$_2$

CMP-SA-5-NHCOCH$_2$NH—C(O)O-PEG

5

Table 1 sets forth representative examples of sugar monophosphates that are derivatized with a PEG or PPG moiety. Human growth hormone mutants can be modified by the method of Scheme 1. Other derivatives are prepared by art-recognized methods. See, for example, Keppler et al., *Glycobiology* 11: 11R (2001); and Charter et al., *Glycobiology* 10: 1049 (2000)). Other amine reactive PEG and PPG analogues are commercially available, or they can be prepared by methods readily accessible to those of skill in the art.

TABLE 1

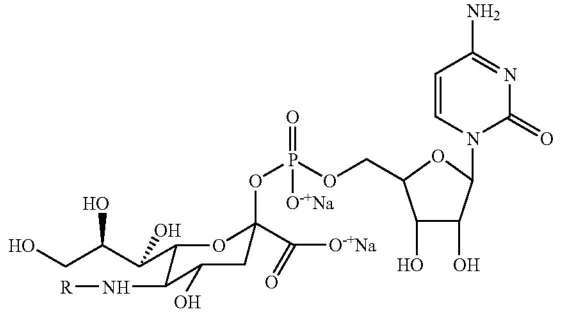

CMP-SA-5-NH—R

TABLE 1-continued

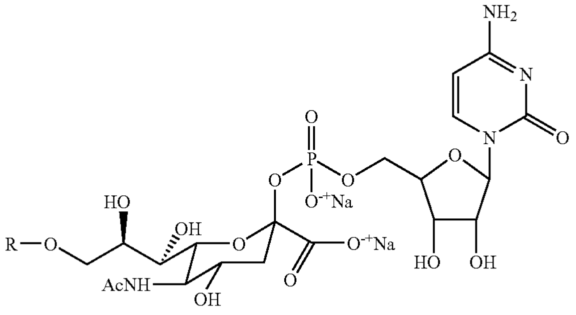

CMP-NeuAc-9-O—R

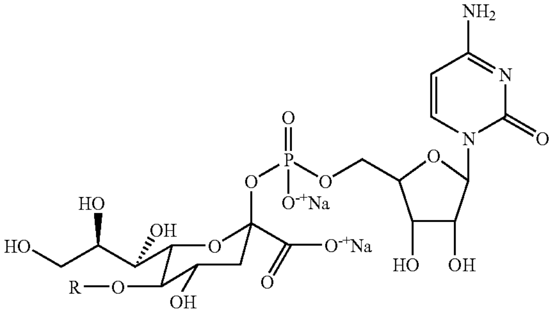

CMP-KDN-5-O—R

TABLE 1-continued

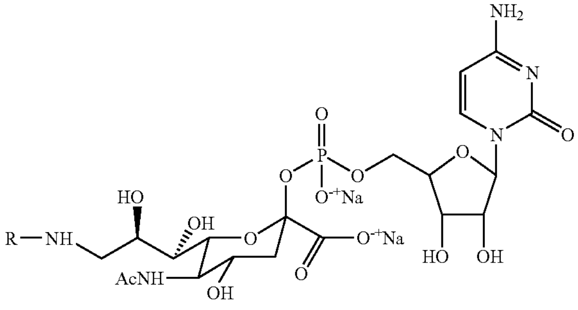

CMP-NeuAc-9-NH—R

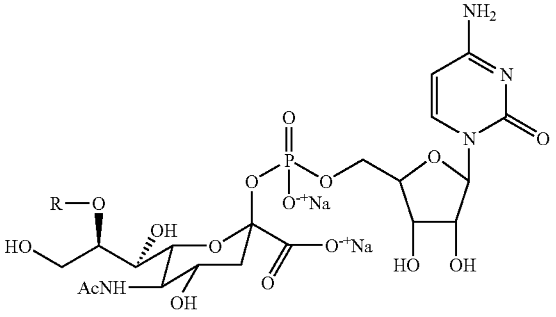

CMP-NeuAc-8-O—R

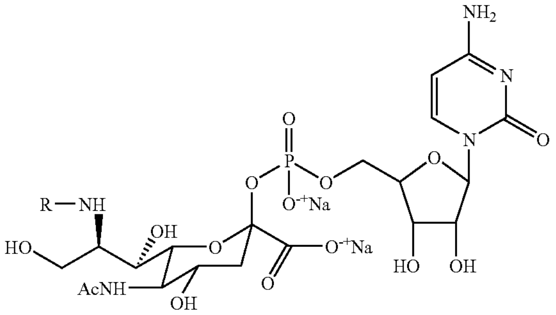

CMP-NeuAc-8-NH—R

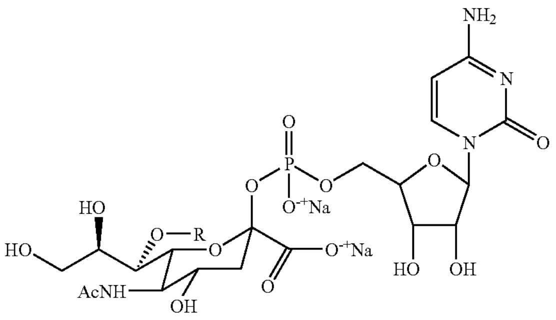

CMP-NeuAc-7-O—R

TABLE 1-continued

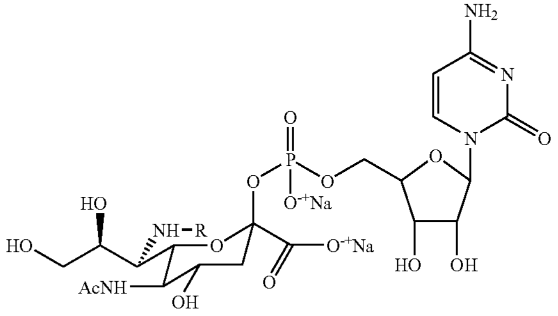

CMP-NeuAc-7-NH—R

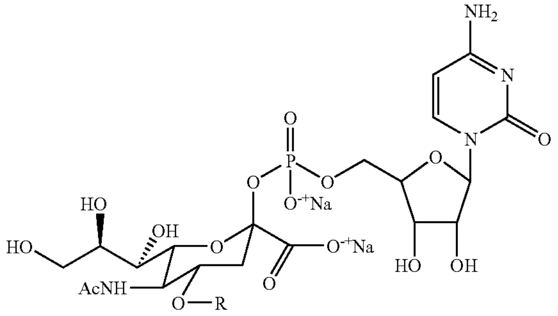

CMP-NeuAc-4-O—R

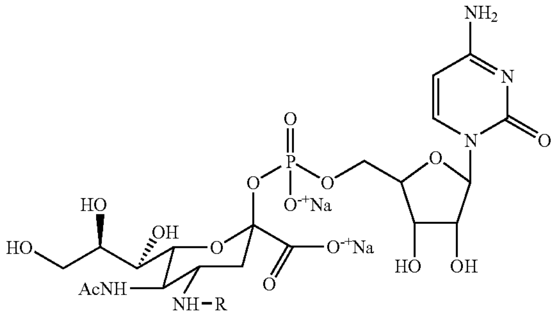

CMP-NeuAc-4-NH—R

The modified sugar phosphates of use in practicing the present invention can be substituted in other positions as well as those set forth above. Presently preferred substitutions of sialic acid are set forth in Formula I:

(I)

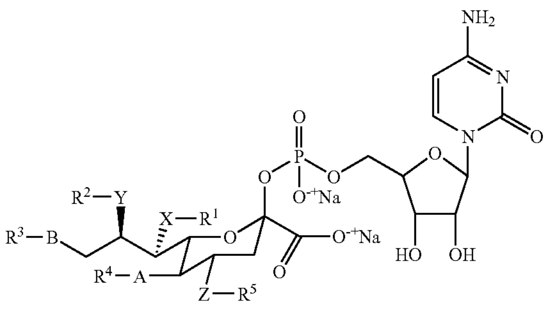

in which X is a linking group, which is preferably selected from —O—, —N(H)—, —S, $CH_2$—, and —N(R)$_2$, in which each R is a member independently selected from $R^1$-$R^5$. The symbols Y, Z, A and B each represent a group that is selected from the group set forth above for the identity of X. X, Y, Z, A and B are each independently selected and, therefore, they can be the same or different. The symbols $R^1$, $R^2$, $R^3$, $R^4$ and $R^5$ represent H, a water-soluble polymer, therapeutic moiety, biomolecule or other moiety. Alternatively, these symbols represent a linker that is bound to a water-soluble polymer, therapeutic moiety, biomolecule or other moiety.

Exemplary moieties attached to the conjugates disclosed herein include, but are not limited to, PEG derivatives (e.g., alkyl-PEG, acyl-PEG, acyl-alkyl-PEG, alkyl-acyl-PEG carbamoyl-PEG, aryl-PEG), PPG derivatives (e.g., alkyl-PPG, acyl-PPG, acyl-alkyl-PPG, alkyl-acyl-PPG carbamoyl-PPG, aryl-PPG), therapeutic moieties, diagnostic moieties, mannose-6-phosphate, heparin, heparan, $SLe_x$, mannose, mannose-6-phosphate, Sialyl Lewis X, FGF, VFGF, proteins, chondroitin, keratan, dermatan, albumin, integrins, antennary oligosaccharides, peptides and the like. Methods of conjugating the various modifying groups to a saccharide moiety are readily accessible to those of skill in the art (Poly (Ethylene Glycol Chemistry: Biotechnical and Biomedical Applications, J. Milton Harris, Ed., Plenum Pub. Corp., 1992; Poly (Ethylene Glycol) Chemical and Biological Applications, J. Milton Harris, Ed., ACS Symposium Series No. 680, American Chemical Society, 1997; Hermanson, Bioconjugate Techniques, Academic Press, San Diego, 1996; and Dunn et al., Eds. Polymeric Drugs And Drug Delivery Systems, ACS Symposium Series Vol. 469, American Chemical Society, Washington, D.C. 1991).

Cross-Linking Groups

Preparation of the modified sugar for use in the methods of the present invention includes attachment of a modifying group to a sugar residue and forming a stable adduct, which is a substrate for a glycosyltransferase. The sugar and modifying group can be coupled by a zero- or higher-order cross-linking agent. Exemplary bifunctional compounds which can be used for attaching modifying groups to carbohydrate moieties include, but are not limited to, bifunctional poly(ethyleneglycols), polyamides, polyethers, polyesters and the like. General approaches for linking carbohydrates to other molecules are known in the literature. See, for example, Lee et al., *Biochemistry* 28: 1856 (1989); Bhatia et al., *Anal. Biochem.* 178: 408 (1989); Janda et al., *J. Am. Chem. Soc.* 112: 8886 (1990) and Bednarski et al., WO 92/18135. In the discussion that follows, the reactive groups are treated as benign on the sugar moiety of the nascent modified sugar. The focus of the discussion is for clarity of illustration. Those of skill in the art will appreciate that the discussion is relevant to reactive groups on the modifying group as well.

An exemplary strategy involves incorporation of a protected sulfhydryl onto the sugar using the heterobifunctional crosslinker SPDP (n-succinimidyl-3-(2-pyridyldithio)propionate and then deprotecting the sulfhydryl for formation of a disulfide bond with another sulfhydryl on the modifying group.

If SPDP detrimentally affects the ability of the modified sugar to act as a glycosyltransferase substrate, one of an array of other crosslinkers such as 2-iminothiolane or N-succinimidyl S-acetylthioacetate (SATA) is used to form a disulfide bond. 2-iminothiolane reacts with primary amines, instantly incorporating an unprotected sulfhydryl onto the amine-containing molecule. SATA also reacts with primary amines, but incorporates a protected sulfhydryl, which is later deacetaylated using hydroxylamine to produce a free sulfhydryl. In each case, the incorporated sulfhydryl is free to react with other sulfhydryls or protected sulfhydryl, like SPDP, forming the required disulfide bond.

The above-described strategy is exemplary, and not limiting, of linkers of use in the invention. Other crosslinkers are available that can be used in different strategies for crosslinking the modifying group to the peptide. For example, TPCH (S-(2-thiopyridyl)-L-cysteine hydrazide and TPMPH ((S-(2-thiopyridyl)mercapto-propionohydrazide) react with carbohydrate moieties that have been previously oxidized by mild periodate treatment, thus forming a hydrazone bond between the hydrazide portion of the crosslinker and the periodate generated aldehydes. TPCH and TPMPH introduce a 2-pyridylthione protected sulfhydryl group onto the sugar, which can be deprotected with DTT and then subsequently used for conjugation, such as forming disulfide bonds between components.

If disulfide bonding is found unsuitable for producing stable modified sugars, other crosslinkers may be used that incorporate more stable bonds between components. The heterobifunctional crosslinkers GMBS (N-gama-malimidobutyryloxy)succinimide) and SMCC (succinimidyl 4-(N-maleimido-methyl)cyclohexane) react with primary amines, thus introducing a maleimide group onto the component. The maleimide group can subsequently react with sulfhydryls on the other component, which can be introduced by previously mentioned crosslinkers, thus forming a stable thioether bond between the components. If steric hindrance between components interferes with either component's activity or the ability of the modified sugar to act as a glycosyltransferase substrate, crosslinkers can be used which introduce long spacer arms between components and include derivatives of some of the previously mentioned crosslinkers (i.e., SPDP). Thus, there is an abundance of suitable crosslinkers, which are useful; each of which is selected depending on the effects it has on optimal peptide conjugate and modified sugar production.

A variety of reagents are used to modify the components of the modified sugar with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: Enzymes as Drugs. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

Amino-Reactive Groups

In one preferred embodiment, the sites on the cross-linker are amino-reactive groups. Useful non-limiting examples of amino-reactive groups include carbonate esters, N-hydroxysuccinimide (NHS) esters, imidoesters, isocyanates, acylhalides, arylazides, p-nitrophenyl esters, aldehydes, and sulfonyl chlorides.

NHS esters react preferentially with the primary (including aromatic) amino groups of a modified sugar component. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide. Thus, the positive charge of the original amino group is lost.

Imidoesters are the most specific acylating reagents for reaction with the amine groups of the modified sugar components. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained.

Isocyanates (and isothiocyanates) react with the primary amines of the modified sugar components to form stable bonds. Their reactions with sulfhydryl, imidazole, and tyrosyl groups give relatively unstable products.

Acylazides are also used as amino-specific reagents in which nucleophilic amines of the affinity component attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of modified sugar components, but also with sulfhydryl and imidazole groups.

p-Nitrophenyl esters of mono- and dicarboxylic acids are also useful amino-reactive groups. Although the reagent specificity is not very high, $\alpha$- and $\epsilon$-amino groups appear to react most rapidly.

Aldehydes such as glutaraldehyde react with primary amines of modified sugar. Although unstable Schiff bases are formed upon reaction of the amino groups with the aldehydes of the aldehydes, glutaraldehyde is capable of modifying the modified sugar with stable crosslinks. At pH 6-8, the pH of typical crosslinking conditions, the cyclic polymers undergo a dehydration to form $\alpha$-$\beta$ unsaturated aldehyde polymers. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product.

Aromatic sulfonyl chlorides react with a variety of sites of the modified sugar components, but reaction with the amino groups is the most important, resulting in a stable sulfonamide linkage.

Sulfhydryl-Reactive Groups

In another preferred embodiment, the sites are sulfhydryl-reactive groups. Useful, non-limiting examples of sulfhydryl-reactive groups include maleimides, alkyl halides, pyridyl disulfides, and thiophthalimides.

Maleimides react preferentially with the sulfhydryl group of the modified sugar components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryls via disulfide exchange to give mixed disulfides. As a result, pyridyl disulfides are the most specific sulfhydryl-reactive groups.

Thiophthalimides react with free sulfhydryl groups to form disulfides.

Carboxyl-Reactive Residue

In another embodiment, carbodiimides soluble in both water and organic solvent, are used as carboxyl-reactive reagents. These compounds react with free carboxyl groups forming a pseudourea that can then couple to available amines yielding an amide linkage teach how to modify a carboxyl group with carbodiimde (Yamada et al., *Biochemistry* 20: 4836-4842, 1981).

In addition to the use of site-specific reactive moieties, the present invention contemplates the use of non-specific reactive groups to link the sugar to the modifying group. Exemplary non-specific cross-linkers include photoactivatable groups, completely inert in the dark, which are converted to reactive species upon absorption of a photon of appropriate energy. In one preferred embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming crosslinks.

Homobifunctional Crosslinkers Reactive with Primary Amines

Synthesis, properties, and applications of amine-reactive cross-linkers are commercially described in the literature (for reviews of crosslinking procedures and reagents, see above). Many reagents are available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional NHS esters include disuccinimidyl glutarate (DSG), disuccinimidyl suberate (DSS), bis(sulfosuccinimidyl) suberate (BS), disuccinimidyl tartarate (DST), disulfosuccinimidyl tartarate (sulfo-DST), bis-2-(succinimidooxycarbonyloxy) ethylsulfone (BSOCOES), bis-2-(sulfosuccinimidooxy-carbonyloxy)ethylsulfone (sulfo-BSOCOES), ethylene glycolbis(succinimidylsuccinate) (EGS), ethylene glycolbis (sulfosuccinimidylsuccinate) (sulfo-EGS), dithiobis (succinimidyl-propionate (D SP), and dithiobis (sulfosuccinimidylpropionate (sulfo-DSP). Preferred, non-limiting examples of homobifunctional imidoesters include dimethyl malonimidate (DMM), dimethyl succinimidate (DMSC), dimethyl adipimidate (DMA), dimethyl pimelimidate (DMP), dimethyl suberimidate (DMS), dimethyl-3,3'-oxydipropionimidate (DODP), dimethyl-3,3'-(methylenedioxy)dipropionimidate (DMDP), dimethyl-3'-(dimethylenedioxy)dipropionimidate (DDDP), dimethyl-3, 3'-(tetramethylenedioxy)-dipropionimidate (DTDP), and dimethyl-3,3'-dithiobispropionimidate (DTBP).

Preferred, non-limiting examples of homobifunctional isothiocyanates include: p-phenylenediisothiocyanate (DITC), and 4,4'-diisothiocyano-2,2'-disulfonic acid stilbene (DIDS).

Preferred, non-limiting examples of homobifunctional isocyanates include xylene-diisocyanate, toluene-2,4-diisocyanate, toluene-2-isocyanate-4-isothiocyanate, 3-methoxydiphenylmethane-4,4'-diisocyanate, 2,2'-dicarboxy-4,4'-azophenyldiisocyanate, and hexamethylenediisocyanate.

Preferred, non-limiting examples of homobifunctional arylhalides include 1,5-difluoro-2,4-dinitrobenzene (DFDNB), and 4,4'-difluoro-3,3'-dinitrophenyl-sulfone.

Preferred, non-limiting examples of homobifunctional aliphatic aldehyde reagents include glyoxal, malondialdehyde, and glutaraldehyde.

Preferred, non-limiting examples of homobifunctional acylating reagents include nitrophenyl esters of dicarboxylic acids.

Preferred, non-limiting examples of homobifunctional aromatic sulfonyl chlorides include phenol-2,4-disulfonyl chloride, and α-naphthol-2,4-disulfonyl chloride.

Preferred, non-limiting examples of additional amino-reactive homobifunctional reagents include erythritolbiscarbonate which reacts with amines to give biscarbamates.

Homobifunctional Crosslinkers Reactive with Free Sulfhydryl Groups

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional maleimides include bismaleimidohexane (BMH), N,N'-(1,3-phenylene)bismaleimide, N,N'-(1,2-phenylene)bismaleimide, azophenyldimaleimide, and bis(N-maleimidomethyl) ether.

Preferred, non-limiting examples of homobifunctional pyridyl disulfides include 1,4-di-3'-(2'-pyridyldithio)propionamidobutane (DPDPB).

Preferred, non-limiting examples of homobifunctional alkyl halides include 2,2'-dicarboxy-4,4'-diiodoacetamidoazobenzene, α,α'-diiodo-p-xylenesulfonic acid, α,α'-dibromo-p-xylenesulfonic acid, N,N'-bis(b-bromoethyl)benzylamine, N,N'-di(bromoacetyl)phenylthydrazine, and 1,2-di (bromoacetyl)amino-3-phenylpropane.

Homobifunctional Photoactivatable Crosslinkers

Synthesis, properties, and applications of such reagents are described in the literature (for reviews of crosslinking procedures and reagents, see above). Some of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of homobifunctional photoactivatable crosslinker include bis-β-(4-azidosalicylamido)ethyldisulfide (BASED), di-N-(2-nitro-4-azidophenyl)-cystamine-S,S-dioxide (DNCO), and 4,4'-dithiobisphenylazide.

Amino-Reactive HeteroBifunctional Reagents with a Pyridyl Disulfide Moiety

Synthesis, properties, and applications of such reagents are described in the literature (for reviews of crosslinking procedures and reagents, see above). Many of the reagents are commercially available (e.g., Pierce Chemical Company, Rockford, Ill.; Sigma Chemical Company, St. Louis, Mo.; Molecular Probes, Inc., Eugene, Oreg.).

Preferred, non-limiting examples of hetero-bifunctional reagents with a pyridyl disulfide moiety and an amino-reactive NHS ester include N-succinimidyl-3-(2-pyridyldithio) propionate (SPDP), succinimidyl 6-3-(2-pyridyldithio)propionamidohexanoate (LC-SPDP), sulfosuccinimidyl 6-3-(2-pyridyldithio)propionamidohexanoate (sulfo-LCSPDP), 4-succinimidyloxycarbonyl-α-methyl-α-(2-pyridyldithio) toluene (SMPT), and sulfosuccinimidyl 6-α-methyl-α-(2-pyridyldithio)toluamidohexanoate (sulfo-LC-SMPT).

Amino-Reactive HeteroBifunctional Reagents with a Maleimide Moiety

Synthesis, properties, and applications of such reagents are described in the literature. Preferred, non-limiting examples of hetero-bifunctional reagents with a maleimide moiety and an amino-reactive NHS ester include succinimidyl maleimidylacetate (AMAS), succinimidyl 3-maleimidylpropionate (BMPS), N-γ-maleimidobutyryloxysuccinimide ester (GMBS)N-γ-maleimidobutyryloxysulfo succinimide ester (sulfo-GMBS) succinimidyl 6-maleimidythexanoate (EMCS), succinimidyl 3-maleimidylbenzoate (SMB), m-maleimidobenzoyl-N-hydroxysuccinimide ester (MBS), m-maleimidobenzoyl-N-hydroxysulfosuccinimide ester (sulfo-MBS), succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), and sulfosuccinimidyl 4-(p-maleimidophenyl)butyrate (sulfo-SMPB).

Amino-Reactive HeteroBifunctional Reagents with an Alkyl Halide Moiety

Synthesis, properties, and applications of such reagents are described in the literature Preferred, non-limiting examples of hetero-bifunctional reagents with an alkyl halide moiety and an amino-reactive NHS ester include N-succinimidyl-(4-iodoacetyl)aminobenzoate (SIAB), sulfosuccinimidyl-(4-iodoacetyl)aminobenzoate (sulfo-SIAB), succinimidyl-6-(iodoacetyl)aminohexanoate (SIAX), succinimidyl-6-(6-((iodoacetyl)-amino)hexanoylamino)hexanoate (SIAXX), succinimidyl-6-(((4-(iodoacetyl)-amino)-methyl)-cyclohexane-1-carbonyl)aminohexanoate (SIACX), and succinimidyl-4((iodoacetyl)-amino)methylcyclohexane-1-carboxylate (SIAC).

A preferred example of a hetero-bifunctional reagent with an amino-reactive NHS ester and an alkyl dihalide moiety is N-hydroxysuccinimidyl 2,3-dibromopropionate (SDBP). SDBP introduces intramolecular crosslinks to the affinity component by conjugating its amino groups. The reactivity of the dibromopropionyl moiety towards primary amine groups is controlled by the reaction temperature (McKenzie et al., *Protein Chem.* 7: 581-592 (1988)).

Preferred, non-limiting examples of hetero-bifunctional reagents with an alkyl halide moiety and an amino-reactive p-nitrophenyl ester moiety include p-nitrophenyl iodoacetate (NPIA).

Other cross-linking agents are known to those of skill in the art. See, for example, Pomato et al., U.S. Pat. No. 5,965,106. It is within the abilities of one of skill in the art to choose an appropriate cross-linking agent for a particular application.

Cleavable Linker Groups

In yet a further embodiment, the linker group is provided with a group that can be cleaved to release the modifying group from the sugar residue. Many cleaveable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups is commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

Conjugation of Modified Sugars to Peptides

The modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), and U.S. Pat. Nos. 5,352,670, 5,374,541, and 5,545,553.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In an additional preferred embodiment, more than two enzymes are used to assemble the modified glycoprotein of the invention. The enzymes are used to alter a saccharide structure on the peptide at any point either before or after the addition of the modified sugar to the peptide.

In another embodiment, the method makes use of one or more exo- or endoglycosidase. The glycosidase is typically a mutant, which is engineered to form glycosyl bonds rather than cleave them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 30° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g., enzyme concentration, donor concentration, acceptor concentration, temperature, solvent volume), which are optimized for a selected system.

The present invention also provides for the industrial-scale production of modified peptides. As used herein, an industrial scale generally produces at least about 250 mg, preferably at least about 500 mg, and more preferably at least about 1 gram of finished, purified conjugate, preferably after a single reaction cycle, i.e., the conjugate is not a combination the reaction products from identical, consecutively iterated synthesis cycles.

In the discussion that follows, the invention is exemplified by the conjugation of modified sialic acid moieties to a glycosylated peptide. The exemplary modified sialic acid is labeled with m-PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than m-PEG including other water-soluble polymers, therapeutic moieties, and biomolecules.

An enzymatic approach can be used for the selective introduction of m-PEG-ylated or m-PPG-ylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

An acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, GalNAc, Galβ1,3GalNAc, Galβ1,6GlcNAc, Galβ1,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the peptide, e.g., a GalNAc. The method includes incubating the peptide to be modified with a reaction mixture that contains a suitable amount of a galactosyltransferase (e.g., Galβ1,3 or Galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions.

In the discussion that follows, the method of the invention is exemplified by the use of modified sugars having a water-soluble polymer attached thereto. The focus of the discussion is for clarity of illustration. Those of skill will appreciate that the discussion is equally relevant to those embodiments in which the modified sugar bears a therapeutic moiety, biomolecule or the like.

In an exemplary embodiment, an O-linked carbohydrate residue is "trimmed" prior to the addition of the modified sugar. For example a GalNAc-Gal residue is trimmed back to GalNAc. A modified sugar bearing a water-soluble polymer is conjugated to one or more of the sugar residues exposed by the "trimming." In one example, a glycopeptide is "trimmed" and a water-soluble polymer is added to the resulting O-side chain amino acid or glycopeptide glycan via a saccharyl moiety, e.g., Sia, Gal, or GalNAc moiety conjugated to the water-soluble polymer. The modified saccharyl moiety is attached to an acceptor site on the "trimmed" glycopeptide. Alternatively, an unmodified saccharyl moiety, e.g., Gal can be added the terminus of the O-linked glycan.

In another exemplary embodiment, a water-soluble polymer is added to a GalNAc residue via a modified sugar having a galactose residue. Alternatively, an unmodified Gal can be added to the terminal GalNAc residue.

In yet a further example, a water-soluble polymer is added onto a Gal residue using a modified sialic acid.

In another exemplary embodiment, an O-linked glycosyl residue is "trimmed back" to the GalNAc attached to the amino acid. In one example, a water-soluble polymer is added via a Gal modified with the polymer. Alternatively, an unmodified Gal is added to the GalNAc, followed by a Gal with an attached water-soluble polymer. In yet another embodiment, one or more unmodified Gal residue is added to the GalNAc, followed by a sialic acid moiety modified with a water-soluble polymer.

Using the methods of the invention, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, the water-soluble polymer is added to a terminal Gal residue using a polymer modified sialic acid. An appropriate sialyltransferase is used to add a modified sialic acid. The approach is summarized in Scheme 5.

Scheme 5

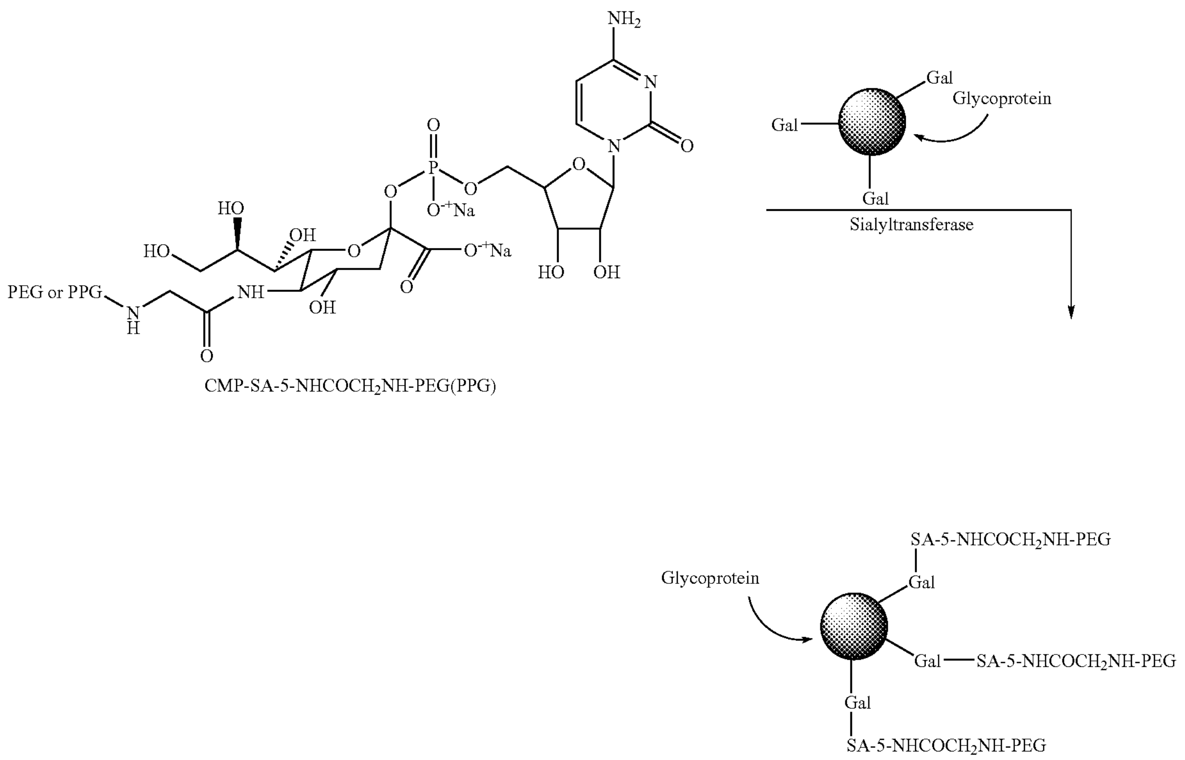

In yet a further approach, summarized in Scheme 6, a masked reactive functionality is present on the sialic acid. The masked reactive group is preferably unaffected by the conditions used to attach the modified sialic acid to the peptide. After the covalent attachment of the modified sialic acid to the peptide, the mask is removed and the peptide is conjugated with an agent such as PEG, PPG, a therapeutic moiety, biomolecule or other agent. The agent is conjugated to the peptide in a specific manner by its reaction with the unmasked reactive group on the modified sugar residue.

Any modified sugar can be used with its appropriate glycosyltransferase, depending on the terminal sugars of the oligosaccharide side chains of the glycopeptide (Table 2). As discussed above, the terminal sugar of the glycopeptide required for introduction of the PEG-ylated or PPG-ylated structure can be introduced naturally during expression or it can be produced post expression using the appropriate glycosidase(s), glycosyltransferase(s) or mix of glycosidase(s) and glycosyltransferase(s).

Scheme 6

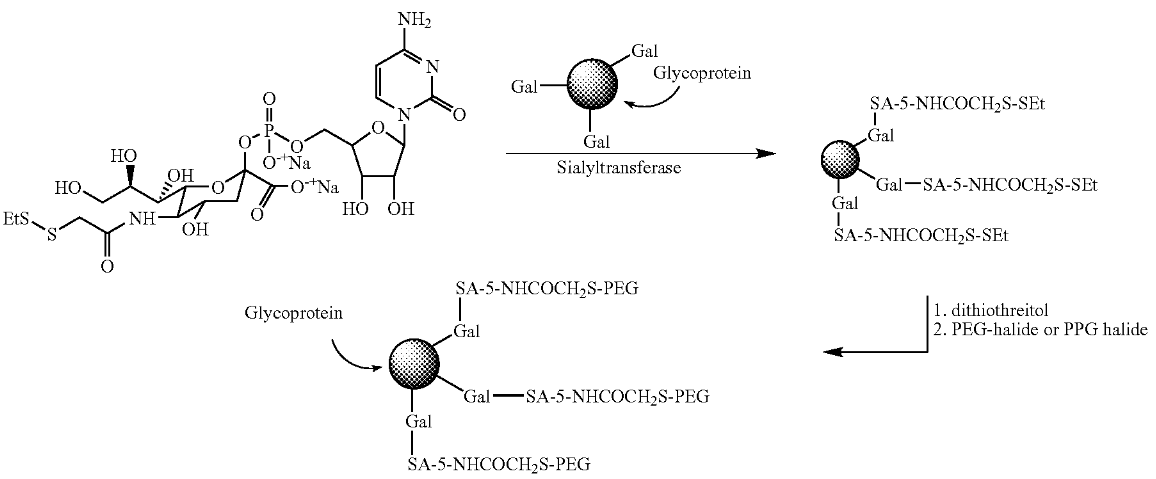

TABLE 2

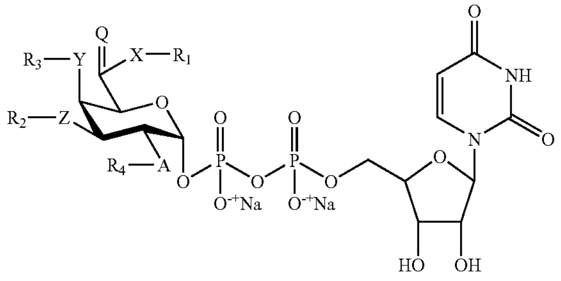

UDP-galactose-derivatives

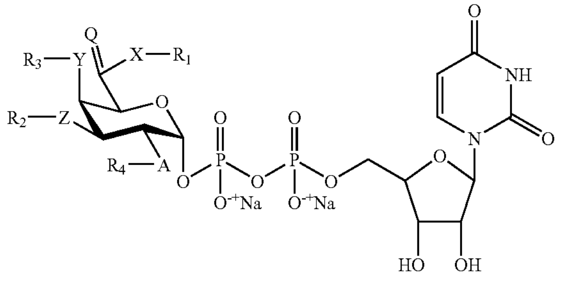

UDP-galactosamine-derivatives
(when A = NH, $R_4$ may be acetyl)

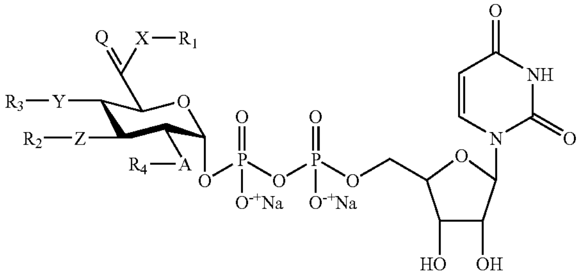

UDP-Glucose-derivatives

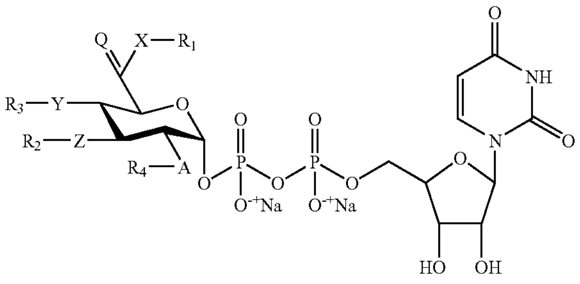

UDP-Glucosamine-derivatives
(when A = NH, $R_4$ may be acetyl)

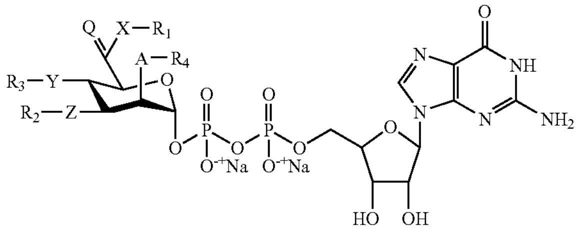

GDP-Mannose-derivatives

TABLE 2-continued

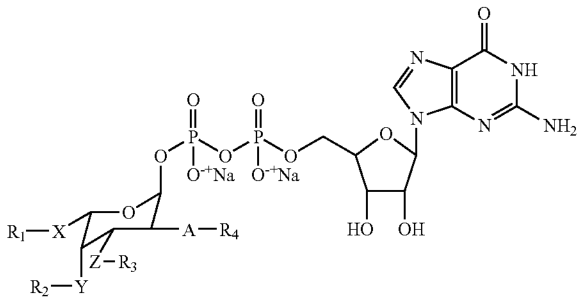

GDP-fucose-derivatives

X = O, NH, S, $CH_2$, N—$(R_{1-5})_2$.
Y = X; Z = X; A = X; B = X.
Q = $H_2$, O, S, NH, N—R.
R, $R_{1-4}$ = H, Linker-M, M.
M = Ligand of interest
Ligand of interest = acyl-PEG, acyl-PPG, alkyl-PEG, acyl-alkyl-PEG, acyl-alkyl-PEG, carbamoyl-PEG, carbamoyl-PPG, PEG, PPG, acyl-aryl-PEG, acyl-aryl-PPG, aryl-PEG, aryl-PPG, Mannose-6-phosphate, heparin, heparan, SLex, Mannose, FGF, VFGF, protein, chondroitin, keratan, dermatan, albumin, integrins, peptides, etc.

In a further exemplary embodiment, UDP-galactose-PEG is reacted with bovine milk β1,4-galactosyltransferase, thereby transferring the modified galactose to the appropriate terminal N-acetylglucosamine structure. The terminal GlcNAc residues on the glycopeptide may be produced during expression, as may occur in such expression systems as mammalian, insect, plant or fungus, but also can be produced by treating the glycopeptide with a sialidase and/or glycosidase and/or glycosyltransferase, as required.

In another exemplary embodiment, a GlcNAc transferase, such as GNT1-5, is utilized to transfer PEGylated-GlcN to a terminal mannose residue on a glycopeptide. In a still further exemplary embodiment, an the N- and/or O-linked glycan structures are enzymatically removed from a glycopeptide to expose an amino acid or a terminal glycosyl residue that is subsequently conjugated with the modified sugar. For example, an endoglycanase is used to remove the N-linked structures of a glycopeptide to expose a terminal GlcNAc as a GlcNAc-linked-Asn on the glycopeptide. UDP-Gal-PEG and the appropriate galactosyltransferase is used to introduce the PEG- or PPG-galactose functionality onto the exposed GlcNAc.

In an alternative embodiment, the modified sugar is added directly to the peptide backbone using a glycosyltransferase known to transfer sugar residues to the peptide backbone. This exemplary embodiment is set forth in Scheme 7. Exemplary glycosyltransferases useful in practicing the present invention include, but are not limited to, GalNAc transferases (GalNAc T1-20), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the polypeptide chain.

Scheme 7

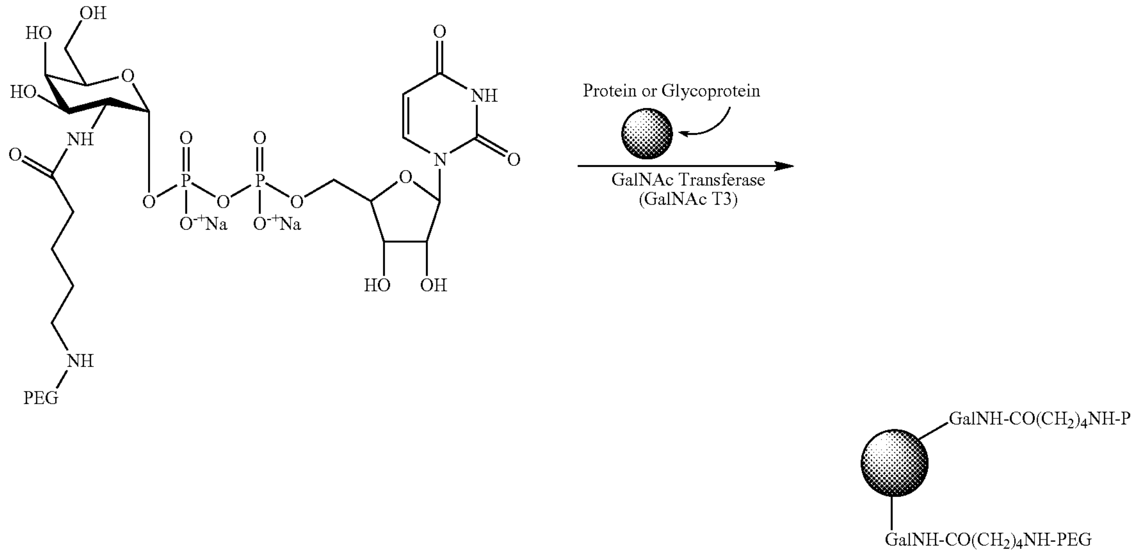

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" (e.g., sialylate) sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the peptide. Further elaboration of the modified sugar-peptide conjugate is within the scope of the invention.

Enzymes

Glycosyltransferases

Glycosyltransferases catalyze the addition of activated sugars (donor NDP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-$NAG_2Glc_3Man_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize the modified sugar as a sugar donor. Examples of such enzymes include Leloir pathway glycosyltransferase, such as galactosyltransferase, N-acetylglucosaminyltransferase, N-acetylgalactosaminyltransferase, fucosyltransferase, sialyltransferase, mannosyltransferase, xylosyltransferase, glucurononyltransferase and the like.

For enzymatic saccharide syntheses that involve glycosyltransferase reactions, glycosyltransferase can be cloned, or isolated from any source. Many cloned glycosyltransferases are known, as are their polynucleotide sequences. See, e.g., "The WWW Guide To Cloned Glycosyltransferases" (www.vei.co.uk/TGN/gt_guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, and oligosaccharyltransferases. Suitable glycosyltransferases include those obtained from eukaryotes, as well as from prokaryotes.

DNA encoding the enzyme glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotide probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotide primers being produced from the glycosyltransferases gene sequence. See, U.S. Pat. No. 4,683,195 to Mullis et al. and U.S. Pat. No. 4,683,202 to Mullis.

The glycosyltransferases enzyme may be synthesized in host cells transformed with vectors containing DNA encoding the glycosyltransferases enzyme. A vector is a replicable DNA construct. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4)GlcNAcβ-group in an oligosaccharide glycoside. Suitable fucosyltransferases for this reaction include the Galβ(1→3,4)GlcNAcβ1-α(1→3,4)fucosyltransferase (FTIII E.C. No. 2.4.1.65), which was first characterized from human milk (see, Palcic, et al., *Carbohydrate Res.* 190:1-11 (1989); Prieels, et al., *J. Biol. Chem.* 256: 10456-10463 (1981); and Nunez, et al., *Can. J. Chem.* 59: 2086-2095 (1981)) and the Galβ(1→4)GlcNAcβ-αfucosyltransferases (FTIV, FTV, FTVI) which are found in human serum. FTVII (E.C. No. 2.4.1.65), a sialyl α(2→3)Galβ((1→3)GlcNAcβ fucosyltransferase, has also been characterized. A recombinant form of the Galβ(1→3,4) GlcNAcβ-α(1→3,4)fucosyltransferase has also been characterized (see, Dumas, et al., *Bioorg Med. Letters* 1: 425-428 (1991) and Kukowska-Latallo, et al., *Genes and Development* 4: 1288-1303 (1990)). Other exemplary fucosyltransferases include, for example, α1,2 fucosyltransferase (E.C. No. 2.4.1.69). Enzymatic fucosylation can be carried out by the methods described in Mollicone, et al., *Eur. J. Biochem.* 191: 169-176 (1990) or U.S. Pat. No. 5,374,655. Cells that are used to produce a fucosyltransferase will also include an enzymatic system for synthesizing GDP-fucose.

Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBank j04989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et al., *Immunogenetics* 41: 101-105 (1995)). Another suitable α1,3 galactosyltransferase is that which is involved in synthesis of the blood group B antigen (EC 2.4.1.37, Yamamoto et al., *J. Biol. Chem.* 265: 1146-1151 (1990) (human)).

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. J. Biochem.* 183: 211-217 (1989)), human (Masri et al., *Biochem. Biophys. Res. Commun.* 157: 657-663 (1988)), murine (Nakazawa et al., *J. Biochem.* 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe*, Chapell et al., *Mol. Biol. Cell* 5: 519-528 (1994)).

The production of proteins such as the enzyme GalNAc $T_{I-XIV}$ from cloned genes by genetic engineering is well known. See, e.g., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol. Chem.* 257: 13845 (1982) and Wen et al., *J. Biol. Chem.* 267: 21011 (1992). Another exemplary α2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-β-1,4-GlcNAc α-2,6 sialyltransferase (See, Kurosawa et al. *Eur. J. Biochem.* 219: 375-381 (1994)).

Preferably, for glycosylation of carbohydrates of glycopeptides the sialyltransferase will be able to transfer sialic acid to the sequence Galβ1,4GlcNAc-, the most common penultimate sequence underlying the terminal sialic acid on fully sialylated carbohydrate structures (see, Table 3).

TABLE 3

Sialyltransferases which use the Galβ1,4GlcNAc sequence as an acceptor substrate

| Sialyl-transferase | Source | Sequence(s) formed | Ref. |
|---|---|---|---|
| ST6Gal I | Mammalian | NeuAcα2,6Galβ1,4GlCNAc- | 1 |
| ST3Gal III | Mammalian | NeuAcα2,3Galβ1,4GlCNAc-<br>NeuAcα2,3Galβ1,3GlCNAc- | 1 |
| ST3Gal IV | Mammalian | NeuAcα2,3Galβ1,4GlCNAc-<br>NeuAcα2,3Galβ1,3GlCNAc- | 1 |
| ST6Gal II | Mammalian | NeuAcα2,6Galβ1,4GlCNA | |
| ST6Gal II | photobacterium | NeuAcα2,6Galβ1,4GlCNAc- | 2 |

TABLE 3-continued

Sialyltransferases which use the Galβ1,4GlcNAc sequence as an acceptor substrate

| Sialyl-transferase | Source | Sequence(s) formed | Ref. |
|---|---|---|---|
| ST3Gal V | *N. meningitides* *N. gonorrhoeae* | NeuAcα2,3Galβ1,4GlCNAc- | 3 |

1) Goochee et al., Bio/Technology 9: 1347-1355 (1991)
2) Yamamoto et al., J. Biochem. 120: 104-110 (1996)
3) Gilbert et al., J. Biol. Chem. 271: 28271-28276 (1996)

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc or Galβ1,4GlcNAc glycoside (see, e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3Gal III.

Other exemplary sialyltransferases of use in the present invention include those isolated from *Campylobacter jejuni*, including the α(2,3). See, e.g., WO99/49051.

Sialyltransferases other than those listed in Table 3, are also useful in an economic and efficient large-scale process for sialylation of commercially important glycopeptides. As a simple test to find out the utility of these other enzymes, various amounts of each enzyme (1-100 mU/mg protein) are reacted with asialo-$\alpha_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides or glycopeptides, or N-linked oligosaccharides enzymatically released from the peptide backbone can be used in place of asialo-$\alpha_1$ AGP for this evaluation. Sialyltransferases with the ability to sialylate N-linked oligosaccharides of glycopeptides more efficiently than ST6Gal I are useful in a practical large-scale process for peptide sialylation (as illustrated for ST3Gal III in this disclosure).

Other Glycosyltransferases

One of skill in the art will understand that other glycosyltransferases can be substituted into similar transferase cycles as have been described in detail for the sialyltransferase. In particular, the glycosyltransferase can also be, for instance, glucosyltransferases, e.g., Alg8 (Stagljov et al., *Proc. Natl. Acad. Sci. USA* 91: 5977 (1994)) or Alg5 (Heesen et al., *Eur. J. Biochem.* 224: 71 (1994)).

N-acetylgalactosaminyltransferases are also of use in practicing the present invention. Suitable N-acetylgalactosaminyltransferases include, but are not limited to, α(1,3) N-acetylgalactosaminyltransferase, β(1,4) N-acetylgalactosaminyltransferases (Nagata et al., *J. Biol. Chem.* 267: 12082-12089 (1992) and Smith et al., *J Biol. Chem.* 269: 15162 (1994)) and polypeptide N-acetylgalactosaminyltransferase (Homa et al., *J. Biol. Chem.* 268: 12609 (1993)). Suitable N-acetylglucosaminyltransferases include GnTI (2.4.1.101, Hull et al., *BBRC* 176: 608 (1991)), GnTII, GnTIII (Ihara et al., *J. Biochem.* 113: 692 (1993)), GnTIV, and GnTV (Shoreiban et al., *J. Biol. Chem.* 268: 15381 (1993)), O-linked N-acetylglucosaminyltransferase (Bierhuizen et al., *Proc. Natl. Acad. Sci. USA* 89: 9326 (1992)), N-acetylglucosamine-1-phosphate transferase (Rajput et al., *Biochem J.* 285: 985 (1992), and hyaluronan synthase.

Mannosyltransferases are of use to transfer modified mannose moieties. Suitable mannosyltransferases include α(1,2) mannosyltransferase, α(1,3) mannosyltransferase, α(1,6) mannosyltransferase, β(1,4) mannosyltransferase, Dol-P-Man synthase, OCh1, and Pmt1 (see, Kornfeld et al., *Annu. Rev. Biochem.* 54: 631-664 (1985)).

Xylosyltransferases are also useful in the present invention. See, for example, Rodgers, et al., Biochem. J., 288:817-822 (1992); and Elbain, et al., U.S. Pat. No., 6,168,937. Other suitable glycosyltransferase cycles are described in Ichikawa et al., *JACS* 114: 9283 (1992), Wong et al., *J. Org. Chem.* 57: 4343 (1992), and Ichikawa et al. in CARBOHYDRATES AND CARBOHYDRATE POLYMERS. Yaltami, ed. (ATL Press, 1993).

Prokaryotic glycosyltransferases are also useful in practicing the invention. Such glycosyltransferases include enzymes involved in synthesis of lipooligosaccharides (LOS), which are produced by many gram negative bacteria. The LOS typically have terminal glycan sequences that mimic glycoconjugates found on the surface of human epithelial cells or in host secretions (Preston et al., *Critical Reviews in Microbiology* 23(3): 139-180 (1996)). Such enzymes include, but are not limited to, the proteins of the rfa operons of species such as *E. coli* and *Salmonella typhimurium*, which include a β1,6 galactosyltransferase and a β1,3 galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an β1,2-glucosyltransferase (rfaJ)(Swiss-Prot Accession No. P27129 (*E. coli*) and Swiss-Prot Accession No. P19817 (*S. typhimurium*)), and an β1,2-N-acetylglucosaminyltransferase (rfaK)(EMBL Accession No. U00039 (*E. coli*). Other glycosyltransferases for which amino acid sequences are known include those that are encoded by operons such as rfaB, which have been characterized in organisms such as *Klebsiella pneumoniae, E. coli, Salmonella typhimurium, Salmonella enterica, Yersinia enterocolitica, Mycobacterium leprosum*, and the rh1 operon of *Pseudomonas aeruginosa.*

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens *Neisseria gonorrhoeae* and *N. meningitidis* (Scholten et al., *J. Med. Microbiol.* 41: 236-243 (1994)). The genes from *N. meningitidis* and *N. gonorrhoeae* that encode the glycosyltransferases involved in the biosynthesis of these structures have been identified from *N. meningitidis* immunotypes L3 and L1 (Jennings et al., *Mol. Microbiol.* 18: 729-740 (1995)) and the *N. gonorrhoeae* mutant F62 (Gotshlich, *J. Exp. Med.* 180: 2181-2190 (1994)). In *N. meningitidis*, a locus consisting of three genes, lgtA, lgtB and lg E, encodes the glycosyltransferase enzymes required for addition of the last three of the sugars in the lacto-N-neotetraose chain (Wakarchuk et al., *J. Biol. Chem.* 271: 19166-73 (1996)). Recently the enzymatic activity of the lgtB and lgtA gene product was demonstrated, providing the first direct evidence for their proposed glycosyltransferase function (Wakarchuk et al., *J. Biol. Chem.* 271(45): 28271-276 (1996)). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an lgtC gene (Jennings et al., (1995), supra.). *Neisseria* glycosyltransferases and associated genes are also described in U.S. Pat. No. 5,545,553 (Gotschlich). Genes for α1,2-fucosyltransferase and α1,3-fucosyltransferase from *Helicobacter pylori* has also been characterized (Martin et al., *J. Biol. Chem.* 272: 21349-21356 (1997)). Also of use in the present invention are the glycosyltransferases of *Campylobacter jejuni* (see, for example, afmb.cnrs-mrs.fr/~pedro/CAZY/gtf_42.html).

Sulfotransferases

The invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., *J. Biol. Chem.* 270:18575-18580 (1995); GenBank Accession No. D49915), glycosaminoglycan N-acetylglucosamine N-deacetylase/N-sulphotransferase 1 (Dixon et al., *Genomics* 26: 239-241 (1995); UL18918), and glycosaminoglycan N-acetylglucosamine N-deacetylase/N-sulphotransferase 2 (murine cDNA described in Orellana et al., *J. Biol. Chem.* 269: 2270-2276 (1994) and Eriksson et al., *J. Biol. Chem.* 269: 10438-10443 (1994); human cDNA described in GenBank Accession No. U2304).

Cell-Bound Glycosyltransferases

In another embodiment, the enzymes utilized in the method of the invention are cell-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for solubilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, Molecular Approaches to Supracellular Phenomena, 1990).

Methods have been developed to alter the glycosyltransferases expressed by cells. For example, Larsen et al., *Proc. Natl. Acad. Sci. USA* 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose:.β.-D-galactosyl-1,4-N-acetyl-D-glucosaminide α-1,3-galactosyltransferase was transfected into COS-1 cells. The transfected cells were then cultured and assayed for α1-3 galactosyltransferase activity.

Francisco et al., *Proc. Natl. Acad. Sci. USA* 89: 2713-2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning.

Fusion Proteins

In other exemplary embodiments, the methods of the invention utilize fusion proteins that have more than one enzymatic activity that is involved in synthesis of a desired glycopeptide conjugate. The fusion polypeptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar that is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. In other embodiments the fusion protein includes the catalytically active domains of two or more glycosyltransferases. See, for example, U.S. Pat. No. 5,641,668. The modified glycopeptides of the present invention can be readily designed and manufactured utilizing various suitable fusion proteins (see, for example, PCT Patent Application PCT/CA98/01180, which was published as WO 99/31224 on Jun. 24, 1999.)

Immobilized Enzymes

In addition to cell-bound enzymes, the present invention also provides for the use of enzymes that are immobilized on a solid and/or soluble support. In an exemplary embodiment, there is provided a glycosyltransferase that is conjugated to a PEG via an intact glycosyl linker according to the methods of the invention. The PEG-linker-enzyme conjugate is optionally attached to solid support. The use of solid supported enzymes in the methods of the invention simplifies the work up of the reaction mixture and purification of the reaction product, and also enables the facile recovery of the enzyme. The glycosyltransferase conjugate is utilized in the methods of the invention. Other combinations of enzymes and supports will be apparent to those of skill in the art.

Glycosylation by Recombinant Methods

Glycosylation of a mutant human growth hormone may also be accomplished intracellularly by recombinant means. A polynucleotide sequence encoding a mutant human growth hormone, which comprises at least one newly introduced N- or O-linked glycosylation site, may be transfected into a suitable host cell line, e.g., a eukaryotic cell line derived from yeast, insect, or mammalian origin. The mutant human growth hormone recombinantly produced from such a cell line is glycosylated by the host cell glycosylation machinery.

Purification of Glycosylated Mutant hGH

The glycosylated human growth hormone produced by the above processes is preferably purified before use. Standard, well known techniques such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein.

If the glycosylated mutant human growth hormone is produced intracellularly, as a first step, the particulate debris, either host cells or lysed fragments, is removed, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, SP-Sepharose, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

A glycosylated mutant human growth hormone produced in culture is usually isolated by initial extraction from cells, cell lysate, culture media, etc., followed by one or more concentration, salting-out, aqueous ion-exchange, or size-exclusion chromatography steps. Additionally, the glycoprotein may be purified by affinity chromatography. Finally, HPLC may be employed for final purification steps.

A protease inhibitor, e.g., methylsulfonylfluoride (PMSF) may be included in any of the foregoing steps to inhibit proteolysis and antibiotics may be included to prevent the growth of adventitious contaminants.

In some cases, supernatants from systems that produce the glycosylated human growth hormone of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Also, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a glycosylated mutant human growth hormone. Some or all of the foregoing purification steps, in various combinations, can also be employed to provide a glycoprotein.

The glycosylated mutant human growth hormone of the invention resulting from a large-scale fermentation may be purified by methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography, may be utilized to purify the glycoprotein.

Functional Assays for the Mutant hGH

Following the production and, preferably, purification of a glycosylated mutant human growth hormone, the biological functions of the glycoprotein are tested using several methods known in the art. The functional assays are based on various characteristics of human growth hormone, such as its specific binding to human growth hormone receptor, activation of the hGH receptor, and its activity in promoting cell growth. In each assay, wild-type human growth hormone is included as a positive control.

A radioreceptor binding assay can be carried out to measure the binding between a radio-labeled hGH receptor and a mutant human growth hormone of the present invention. Detailed description for such an assay can be found in the literature, e.g., Tsushima et al., *J. Clin. Endocrinol. Metab.,* 37: 334-337 (1973); Chin et al., *Endocr. Meta.* 37: 334 (1973); and U.S. Pat. Nos. 4,871,835, 5,079,230.

The ability of a mutant human growth hormone to promote cell growth is assessed by methods such as the tibia test (Parlow et al., *Endocrinology* 77: 1126 (1965); U.S. Pat. No. 4,871,835). Briefly, rats are hypophysectomized at 28-30 days of age and kept for 10-14 days without treatment. Human growth hormone mutants derived from recombinant source is then given to the rats by daily subcutaneous injections. The animals are sacrificed on the sixth day, their foreleg knee bones taken out and the width of the epiphyseal plates measured. The weight of these rats at the start of the experiment and before being sacrificed is also monitored and compared among different groups receiving daily injections of the mutant human growth hormone at different concentrations.

Furthermore, the biological activity of a mutant human growth hormone can be demonstrated in its ability to cause hGH-dependent tyrosine phosphorylation in IM-9 cells, which are derived from a clone of human lymphoblastoma and express human growth hormone receptor on the cell surface. Other cell types such as MB-2 cells may also be suitable for hGH functional assays. The level of tyrosine phosphorylation of cellular proteins upon exposure to the mutant human growth hormone is shown by a monoclonal antibody against phosphorylated tyrosine, as described by Silva et al., *Endocrinology,* 132: 101 (1993) and U.S. Pat. No. 6,238,915.

Pharmaceutical Composition and Administration

The glycosylated mutant human growth hormone having desired oligosaccharide determinants described above can be used as therapeutics for treating a variety of diseases and conditions related to deficiency in growth hormone. Growth-related conditions that can be treated with the mutant human growth hormone of the present invention include: dwarfism, short-stature in children and adults, cachexia/muscle wasting, general muscular atrophy, and sex chromosome abnormality (e.g., Turner's Syndrome). Other conditions may be treated using the mutant hGH of the present invention include: short-bowel syndrome, lipodystrophy, osteoporosis, uraemaia, burns, female infertility, bone regeneration, general diabetes, type II diabetes, osteo-arthritis, chronic obstructive pulmonary disease (COPD), and insomia. The mutant hGH of the invention may also be used to promote various healing processes, e.g., general tissue regeneration, bone regeneration, and wound healing, or as a vaccine adjunct. Thus, the present invention also provides pharmaceutical compositions comprising an effective amount of glycosylated mutant human growth hormone, which is produced according to the methods described above.

Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions are intended for parenteral, intranasal, topical, oral, or local administration, such as by subcutaneous injection, aerosol inhalation, or transdermal adsorption, for prophylactic and/or therapeutic treatment. Commonly, the pharmaceutical compositions are administered parenterally, e.g., subcutaneously or intravenously. Thus, the invention provides compositions for parenteral administration which comprise the glycosylated mutant human growth hormone dissolved or suspended in an acceptable carrier, preferably an aqueous carrier, e.g., water, buffered water, saline, PBS and the like. The compositions may also contain detergents such as Tween 20 and Tween 80; stablizers such as mannitol, sorbitol, sucrose, and trehalose; and preservatives such as EDTA and m-cresol. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 and 8.

The compositions containing the glycosylated mutant human growth hormone can be administered for prophylactic and/or therapeutic treatments. In therapeutic applications, compositions are administered to a patient already suffering from a disease or condition related to growth hormone deficiency, in an amount sufficient to cure or at least partially arrest the symptoms of the disease and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of glycosylated mutant human growth hormone per day for a 70 kg patient, with dosages of from about 5 mg to about 200 mg of the compounds per day being more commonly used.

In prophylactic applications, compositions containing the glycosylated mutant human growth hormone of the invention are administered to a patient susceptible to or otherwise at risk of a particular disease. Such an amount is defined to be a "prophylactically effective dose." In this use, the precise amounts again depend on the patient's state of health and weight, but generally range from about 0.1 mg to about 1,000 mg per 70 kilogram patient, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of the glycosylated mutant human growth hormone of this invention sufficient to effectively treat the patient.

EXAMPLES

The following examples are provided by way of illustration only and not by way of limitation. Those of skill in the art will readily recognize a variety of non-critical parameters that could be changed or modified to yield essentially similar results.

Example 1

Human growth hormone occurs in a variety of different isoforms and different amino acid sequences. The two best characterized forms include placental derived hGH, which is also known as GH-V (PDB P01242) and pituitary derived hGH, which is also known as somatotropin or GH-N (P01241); see FIG. 1. The pituitary derived hGH is not glycosylated and is produced in *Escherichia coli* as a therapeutic. The placental derived hGH (GH-V) has one N-glycosylation site at amino acid 140 (see Table 4 and FIG. 1, see arrow).

TABLE 4

| Human Growth Hormone (GH-V), Placenta Derived; P01242 (SEQ ID NO:2) |
|---|
| fptiplsrlfdnamlrarrlyqlaydtyqefeeayilkeqkysflqnpqtslcfsesiptpsnrvktqqksnle |
| llrisllliqswlepvqllrsvfanslvygasdsnvyrhlkdleegiqtlmwrledgsprtgqif**nqs**yskfdt |
| kshnddallknygllycfrkdmdkvetflrivqcrsvegscgf ↑ |

Figure 2:
FIG. 2 is the crystal structure depiction of a glycosylated GH-N mutant hGH (Lys140 to Asn140) and its receptor polypeptide.

The pituitary derived hGH (GH-N) can be modified at amino acid position 140 to introduce an N-linked glycosylation site by mutating the nucleotide sequence encoding this polypeptide so that instead of encoding the wild-type lysine (abbreviated as "k" at amino acid 140 of the GH-N polypeptide sequence in Table 5 and FIG. 1, see arrow), the nucleotide sequence will encode an asparagine (abbreviated "n") at amino acid position 140 of GH-N (see also FIG. 2).

TABLE 5

| Human Growth Hormone (GH-N), Pituitary Derived; P01241 (SEQ ID NO:1) |
|---|
| fptiplsrlfdnamlrahrlhqlafdtyqefeeayipkeqkysflqnpqtslcfsesiptpsnreetqqksnle |
| llrisllliqswlepvqflrsvfanslvygasdsnvydllkdleegiqtlmgrledgsprtgqif**k**qtyskfdt |
| nshnddallknygllycfrkdmdkvetflrivqcrsvegscgf ↑ |

Figure 3:
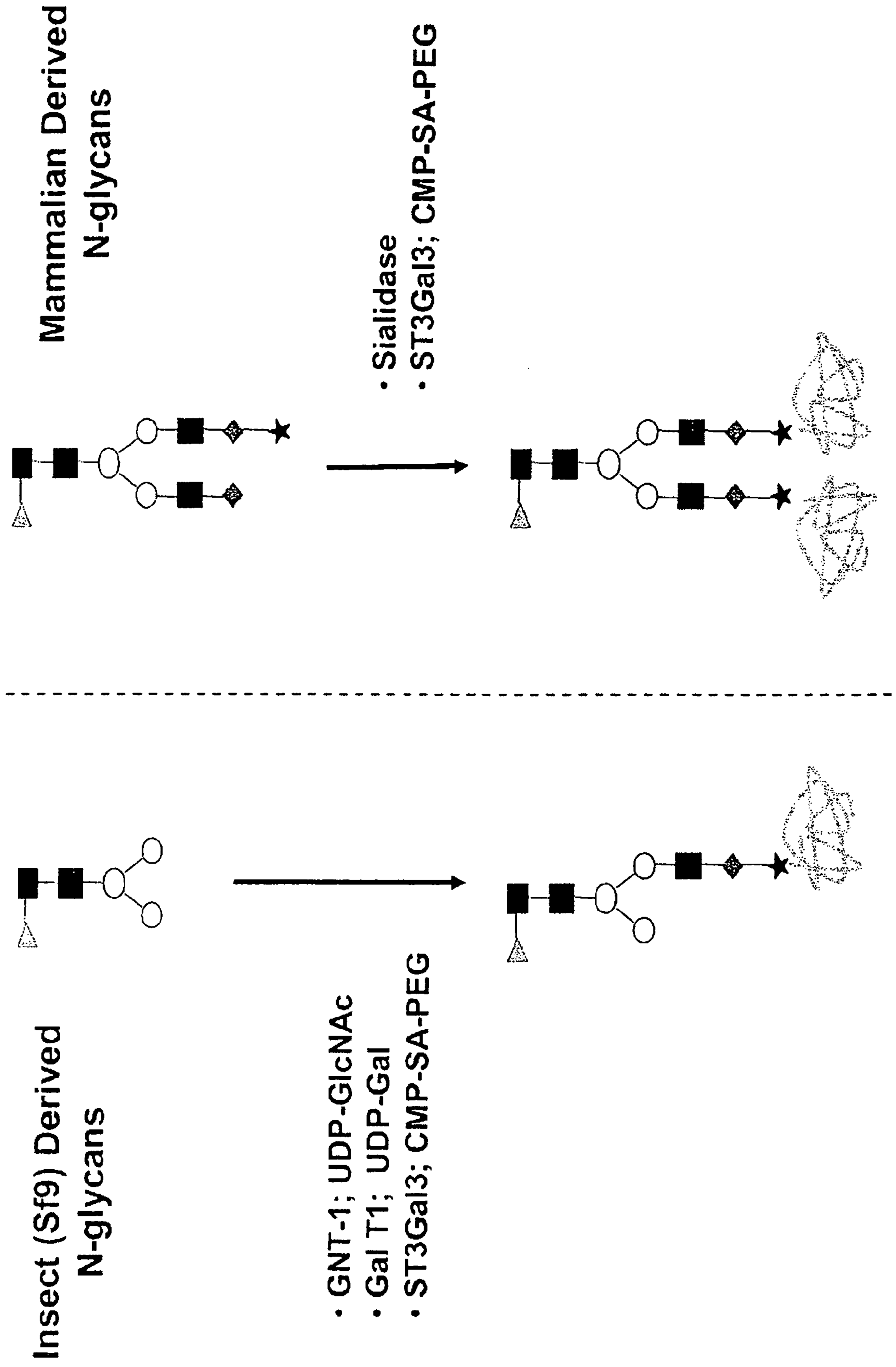
FIG. 3 are glycoPEGylation schemes for insect cell and mammalian cell produced hGH N-linked glycan mutants.

This mutated pituitary derived hGH, regardless of the expression system used to produce this polypeptide, can then be glycosylated or glycoconjugated (see WO 03/31464, incorporated herein by reference). Preferably, the mutated pituitary derived hGH is glycoPEGylated, wherein a polyethylene glycol (PEG) moiety is conjugated to the mutated pituitary derived hGH polypeptide via a glycosyl linkage (see WO 03/31464, incorporated herein by reference). FIG. 3 describes the GlycoPEGylation of an hGH N-linked glycan mutant produced in either Sf9 insect cells or mammalian cells. GlycoPEGylation of the mutated pituitary derived hGH is expected to result in improved biophysical properties that may include but are not limited to improved half-life, improved area under the curve (AUC) values, reduced clearance, and reduced immunogenicity.

Example 2

Figure 4:
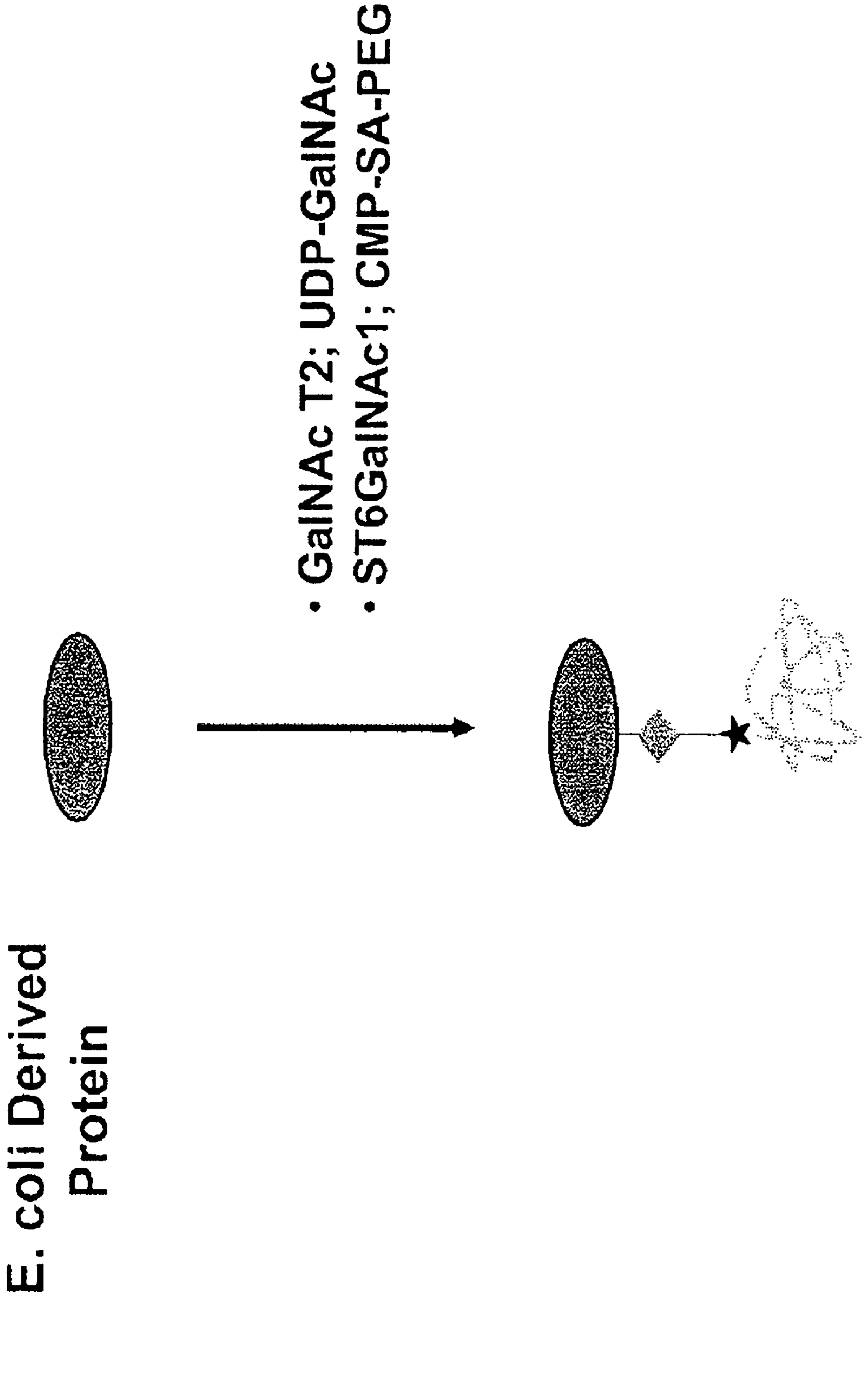
FIG. 4 shows the glycoPEGylation of an *Escherichia coli* produced hGH O-linked glycan mutant.

An alternative approach is to create an O-linked glycosylation site into the pituitary derived hGH polypeptide. This O-linked glycosylation site may then be used as a site on which the mutated hGH polypeptide can be glycoPEGylated using a $GalNAcT_2$ enzyme or the like. One or more additional transferases may then be used to add glycans or glycoconjugates to that site. Preferably, the mutated pituitary derived hGH polypeptide is glycoPEGylated. FIG. 4 describes the glycoPEGylation of an hGH O-linked glycan mutant produced in *Escherichia coli.*

Example 3

Figure 5:
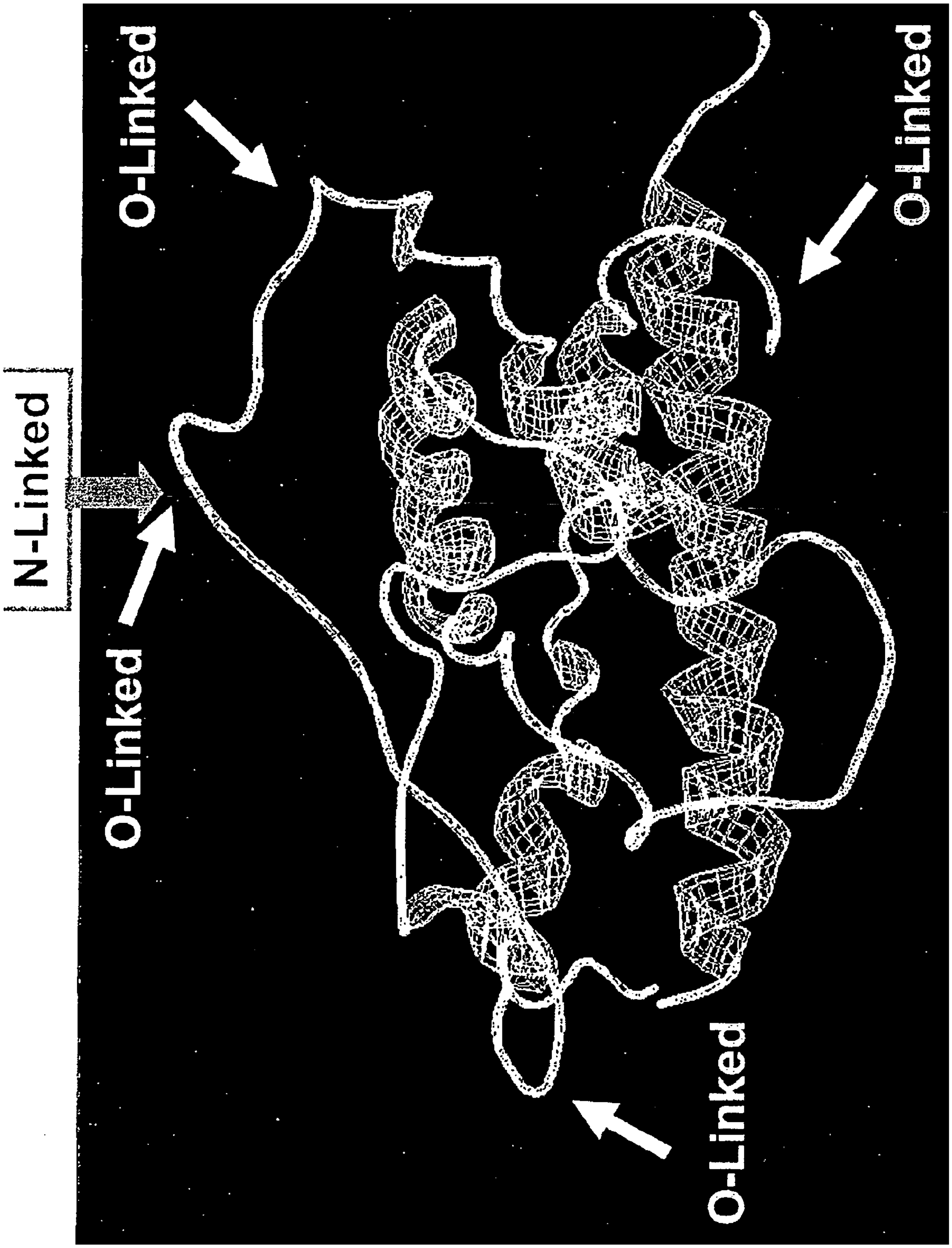
FIG. 5 displays alternate mutants of GH-N to introduce glycosylation sites. The arrows indicate the protein loop regions of GH-N into which a glycosylation site may be introduced.

As identified by the crystal structure of hGH and its receptor, the protein loop regions on pituitary derived hGH are best suited for mutation to introduce a glycosylation site (FIG. 5). Specifically, the nucleotide sequence that encodes amino acids 1-6 (FPTIPL; SEQ ID NO:10), amino acids 48-52 (PQTSL; SEQ ID NO:11), amino acids 59-64 (PTPSNR; SEQ ID NO:12), amino acids 133-139 (PRTGQIF; SEQ ID NO:13), amino acids 133-145 (PRTGQIFKQTYSK; SEQ ID NO:14), or amino acids 139-142 (FKQT; SEQ ID NO:15) of the wild-type pituitary derived hGH amino acid sequence (see Table 5 and FIG. 1) can be mutated so that either an N-linked or an O-linked glycosylation site is introduced into the resulting mutated pituitary-derived hGH polypeptide.

FIG. 6 illustrates six (6) of these introduced O-linked glycosylation sites. The arrows in FIG. 6 each represent the threonine residue on which O-linked glycosylation will occur in the GH-N O-linked glycan hGH mutant.

FIG. 7 and FIG. 8 each illustrates two additional GH-N O-linked glycan hGH mutants.

Example 4

This example describes amino acid sequence mutations introducing O-linked glycosylation sites, i.e., serine or threonine residues, into a preferably proline-containing site of a wild-type human growth hormone sequence or any modified version thereof.

1. N-Terminal Mutations

In the N-terminal mutants, the N-terminus of a wild-type hGH, $FP^2TIP^5LS$; SEQ ID NO:16, is replaced with either $MXnTP^2TIP^5LS$ or $MAPTSSXnP^2TIP^5LS$. Preferred examples include:

| | |
|---|---|
| MVTPTIPLS; | SEQ ID NO:17 |
| MQTPTIPLS; | SEQ ID NO:18 |
| MAPTSSPTIPLS; | SEQ ID NO:19 |
| MAPTSSSPTIPLS; (IL-2 N-terminus) | SEQ ID NO:20 |
| MPTTFPTIPLS; | SEQ ID NO:21 |
| MPTSSPTIPLS; | SEQ ID NO:22 |
| MPTSSSPTIPLS; | SEQ ID NO:23 |

2. Internal Mutation Site 1

In this type of mutants, the N-terminus of a wild-type hGH, $FP^2TIP^5LS$; SEQ ID NO:24, is replaced with $ZmP^2TXnBoP^5LS$. Preferred mutations include:

| | |
|---|---|
| MFPTQIPLS; | SEQ ID NO:25 |
| MFPTSIPLS; | SEQ ID NO:26 |
| MFPTSSPLS; | SEQ ID NO:27 |
| MTPTQIPLS; | SEQ ID NO:28 |
| MFPTTTPLS; | SEQ ID NO:29 |

3. Internal Mutation Site 2

In this type of mutants, the amino acid sequence surrounding $P^{37}$, $AYIP^{37}KEQKY$; SEQ ID NO:30, is replace with $AZmJqP^{37}OrXnBo\Delta pY$, where at least one of Z, J, O, X, and B is independently selected from either Thr or Ser; Δ may include Lys (K) and X may be Asp (D). Preferred examples include:

| | |
|---|---|
| $AYIP^{37}TQGAY$; | SEQ ID NO:31 |
| $AYIP^{37}TSSSY$; | SEQ ID NO:32 |
| $AQITP^{37}TEQKY$; | SEQ ID NO:33 |
| $AYIP^{37}TEQSY$; | SEQ ID NO:34 |

4. Internal Mutation Site 3

In this type of mutants, the amino acid sequence surrounding $P^{48}$, $LQNP^{48}QTSLC$; SEQ ID NO:35, is replaced with $LZmJqP^{48}OrXnBoLC$, where at least one of Z, J, O, and X are independently selected from either Thr or Ser. Preferred examples include:

| | |
|---|---|
| $LQTP^{48}QTSLC$; | SEQ ID NO:36 |
| $LQNP^{48}TTSLC$; | SEQ ID NO:37 |

5. Internal Mutation Site 4

In this type of mutants, the amino acid sequence surrounding $P^{59}$, $SESIP^{59}TPNREET$; SEQ ID NO:38, is replaced with $SZmUsJqP^{59}TPOrXnBo\Delta rT$, where at least one of Z, J, O, B, Δ, U, and X is independently selected from either Thr or Ser; B, Δ, and Z may include charged amino acids. Preferred examples include:

| | |
|---|---|
| $SESTP^{59}TPNREET$; | SEQ ID NO:39 |
| $SSSTP^{59}TPNREET$; | SEQ ID NO:40 |
| $SESIP^{59}TPNTEET$; | SEQ ID NO:41 |
| $SESIP^{59}TPNTQET$; | SEQ ID NO:42 |
| $SESIP^{59}TPTQGAT$; | SEQ ID NO:43 |
| $SESIP^{59}TPTESST$; | SEQ ID NO:44 |
| $SQSTP^{59}TPNREET$; | SEQ ID NO:45 |
| $SQSTP^{59}TPNQEET$; | SEQ ID NO:46 |
| $SESTP^{59}TPTSSST$; | SEQ ID NO:47 |

6. Internal Mutation Site 5

In this type of mutants, the amino acid sequence surrounding $P^{89}$, $SWLEP^{89}VQFLRS$; SEQ ID NO:48, is replaced with $SZmUsJqP^{89}OrXnBo\Delta r\lambda tS$, where at least one of Z, U, J, O, B, and X is independently selected from either Thr or Ser; J and λ may include charged amino acids. Preferred examples include:

SWLEP$^{89}$TQGLRS; SEQ ID NO:49

SWLEP$^{89}$TQGATS; SEQ ID NO:50

SSQTP$^{89}$VQFLRS; SEQ ID NO:51

SWLEP$^{89}$TSSLSS; SEQ ID NO:52

SMVTP$^{89}$VQFLRS; SEQ ID NO:53

7. Internal Mutation Site 6

In this type of mutants, the amino acid sequence surrounding P$^{133}$, EDGSP$^{133}$RTGQIF; SEQ ID NO:54, has been replace with EZmUsJqP$^{133}$OrXnBoΔrλtF, where at least one of Z, U, J, O, B, and X is independently selected from either Thr or Ser. Preferred examples include:

EDGSP$^{133}$TTGQIF; SEQ ID NO:55

EDGSP$^{133}$NTGQIF; SEQ ID NO:56

EDGSP$^{133}$TQGQIF; SEQ ID NO:57

EDGSP$^{133}$TVGQIF; SEQ ID NO:58

EDGSP$^{133}$TTTQIF; SEQ ID NO:59

EDGSP$^{133}$TSSQIF; SEQ ID NO:60

EDGSP$^{133}$TTQGIF; SEQ ID NO:61

EDGSP$^{133}$QTGQIF; SEQ ID NO:62

EDGTP$^{133}$NTGQIF; SEQ ID NO:63

EDQTP$^{133}$NTGQIF; SEQ ID NO:64

8. Internal Mutation Site 7

In this type of mutants, the amino acid sequence surrounding P$^{140}$, GQIFK$^{140}$QTYS; SEQ ID NO:65, is replace with GZmUsJqΔr$^{140}$OrXnBoS, where at least one of Z, U, J, O, B, and X is independently selected from either Thr or Ser. Preferred examples include:

GQIFN$^{140}$QTYS; SEQ ID NO:66

GQIFN$^{140}$ITYS; SEQ ID NO:67

GQIFP$^{140}$QTSS; SEQ ID NO:68

-continued

GQIFP$^{140}$TTTS; SEQ ID NO:69

GQITP$^{140}$QTYS; SEQ ID NO:70

GQIFT$^{140}$QTYS; SEQ ID NO:71

GQIST$^{140}$QTYS; SEQ ID NO:72

GQIPT$^{140}$TTYS; SEQ ID NO:73

9. C-terminal Mutations

In this type of mutants, the amino acid sequence at the C-terminus of a wild-type hGH, VEGSCG$^{190}$F; SEQ ID NO:74, is replaced with VEGSCG$^{190}$PXnBoZmUsP, where at least one of Z, U, B, and X is independently selected from either Thr or Ser. Preferred examples include:

VEGSCGPTFTTP; SEQ ID NO:75

VEGSCGPTSSP; SEQ ID NO:76

VEGSCGPTQGAMP; SEQ ID NO:77

VEGSCGPTTIP; SEQ ID NO:78

VEGSCGPMVTP; SEQ ID NO:79

In all above cases, X, Z, B, Δ, J, U, O, and λ are independently selected from E (glutamate), any uncharged amino acid or dipeptide combination including M, F, MF, and the like; m, n, o, p, q, r, s, and t are independently selected from integers from 0 to 3. In all cases, the N-terminal Met may be present or absent on any hGH mutant. The numbering of the amino acid residues is based on the initial unmodified sequence in which the left most residue is numbered 1. The numbering of unmodified amino acids remains unchanged following the modification. More than one of the above described sequence modifications may be present in a hGH mutant of the present invention.

While this invention has been disclosed with reference to specific embodiments, it is apparent that other embodiments and variations of this invention may be devised by others skilled in the art without departing from the true spirit and scope of the invention.

All patents, patent applications, and other publications cited in this application are incorporated by reference in the entirety.

What is claimed is:

1. An isolated human growth hormone polypeptide comprising the amino acid sequence of SEQ ID NO: 1 or SEQ ID NO: 2 except for the presence of at least one O-linked glycosylation site not present in SEQ ID NO: 1 or SEQ ID NO: 2, wherein the O-linked glycosylation site is a serine or threonine residue, and wherein the O-linked glycosylation site is present at a site selected from the group consisting of (a) proximate a proline residue located at position 2, 5, 37, 48, 59, 89, or 133 of SEQ ID NO: 1 or SEQ ID NO: 2, (b) the amino acid sequence surrounding position 140 of SEQ ID NO: 1 or SEQ ID NO: 2, and (c) the amino acid sequence at the C-terminus of SEQ ID NO: 1 or SEQ ID NO: 2.

2. The isolated human growth hormone polypeptide of claim 1, wherein the O-linked glycosylation site is present at a site proximate a proline residue located at position 2, 5, 37, 48, 59, 89, or 133 of SEQ ID NO: 1 or SEQ ID NO: 2.

3. The isolated human growth hormone polypeptide of claim 1, comprising the amino acid sequence of SEQ ID NO: 3, 4, 5, 6, 7, 8, or 9.

4. The isolated human growth hormone polypeptide of claim 1, comprising a plurality of O-linked glycosylation sites not present SEQ ID NO: 1 or SEQ ID NO: 2.

5. The isolated human growth hormone polypeptide of claim 1, comprising a water-soluble polymer attached to the glycosylation site through a glycosyl linker.

6. The isolated human growth hormone polypeptide of claim 5, wherein said glycosyl linker is an intact glycosyl linker.

7. A composition comprising the isolated human growth hormone polypeptide of claim 1 and a carrier therefor.

8. A method of making a glycosylated human growth hormone polypeptide comprising:

a) recombinantly producing the human growth hormone polypeptide of claim 1; and b) glycosylating said human growth hormone polypeptide at the O-linked glycosylation site.

9. The method of claim 8, wherein step b) comprises enzymatically glycosylating said human growth hormone polypeptide with a modified sugar at the O-linked glycosylation site.

10. The method of claim 9, wherein the sugar is modified with a poly(ethylene glycol) or m-poly(ethylene glycol).

11. The method of claim 9, wherein the O-linked glycosylation site is present at a site proximate a proline residue located at position 2, 5, 37, 48, 59, 89, or 133 of SEQ ID NO: 1 or SEQ ID NO: 2.

12. The method of claim 9, wherein said human growth hormone polypeptide comprises the amino acid sequence of SEQ ID NO: 3, 4, 5, 6, 7, 8, or 9.

13. The method of claim 9, wherein said human growth hormone polypeptide comprises a plurality of O-linked glycosylation sites not present in SEQ ID NO: 1 or SEQ ID NO: 2.

14. The method of claim 9, wherein said human growth hormone polypeptide comprises a water-soluble polymer attached to the glycosylation site through a glycosyl linker.

15. The method of claim 14, wherein said glycosyl linker is an intact glycosyl linker.

16. The method of claim 8, wherein the O-linked glycosylation site is present at a site proximate a proline residue located at position 2, 5, 37, 48, 59, 89, or 133 of SEQ ID NO: 1 or SEQ ID NO: 2.

17. The method of claim 8, wherein said human growth hormone polypeptide comprises the amino acid sequence of SEQ ID NO: 3, 4, 5, 6, 7, 8, or 9.

18. The method of claim 8, wherein said human growth hormone polypeptide comprises a plurality of O-linked glycosylation sites not present SEQ ID NO: 1 or SEQ ID NO: 2.

19. The method of claim 8, wherein said human growth hormone polypeptide comprises a water-soluble polymer attached to the glycosylation site through a glycosyl linker.

20. The method of claim 19, wherein said glycosyl linker is an intact glycosyl linker.

21. The isolated human growth hormone polypeptide of claim 1, wherein the isolated human growth hormone polypeptide is glycosylated.

22. The isolated human growth hormone polypeptide of claim 2, wherein the isolated human growth hormone polypeptide is glycosylated.

23. The isolated human growth hormone polypeptide of claim 3, wherein the isolated human growth hormone polypeptide is glycosylated.

24. The isolated human growth hormone polypeptide of claim 4, wherein the isolated human growth hormone polypeptide is glycosylated.

25. A composition comprising the isolated human growth hormone polypeptide of claim 2 and a carrier therefor.

26. A composition comprising the isolated human growth hormone polypeptide of claim 3 and a carrier therefor.

27. A composition comprising the isolated human growth hormone polypeptide of claim 4 and a carrier therefor.

28. A composition comprising the isolated human growth hormone polypeptide of claim 5 and a carrier therefor.

29. A composition comprising the isolated human growth hormone polypeptide of claim 6 and a carrier therefor.

30. A composition comprising the isolated human growth hormone polypeptide of claim 21 and a carrier therefor.

31. A composition comprising the isolated human growth hormone polypeptide of claim 22 and a carrier therefor.

32. A composition comprising the isolated human growth hormone polypeptide of claim 23 and a carrier therefor.

33. A composition comprising the isolated human growth hormone polypeptide of claim 24 and a carrier therefor.

* * * * *

SEQUENCE LISTING

```
<160> NUMBER OF SEQ ID NOS: 79

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
```

-continued

```
50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190


<210> SEQ ID NO 2
<211> LENGTH: 191
<212> TYPE: PRT
<213> ORGANISM: Homo sapiens

<400> SEQUENCE: 2

Phe Pro Thr Ile Pro Leu Ser Arg Leu Phe Asp Asn Ala Met Leu Arg
1               5                   10                  15

Ala Arg Arg Leu Tyr Gln Leu Ala Tyr Asp Thr Tyr Gln Glu Phe Glu
            20                  25                  30

Glu Ala Tyr Ile Leu Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Val Lys Thr Gln Gln Lys Ser Asn Leu Glu Leu Leu Arg Ile Ser Leu
65                  70                  75                  80

Leu Leu Ile Gln Ser Trp Leu Glu Pro Val Gln Leu Leu Arg Ser Val
                85                  90                  95

Phe Ala Asn Ser Leu Val Tyr Gly Ala Ser Asp Ser Asn Val Tyr Arg
            100                 105                 110

His Leu Lys Asp Leu Glu Glu Gly Ile Gln Thr Leu Met Trp Arg Leu
        115                 120                 125

Glu Asp Gly Ser Pro Arg Thr Gly Gln Ile Phe Asn Gln Ser Tyr Ser
    130                 135                 140

Lys Phe Asp Thr Lys Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190


<210> SEQ ID NO 3
<211> LENGTH: 191
<212> TYPE: PRT
<213> ORGANISM: Artificial Sequence
<220> FEATURE:
<223> OTHER INFORMATION: mutant human growth hormone amino acid sequence

<400> SEQUENCE: 3
```

-continued

Phe Pro Thr Ile Pro Leu Ser Arg Leu Phe Asp Asn Ala Met Leu Arg
1 5 10 15

Ala His Arg Leu His Gln Leu Ala Phe Asp Thr Tyr Gln Glu Phe Glu
20 25 30

Glu Ala Tyr Ile Pro Lys Glu Gln Lys Tyr Ser Phe Leu Gln Asn Pro
35 40 45

Gln Thr Ser Leu Cys Phe Ser Glu Ser Ile Pro Thr Pro Ser Asn Arg
50 55 60

Glu Glu Thr Gln Gln Lys Ser Asn Leu Glu Leu Leu Arg Ile Ser Leu
65 70 75 80

Leu Leu Ile Gln Ser Trp Leu Glu Pro Val Gln Phe Leu Arg Ser Val
85 90 95

Phe Ala Asn Ser Leu Val Tyr Gly Ala Ser Asp Ser Asn Val Tyr Asp
100 105 110

Leu Leu Lys Asp Leu Glu Glu Gly Ile Gln Thr Leu Met Gly Arg Leu
115 120 125

Glu Asp Gly Ser Pro Thr Thr Thr Gln Ile Phe Lys Gln Thr Tyr Ser
130 135 140

Lys Phe Asp Thr Asn Ser His Asn Asp Asp Ala Leu Leu Lys Asn Tyr
145 150 155 160

Gly Leu Leu Tyr Cys Phe Arg Lys Asp Met Asp Lys Val Glu Thr Phe
165 170 175

Leu Arg Ile Val Gln Cys Arg Ser Val Glu Gly Ser Cys Gly Phe
180 185 190

<210> SEQ ID NO 4
<211> LENGTH: 194
<212> TYPE: PRT
<213> ORGANISM: Artificial Sequence
<220> FEATURE:
<223> OTHER INFORMATION: mutant human growth hormone amino acid sequence

<400> SEQUENCE: 4

Pro Thr Thr Phe Pro Thr Ile Pro Leu Ser Arg Leu Phe Asp Asn Ala
1 5 10 15

Met Leu Arg Ala His Arg Leu His Gln Leu Ala Phe Asp Thr Tyr Gln
20 25 30

Glu Phe Glu Glu Ala Tyr Ile Pro Lys Glu Gln Lys Tyr Ser Phe Leu
35 40 45

Gln Asn Pro Gln Thr Ser Leu Cys Phe Ser Glu Ser Ile Pro Thr Pro
50 55 60

Ser Asn Arg Glu Glu Thr Gln Gln Lys Ser Asn Leu Glu Leu Leu Arg
65 70 75 80

Ile Ser Leu Leu Leu Ile Gln Ser Trp Leu Glu Pro Val Gln Phe Leu
85 90 95

Arg Ser Val Phe Ala Asn Ser Leu Val Tyr Gly Ala Ser Asp Ser Asn
100 105 110

Val Tyr Asp Leu Leu Lys Asp Leu Glu Glu Gly Ile Gln Thr Leu Met
115 120 125

Gly Arg Leu Glu Asp Gly Ser Pro Arg Thr Gly Gln Ile Phe Lys Gln
130 135 140

Thr Tyr Ser Lys Phe Asp Thr Asn Ser His Asn Asp Asp Ala Leu Leu
145 150 155 160

Lys Asn Tyr Gly Leu Leu Tyr Cys Phe Arg Lys Asp Met Asp Lys Val
165 170 175

Glu Thr Phe Leu Arg Ile Val Gln Cys Arg Ser Val Glu Gly Ser Cys 180 185 190

Gly Phe

<210> SEQ ID NO 5
<211> LENGTH: 191
<212> TYPE: PRT
<213> ORGANISM: Artificial Sequence
<220> FEATURE:
<223> OTHER INFORMATION: mutant human growth hormone amino acid sequence

<400> SEQUENCE: 5

Phe Pro Thr Ile Pro Leu Ser Arg Leu Phe Asp Asn Ala Met Leu Arg
1 5 10 15

Ala His Arg Leu His Gln Leu Ala Phe Asp Thr Tyr Gln Glu Phe Glu
20 25 30

Glu Ala Tyr Ile Pro Lys Glu Gln Lys Tyr Ser Phe Leu Gln Asn Pro
35 40 45

Gln Thr Ser Leu Cys Phe Ser Glu Ser Ile Pro Thr Pro Ser Asn Arg
50 55 60

Glu Glu Thr Gln Gln Lys Ser Asn Leu Glu Leu Leu Arg Ile Ser Leu
65 70 75 80

Leu Leu Ile Gln Ser Trp Leu Glu Pro Val Gln Phe Leu Arg Ser Val
85 90 95

Phe Ala Asn Ser Leu Val Tyr Gly Ala Ser Asp Ser Asn Val Tyr Asp
100 105 110

Leu Leu Lys Asp Leu Glu Glu Gly Ile Gln Thr Leu Met Gly Arg Leu
115 120 125

Glu Asp Gly Ser Pro Thr Thr Gly Gln Ile Phe Lys Gln Thr Tyr Ser
130 135 140

Lys Phe Asp Thr Asn Ser His Asn Asp Asp Ala Leu Leu Lys Asn Tyr
145 150 155 160

Gly Leu Leu Tyr Cys Phe Arg Lys Asp Met Asp Lys Val Glu Thr Phe
165 170 175

Leu Arg Ile Val Gln Cys Arg Ser Val Glu Gly Ser Cys Gly Phe
180 185 190

<210> SEQ ID NO 6
<211> LENGTH: 193
<212> TYPE: PRT
<213> ORGANISM: Artificial Sequence
<220> FEATURE:
<223> OTHER INFORMATION: mutant human growth hormone amino acid sequence

<400> SEQUENCE: 6

Met Val Thr Pro Thr Ile Pro Leu Ser Arg Leu Phe Asp Asn Ala Met
1 5 10 15

Leu Arg Ala His Arg Leu His Gln Leu Ala Phe Asp Thr Tyr Gln Glu
20 25 30

Phe Glu Glu Ala Tyr Ile Pro Lys Glu Gln Lys Tyr Ser Phe Leu Gln
35 40 45

Asn Pro Gln Thr Ser Leu Cys Phe Ser Glu Ser Ile Pro Thr Pro Ser
50 55 60

Asn Arg Glu Glu Thr Gln Gln Lys Ser Asn Leu Glu Leu Leu Arg Ile
65 70 75 80

Ser Leu Leu Leu Ile Gln Ser Trp Leu Glu Pro Val Gln Phe Leu Arg
85 90 95

Ser Val Phe Ala Asn Ser Leu Val Tyr Gly Ala Ser Asp Ser Asn Val
100 105 110

```
Tyr Asp Leu Leu Lys Asp Leu Glu Glu Gly Ile Gln Thr Leu Met Gly
       115                 120                 125

Arg Leu Glu Asp Gly Ser Pro Arg Thr Gly Gln Ile Phe Lys Gln Thr
   130                 135                 140

Tyr Ser Lys Phe Asp Thr Asn Ser His Asn Asp Asp Ala Leu Leu Lys
145                 150                 155                 160

Asn Tyr Gly Leu Leu Tyr Cys Phe Arg Lys Asp Met Asp Lys Val Glu
                165                 170                 175

Thr Phe Leu Arg Ile Val Gln Cys Arg Ser Val Glu Gly Ser Cys Gly
           180                 185                 190

Phe


<210> SEQ ID NO 7
<211> LENGTH: 193
<212> TYPE: PRT
<213> ORGANISM: Artificial Sequence
<220> FEATURE:
<223> OTHER INFORMATION: mutant human growth hormone amino acid sequence

<400> SEQUENCE: 7

Met Val Thr Pro Thr Ile Pro Leu Ser Arg Leu Phe Asp Asn Ala Met
1               5                   10                  15

Leu Arg Ala His Arg Leu His Gln Leu Ala Phe Asp Thr Tyr Gln Glu
           20                  25                  30

Phe Glu Glu Ala Tyr Ile Pro Lys Glu Gln Lys Tyr Ser Phe Leu Gln
       35                  40                  45

Asn Pro Gln Thr Ser Leu Cys Phe Ser Glu Ser Ile Pro Thr Pro Ser
   50                  55                  60

Asn Arg Glu Glu Thr Gln Gln Lys Ser Asn Leu Glu Leu Leu Arg Ile
65                  70                  75                  80

Ser Leu Leu Leu Ile Gln Ser Trp Leu Glu Pro Val Gln Phe Leu Arg
                85                  90                  95

Ser Val Phe Ala Asn Ser Leu Val Tyr Gly Ala Ser Asp Ser Asn Val
           100                 105                 110

Tyr Asp Leu Leu Lys Asp Leu Glu Glu Gly Ile Gln Thr Leu Met Gly
       115                 120                 125

Arg Leu Glu Asp Gly Ser Pro Arg Thr Gly Gln Ile Phe Lys Gln Thr
   130                 135                 140

Tyr Ser Lys Phe Asp Thr Asn Ser His Asn Asp Asp Ala Leu Leu Lys
145                 150                 155                 160

Asn Tyr Gly Leu Leu Tyr Cys Phe Arg Lys Asp Met Asp Lys Val Glu
                165                 170                 175

Thr Phe Leu Arg Ile Val Gln Cys Arg Ser Val Glu Gly Ser Cys Gly
           180                 185                 190

Phe


<210> SEQ ID NO 8
<211> LENGTH: 192
<212> TYPE: PRT
<213> ORGANISM: Artificial Sequence
<220> FEATURE:
<223> OTHER INFORMATION: mutant human growth hormone amino acid sequence

<400> SEQUENCE: 8

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
```

```
        20                  25                  30

Glu Glu Ala Tyr Ile Pro Lys Glu Gln Lys Tyr Ser Phe Leu Gln Asn
    35                  40                  45

Pro Gln Thr Ser Leu Cys Phe Ser Glu Ser Ile Pro Thr Pro Ser Asn
  50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Val Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190


<210> SEQ ID NO 9
<211> LENGTH: 192
<212> TYPE: PRT
<213> ORGANISM: Artificial Sequence
<220> FEATURE:
<223> OTHER INFORMATION: mutant human growth hormone amino acid sequence

<400> SEQUENCE: 9

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Thr Thr Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190


<210> SEQ ID NO 10
```

<211> LENGTH: 6
<212> TYPE: PRT
<213> ORGANISM: Homo sapiens

<400> SEQUENCE: 10

Phe Pro Thr Ile Pro Leu
1 5

<210> SEQ ID NO 11
<211> LENGTH: 5
<212> TYPE: PRT
<213> ORGANISM: Homo sapiens

<400> SEQUENCE: 11

Pro Gln Thr Ser Leu
1 5

<210> SEQ ID NO 12
<211> LENGTH: 6
<212> TYPE: PRT
<213> ORGANISM: Homo sapiens

<400> SEQUENCE: 12

Pro Thr Pro Ser Asn Arg
1 5

<210> SEQ ID NO 13
<211> LENGTH: 7
<212> TYPE: PRT
<213> ORGANISM: Homo sapiens

<400> SEQUENCE: 13

Pro Arg Thr Gly Gln Ile Phe
1 5

<210> SEQ ID NO 14
<211> LENGTH: 13
<212> TYPE: PRT
<213> ORGANISM: Homo sapiens

<400> SEQUENCE: 14

Pro Arg Thr Gly Gln Ile Phe Lys Gln Thr Tyr Ser Lys
1 5 10

<210> SEQ ID NO 15
<211> LENGTH: 4
<212> TYPE: PRT
<213> ORGANISM: Homo sapiens

<400> SEQUENCE: 15

Phe Lys Gln Thr
1

<210> SEQ ID NO 16
<211> LENGTH: 7
<212> TYPE: PRT
<213> ORGANISM: Homo sapiens

<400> SEQUENCE: 16

Phe Pro Thr Ile Pro Leu Ser
1 5

<210> SEQ ID NO 17
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 17

Met Val Thr Pro Thr Ile Pro Leu Ser
1 5

<210> SEQ ID NO 18
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 18

Met Gln Thr Pro Thr Ile Pro Leu Ser
1 5

<210> SEQ ID NO 19
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 19

Met Ala Pro Thr Ser Ser Pro Thr Ile Pro Leu Ser
1 5 10

<210> SEQ ID NO 20
<211> LENGTH: 13
<212> TYPE: PRT
<213> ORGANISM: Artificial Sequence
<220> FEATURE:
<223> OTHER INFORMATION: mutant glycosylation site

<400> SEQUENCE: 20

Met Ala Pro Thr Ser Ser Ser Pro Thr Ile Pro Leu Ser
1 5 10

<210> SEQ ID NO 21
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 21

Met Pro Thr Thr Phe Pro Thr Ile Pro Leu Ser
1 5 10

<210> SEQ ID NO 22
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 22

Met Pro Thr Ser Ser Pro Thr Ile Pro Leu Ser
1 5 10

<210> SEQ ID NO 23
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 23

Met Pro Thr Ser Ser Ser Pro Thr Ile Pro Leu Ser
1 5 10

<210> SEQ ID NO 24
<211> LENGTH: 7
<212> TYPE: PRT
<213> ORGANISM: Homo sapiens

<400> SEQUENCE: 24

Phe Pro Thr Ile Pro Leu Ser
1 5

<210> SEQ ID NO 25
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 25

Met Phe Pro Thr Gln Ile Pro Leu Ser
1 5

<210> SEQ ID NO 26
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 26

Met Phe Pro Thr Ser Ile Pro Leu Ser
1 5

<210> SEQ ID NO 27
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 27

Met Phe Pro Thr Ser Ser Pro Leu Ser
1 5

<210> SEQ ID NO 28
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 28

Met Thr Pro Thr Gln Ile Pro Leu Ser
1 5

<210> SEQ ID NO 29
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 29

Met Phe Pro Thr Thr Thr Pro Leu Ser 1 5

<210> SEQ ID NO 30
<211> LENGTH: 9
<212> TYPE: PRT
<213> ORGANISM: Homo sapiens

<400> SEQUENCE: 30

Ala Tyr Ile Pro Lys Glu Gln Lys Tyr
1 5

<210> SEQ ID NO 31
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 31

Ala Tyr Ile Pro Thr Gln Gly Ala Tyr
1 5

<210> SEQ ID NO 32
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 32

Ala Tyr Ile Pro Thr Ser Ser Ser Tyr
1 5

<210> SEQ ID NO 33
<211> LENGTH: 10
<212> TYPE: PRT
<213> ORGANISM: Artificial Sequence
<220> FEATURE:
<223> OTHER INFORMATION: mutant glycosylation site

<400> SEQUENCE: 33

Ala Gln Ile Thr Pro Thr Glu Gln Lys Tyr
1 5 10

<210> SEQ ID NO 34
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 34

Ala Tyr Ile Pro Thr Glu Gln Ser Tyr
1 5

<210> SEQ ID NO 35
<211> LENGTH: 9
<212> TYPE: PRT
<213> ORGANISM: Homo sapiens

<400> SEQUENCE: 35

Leu Gln Asn Pro Gln Thr Ser Leu Cys
1 5

<210> SEQ ID NO 36
<211> LENGTH: 9
<212> TYPE: PRT

<213> ORGANISM: Artificial Sequence
<220> FEATURE:
<223> OTHER INFORMATION: mutant glycosylation site

<400> SEQUENCE: 36

Leu Gln Thr Pro Gln Thr Ser Leu Cys
1 5

<210> SEQ ID NO 37
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 37

Leu Gln Asn Pro Thr Thr Ser Leu Cys
1 5

<210> SEQ ID NO 38
<211> LENGTH: 12
<212> TYPE: PRT
<213> ORGANISM: Homo sapiens

<400> SEQUENCE: 38

Ser Glu Ser Ile Pro Thr Pro Asn Arg Glu Glu Thr
1 5 10

<210> SEQ ID NO 39
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 39

Ser Glu Ser Thr Pro Thr Pro Asn Arg Glu Glu Thr
1 5 10

<210> SEQ ID NO 40
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 40

Ser Ser Ser Thr Pro Thr Pro Asn Arg Glu Glu Thr
1 5 10

<210> SEQ ID NO 41
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 41

Ser Glu Ser Ile Pro Thr Pro Asn Thr Glu Glu Thr
1 5 10

<210> SEQ ID NO 42
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 42

Ser Glu Ser Ile Pro Thr Pro Asn Thr Gln Glu Thr
1 5 10

<210> SEQ ID NO 43
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 43

Ser Glu Ser Ile Pro Thr Pro Thr Gln Gly Ala Thr
1 5 10

<210> SEQ ID NO 44
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 44

Ser Glu Ser Ile Pro Thr Pro Thr Glu Ser Ser Thr
1 5 10

<210> SEQ ID NO 45
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 45

Ser Gln Ser Thr Pro Thr Pro Asn Arg Glu Glu Thr
1 5 10

<210> SEQ ID NO 46
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 46

Ser Gln Ser Thr Pro Thr Pro Asn Gln Glu Glu Thr
1 5 10

<210> SEQ ID NO 47
<211> LENGTH: 12
<212> TYPE: PRT
<213> ORGANISM: Artificial Sequence
<220> FEATURE:
<223> OTHER INFORMATION: mutant glycosylation site

<400> SEQUENCE: 47

Ser Glu Ser Thr Pro Thr Pro Thr Ser Ser Ser Thr
1 5 10

<210> SEQ ID NO 48
<211> LENGTH: 11
<212> TYPE: PRT
<213> ORGANISM: Homo sapiens

<400> SEQUENCE: 48

Ser Trp Leu Glu Pro Val Gln Phe Leu Arg Ser
1 5 10

<210> SEQ ID NO 49
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 49

```
Ser Trp Leu Glu Pro Thr Gln Gly Leu Arg Ser
1               5                   10
```

<210> SEQ ID NO 50
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 50

```
Ser Trp Leu Glu Pro Thr Gln Gly Ala Thr Ser
1               5                   10
```

<210> SEQ ID NO 51
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 51

```
Ser Ser Gln Thr Pro Val Gln Phe Leu Arg Ser
1               5                   10
```

<210> SEQ ID NO 52
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 52

```
Ser Trp Leu Glu Pro Thr Ser Ser Leu Ser Ser
1               5                   10
```

<210> SEQ ID NO 53
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 53

```
Ser Met Val Thr Pro Val Gln Phe Leu Arg Ser
1               5                   10
```

<210> SEQ ID NO 54
<211> LENGTH: 11
<212> TYPE: PRT
<213> ORGANISM: Homo sapiens

<400> SEQUENCE: 54

```
Glu Asp Gly Ser Pro Arg Thr Gly Gln Ile Phe
1               5                   10
```

<210> SEQ ID NO 55
<211> LENGTH: 11

<212> TYPE: PRT
<213> ORGANISM: Artificial Sequence
<220> FEATURE:
<223> OTHER INFORMATION: mutant glycosylation site

<400> SEQUENCE: 55

Glu Asp Gly Ser Pro Thr Thr Gly Gln Ile Phe
1 5 10

<210> SEQ ID NO 56
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 56

Glu Asp Gly Ser Pro Asn Thr Gly Gln Ile Phe
1 5 10

<210> SEQ ID NO 57
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 57

Glu Asp Gly Ser Pro Thr Gln Gly Gln Ile Phe
1 5 10

<210> SEQ ID NO 58
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 58

Glu Asp Gly Ser Pro Thr Val Gly Gln Ile Phe
1 5 10

<210> SEQ ID NO 59
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 59

Glu Asp Gly Ser Pro Thr Thr Thr Gln Ile Phe
1 5 10

<210> SEQ ID NO 60
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 60

Glu Asp Gly Ser Pro Thr Ser Ser Gln Ile Phe
1 5 10

<210> SEQ ID NO 61
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 61

Glu Asp Gly Ser Pro Thr Thr Gln Gly Ile Phe
1 5 10

<210> SEQ ID NO 62
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 62

Glu Asp Gly Ser Pro Gln Thr Gly Gln Ile Phe
1 5 10

<210> SEQ ID NO 63
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 63

Glu Asp Gly Thr Pro Asn Thr Gly Gln Ile Phe
1 5 10

<210> SEQ ID NO 64
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 64

Glu Asp Gln Thr Pro Asn Thr Gly Gln Ile Phe
1 5 10

<210> SEQ ID NO 65
<211> LENGTH: 9
<212> TYPE: PRT
<213> ORGANISM: Homo sapiens

<400> SEQUENCE: 65

Gly Gln Ile Phe Lys Gln Thr Tyr Ser
1 5

<210> SEQ ID NO 66
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 66

Gly Gln Ile Phe Asn Gln Thr Tyr Ser
1 5

<210> SEQ ID NO 67
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 67

Gly Gln Ile Phe Asn Ile Thr Tyr Ser
1 5

<210> SEQ ID NO 68
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 68

Gly Gln Ile Phe Pro Gln Thr Ser Ser
1 5

<210> SEQ ID NO 69
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 69

Gly Gln Ile Phe Pro Thr Thr Thr Ser
1 5

<210> SEQ ID NO 70
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 70

Gly Gln Ile Thr Pro Gln Thr Tyr Ser
1 5

<210> SEQ ID NO 71
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 71

Gly Gln Ile Phe Thr Gln Thr Tyr Ser
1 5

<210> SEQ ID NO 72
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 72

Gly Gln Ile Ser Thr Gln Thr Tyr Ser
1 5

<210> SEQ ID NO 73
<211> LENGTH: 9
<212> TYPE: PRT
<213> ORGANISM: Artificial Sequence
<220> FEATURE:
<223> OTHER INFORMATION: mutant glycosylation site

<400> SEQUENCE: 73

Gly Gln Ile Pro Thr Thr Thr Tyr Ser

-continued

```
1               5


<210> SEQ ID NO 74
<211> LENGTH: 7
<212> TYPE: PRT
<213> ORGANISM: Homo sapiens

<400> SEQUENCE: 74

Val Glu Gly Ser Cys Gly Phe
1               5


<210> SEQ ID NO 75
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 75

Val Glu Gly Ser Cys Gly Pro Thr Thr Thr Pro
1               5                   10


<210> SEQ ID NO 76
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 76

Val Glu Gly Ser Cys Gly Pro Thr Ser Ser Pro
1               5                   10


<210> SEQ ID NO 77
<211> LENGTH: 13
<212> TYPE: PRT
<213> ORGANISM: Artificial Sequence
<220> FEATURE:
<223> OTHER INFORMATION: mutant glycosylation site

<400> SEQUENCE: 77

Val Glu Gly Ser Cys Gly Pro Thr Gln Gly Ala Met Pro
1               5                   10


<210> SEQ ID NO 78
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 78

Val Glu Gly Ser Cys Gly Pro Thr Thr Ile Pro
1               5                   10


<210> SEQ ID NO 79
<211> LENGTH: 11
<212> TYPE: PRT
<213> ORGANISM: Artificial Sequence
<220> FEATURE:
<223> OTHER INFORMATION: mutant glycosylation site

<400> SEQUENCE: 79

Val Glu Gly Ser Cys Gly Pro Met Val Thr Pro
1               5                   10
```